US007179621B1

(12) United States Patent
Chader et al.

(10) Patent No.: US 7,179,621 B1
(45) Date of Patent: Feb. 20, 2007

(54) PIGMENT EPITHELIUM-DERIVED FACTOR: SEQUENCE OF THE PEDF GENE

(75) Inventors: Gerald J. Chader, Bethesda, MD (US); Ignacio R. Rodriguez, Rockville, MD (US); Joyce Tombran-Tink, Derwood, MD (US); Sofia Patricia Becerra, Bethesda, MD (US); Fintan R. Steele, Washington, DC (US); Lincoln V. Johnson, Pasadena, CA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 345 days.

(21) Appl. No.: 09/630,629

(22) Filed: Aug. 1, 2000

Related U.S. Application Data

(60) Division of application No. 08/367,841, filed on Dec. 30, 1994, now Pat. No. 6,319,687, which is a continuation-in-part of application No. 08/279,979, filed on Jul. 25, 1994, now abandoned, which is a continuation-in-part of application No. 07/952,796, filed on Sep. 24, 1992, now abandoned, and a continuation-in-part of application No. 07/894,215, filed on Jul. 4, 1992, now abandoned, said application No. 08/367, 841 is a continuation-in-part of application No. 08/257,963, filed on Jun. 7, 1994, now Pat. No. 5,840,686, which is a continuation-in-part of application No. 07/952,796, filed on Sep. 24, 1992, now abandoned.

(51) Int. Cl.
*C12N 15/18* (2006.01)
*C12N 15/79* (2006.01)
*C12N 15/63* (2006.01)
*C12N 1/21* (2006.01)

(52) U.S. Cl. ............... 435/69.4; 435/325; 435/252.3; 435/240.1; 536/23.51

(58) Field of Classification Search ............ 536/23.51; 435/69.4, 320.1, 325, 252.3
See application file for complete search history.

(56) References Cited

U.S. PATENT DOCUMENTS

| | | | |
|---|---|---|---|
| 1,700,691 A | 1/1929 | Stuart | |
| 4,477,435 A | 10/1984 | Courtois et al. | |
| 4,534,967 A | 8/1985 | Jacobson et al. | |
| 4,670,257 A | 6/1987 | Guedon born Saglier et al. | |
| 4,770,877 A | 9/1988 | Jacobson | |
| 4,996,159 A | 2/1991 | Glaser | |

OTHER PUBLICATIONS

Rudinger, In "Peptide Hormones" (ed. J.A.Parsons) University Park Press, Baltimore, pp. 1-7, 1976*
Steele et al. Proc. Natl. Acad. Sci. USA 90: 1526-1530, 1993.*
Becerra et al., "Recombinant Human Fetal Retinal Pigment Epithelium-Derived Factor (PEDF)," Abstract 658-60, presented at Investigative Ophthalmology & Visual Science Annual Meeting (May 3-May 8, 1992).
Becerra et al., "A Novel Retinal Neurotrophic Factor (PEDF): A Serine Protease Inhibitor?," presented at NIH Research Festival 1992 (Sep. 21-25, 1992).
Tombran-Tink et al., "RPE-54—A Unique RPE Product with Neuronal Differentiating Activity," *Investigative Ophthalmology & Visual Science*, 29, 414 (1989).
Tombran-Tink et al., "Neuronal Differentiation of Retinoblastoma Cells Induced by Medium Conditioned by Human RPE Cells," *Investigative Ophthalmology & Visual Science*, 30(8), 1700-1707 (1989).
Tombran-Tink et al., "PEDF: A Pigment Epithelium-derived Factor with Potent Neuronal Differentiative Activity," *Experimental Eye Research*, 53, 411-414 (1991).
Tombran-Tink et al., Molecular Cloning and Chromosomal Localization of the Gene for Human Pigment Epithelium-Derived Factor (PEDF), *Investigative Ophthalmology & Visual Science*, 33(4), 828 (1992).
Zhiqiang Zou et al., "Maspin, A Serpin With Tumor-Suppressing Activity In Human Mammary Epithelial Cells," *Science*, vol. 263, pp. 526-530, Jan. 28, 1994.
S. P. Becerra, et al., "Structure-Function Studies of Pigment Epithelium Derived Factor (PEDF)," *The FASEB Journal* (Abstract No. 192), vol. 7, No. 7, Apr. 20, 1993.
R. J. Pignolo, et al., "Senescent WI-38 Cells Fail to Express *EPC-1*, A Gene Induced In Young Cells Upon Entry Into the G State," *The Journal of Biological Chemistry*, vol. 268, No. 12, Apr. 25, 1993, pp. 8949-8957.
J. Tombran-Tink et al., "Neurotrophic Activity of Interphotoreceptor Matrix on Human Y79 Retinoblastoma Cells," *The Journal of Comparative Neurology*, 1992.
Tombran-Tink et al., "Localization of the Gene for Pigment Epithelium-Derived Factor (PEDF) to Chromosome 17p13.1 and Expression in Cultured Human Retinoblastoma Cells" *Genomics* 19:266-272, 1994.
Steele, F.R. et al., "Pigment epithelium-derived factor: neurotrophic activity and identification as a member of the serine protease inhibitor gene family," *Proc. Natl. Acad. Sci. USA*, 1993, 90(4), 1526-1530, Genbank Data Bank, Accession No. M76979, submission incorporating comparison of SEQ ID NO: 1, two pages (total pages, 4).

* cited by examiner

*Primary Examiner*—Robert C. Hayes
(74) *Attorney, Agent, or Firm*—Woodcock Washburn LLP

(57) ABSTRACT

Nucleic acids encoding the neurotrophic protein known as pigment epithelium derived factor (PEDF), a truncated version of PEDF referred to as rPEDF, and equivalent proteins, vectors comprising such nucleic acids, host cells into which such vectors have been introduced, recombinant methods for producing PEDF, rPEDF, and equivalent proteins, the rPEDF protein and equivalent proteins of rPEDF and PEDF-BP, -BX and BA, and the PEDF protein produced by recombinant methods. Effects and uses of these variants on 1) neuronal differentiation (neurotrophic effect) 2) neuron survival (neuronotrophic effect) and 3) glial inhibition (gliastatic effect) are described.

52 Claims, 20 Drawing Sheets

FIG. 3

Figure 1:
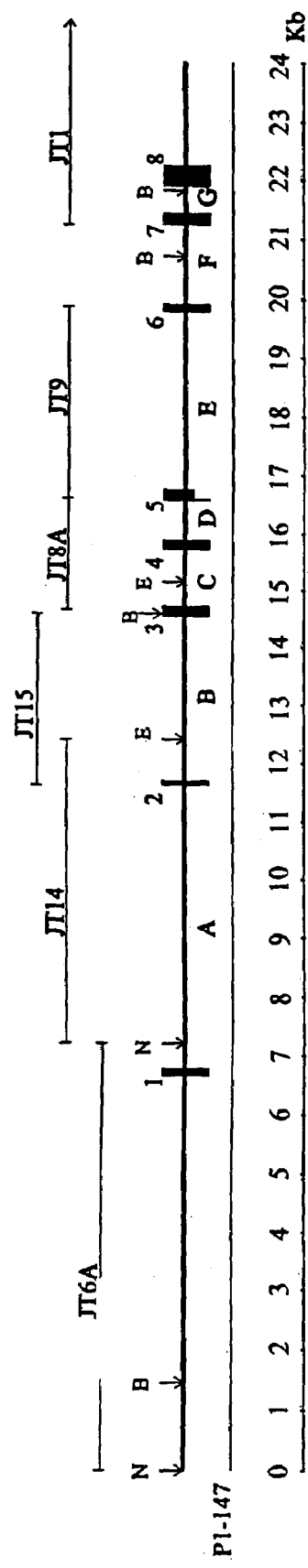

```
-1050 tgggaggctgagggggcgggatcacctgaggtcaggagtttgagacaag -1001
-1000 cgtgaccaatgtggtgaaaccctgtctctactaaaaatacaaaaattagc -951
 -950 cgggcatgctcgtgcacacctatagtcccaactactcagcagggtgaggc -901
 -900 aggagaacctcttgaacccgggaagcggaggttgcagtgagccgacattg -851
 -850 cacccctgcactccagcctgggtgacagagtgagtctccactggaaaaaa -801
 -800 aaaaaaagaacagtgtgatacattgacctaaggtttaagaacatgcaaa -751
 -750 ctgatactatatatcacttagggacaaaaacttacatggtaaaagtaaaa -701
                                                 C/EBP
 -700 agaaatgtacgaaaataataaaaatcaaattcaagatggtggttatggtg -651
 -650 acgggaaagaactgaggcggaaatataaggttgtcactatattgagaaat -601
 -600 ttttctatctttttttctttttttcttttttgagacggggtctcgctctg -551
 -550 tcgcccaggatggagtgcagtggtgtgatctcagctcactgcaacctccg -501
 -500 cctcccaggtttaagtgattctcctgcctcagactcccaagtagctggga -451
 -450 ctacaggtgcgcgccaacacacctgggtaattttgtttgtattttagta -401
 -400 gagatggggtttcaccgtgttgactaggctggtctcgaactcctgacctc -351
 -350 aggtgatccccggcctcggtctcccaaagtgctgggataacaagcgtga -301
 -300 gccactgcgcccagctttgtttgcattttaggtgagatggggtttcacc -251
                                           TREp/RAR
 -250 acgttggccaggctggtcttgaactcctgacctcaggtgatgcacctgcc -201
 -200 tcagtctcccaaagtgctggattacaggcgttagcccctgcgcccggccc -151
         PEA3         PEA3  PEA3          Oct
 -150 ctgaaggaaaatctaaaggaagaggaaggtgtgcaaatgtgtgcgcctta -101
                                      HNF-1
 -100 ggcgtaatgatggtggtgcagcagtgggttaaagttaacacgagacagtg -51
                                Oct       AP-1?
  -50 atgcaatcacagaatccaaattgagtgcaggtcgctttaagaaaggagta -1
      GCTGTAATCTGAAGCCTGCTGGACGCTGGATTAGAAGGCAGCAAAAAAAG
      CTCTGTGCTGGCTGGAGCCCCCTCAGTGTGCAGGCTTAGAGGGACTAGGC
      TGGGTGTGGAGCTGCAGCGTATCCACAG
```

PIGMENT EPITHELIUM-DERIVED FACTOR: SEQUENCE OF THE PEDF GENE

CROSS-REFERENCE TO RELATED APPLICATIONS

This application is a divisional of application Ser. No. 08/367,841, filed Dec. 30, 1994, now U.S. Pat. No. 6,319,687, which is a continuation-in-part of application Ser. No. 08/279,979, filed Jul. 25, 1994, now abandoned, which is a continuation-in-part of application Ser. No. 07/952,796, filed, Sep. 24, 1992, now abandoned, and a continuation-in-part of application Ser. No. 07/894,215, filed Jun. 4, 1992, now abandoned; application Ser. No. 08/367,841, filed Dec. 30, 1994, now U.S. Pat. No. 6,319,687, is also a continuation-in-part of application Ser. No. 08/257,963, filed Jun. 7, 1994, now U.S. Pat. No. 5,840,686, which is a continuation-in-part of application Ser. No. 07/952,796, filed Sep. 24, 1992, now abandoned.

TECHNICAL FIELD OF THE INVENTION

This invention relates to a neurotrophic, neuronotrophic and gliastatic protein. More specifically, this invention relates to the biological properties of a protein known as pigment epithelium-derived factor (PEDF) and recombinant forms of the protein. This invention also relates to a truncated version of PEDF that is referred to as rPEDF. In addition to PEDF and rPEDF and functionally equivalent proteins, this invention relates to nucleic acids that encode rPEDF, and fragments thereof, to vectors comprising such nucleic acids, to host cells into which such vectors have been introduced, and to the use of these host cells to produce such proteins.

BACKGROUND OF THE INVENTION

Pigment epithelium-derived factor, otherwise known as pigment epithelium differentiation-factor, was identified in the conditioned medium of cultured fetal human retinal pigment epithelial cells as an extracellular neurotrophic agent capable of inducing neurite outgrowth in cultured human retinoblastoma cells (Tombran-Tink et al. (1989) *Invest. Ophthalmol. Vis. Sci.*, 30 (8), 1700–1707). The source of PEDF, namely the retinal pigment epithelium (RPE), may be crucial to the normal development and function of the neural retina. A variety of molecules, including growth factors, are synthesized and secreted by RPE cells. Given that the RPE develops prior to and lies adjacent to the neural retina, and that it functions as part of the blood-retina barrier (Fine et al. (1979) *The Retina, Ocular Histology: A Text and Atlas*, New York, Harper & Row, 61–70), the RPE has been implicated in vascular, inflammatory, degenerative, and dystrophic diseases of the eye (Elner et al. (1990) *Am. J. Pathol.*, 136, 745–750). In addition to growth factors, nutrients and metabolites are also exchanged between the RPE and the retina. For example, the RPE supplies to the retina the well-known growth factors PDGF, FGF, TGF-α, and TGF-β (Campochiaro et al. (1988) *Invest. Ophthalmol. Vis. Sci.*, 29, 305–311; Plouet (1988) *Invest. Ophthalmol. Vis. Sci.*, 29, 106–114; Fassio et al. (1988) *Invest. Ophthalmol. Vis. Sci.*, 29, 242–250; Connor et al. (1988) *Invest. Ophthalmol. Vis. Sci.*, 29, 307–313). It is very likely that these and other unknown factors supplied by the RPE influence the organization, differentiation, and normal functioning of the retina.

In order to study and determine the effects of putative differentiation factors secreted by the RPE, cultured cells have been subjected to retinal extracts and conditioned medium obtained from cultures of human fetal RPE cells. For example, U.S. Pat. No. 4,996,159 (Glaser) discloses a neovascularization inhibitor recovered from RPE cells that is of a molecular weight of about 57,000+/–3,000. Similarly, U.S. Pat. No. 1,700,691 (Stuart), U.S. Pat. No. 4,477,435 (Courtois et al.), and U.S. Pat. No. 4,670,257 (Guedon born Saglier et al.) disclose retinal extracts and the use of these extracts for cellular regeneration and treatment of ocular disease. Furthermore, U.S. Pat. No. 4,770,877 (Jacobson) and U.S. Pat. No. 4,534,967 (Jacobson et al.) describe cell proliferation inhibitors purified from the posterior portion of bovine vitreous humor.

PEDF only recently has been isolated from human RPE as a 50-kDa protein (Tombran-Tink et al. (1989) *Invest. Ophthalmol. Vis. Sci.*, 29, 414; Tombran-Tink et al. (1989) *Invest. Ophthalmol. Vis. Sci.*, 30, 1700–1707; Tombran-Tink et al. (1991) *Exp. Eye Res.*, 53, 411–414). Specifically, PEDF has been demonstrated to induce the differentiation of human Y79 retinoblastoma cells, which are a neoplastic counterpart of normal retinoblasts (Chader (1987) *Cell Different.*, 20, 209–216). The differentiative changes induced by PEDF include the extension of a complex meshwork of neurites, and expression of neuronal markers such as neuron-specific enolase and neurofilament proteins. This is why the synthesis and secretion of PEDF protein by the RPE is believed to influence the development and differentiation of the neural retina. Furthermore, PEDF is only highly expressed in undifferentiated human retinal cells, like Y79 retinoblastoma cells, but is either absent or down-regulated in their differentiated counterparts. Recently, it was reported that PEDF mRNA is expressed in abundance in quiescent human fetal W1 fibroblast cells and not expressed in their senescent counterparts (Pignolo et al., 1993).

Further study of PEDF and examination of its potential therapeutic use in the treatment of inflammatory, vascular, degenerative, and dystrophic diseases of the retina and central nervous system (CNS) necessitates the obtention of large quantities of PEDF. Unfortunately, the low abundance of PEDF in fetal human eye and furthermore, the rare availability of its source tissue, especially in light of restrictions on the use of fetal tissue in research and therapeutic applications, make further study of PEDF difficult at best. Therefore, there remains a need for large quantities of PEDF and equivalent proteins. Accordingly, the obtention of nucleic acids that encode PEDF and equivalent proteins, and the capacity to produce PEDF and equivalent proteins in large quantities would significantly impact upon the further study of PEDF, its structure, biochemical activity and cellular function, as well as the discovery and design of therapeutic uses for PEDF.

SUMMARY OF THE INVENTION

It is an object of the present invention to provide nucleic acids encoding for PEDF and functional fragments thereof, vectors comprising such nucleic acids, host cells into which such vectors have been introduced, and a recombinant method of producing PEDF and equivalent proteins. It is another object of the present invention to obtain the genomic DNA sequences encoding for PEDF, identify the intron-exon junctions, the chromosome location in the human genome, and to provide the regulatory regions of the gene which flank the genomic sequence. The present invention relates to such genomic PEDF DNA.

It is a further object of the present invention to provide structural characteristics of PEDF and its similarities to the serpin family of serine protease inhibitors, both structural and functional.

It is yet another object of the present invention to provide PEDF and equivalent proteins produced in accordance with such a recombinant method, wherein the PEDF and equivalent proteins so produced are free from the risks associated with the isolation of PEDF from naturally-occurring source organisms.

Another object of the present invention is to provide nucleic acids for a truncated version of PEDF, referred to as rPEDF, and equivalent proteins, vectors comprising such nucleic acids, host cells into which such vectors have been introduced, and a recombinant method of producing rPEDF and equivalent proteins. It is also an object of the present invention to provide rPEDF and equivalent proteins produced in accordance with such a recombinant method.

It is a further object of the invention to provide a PEDF protein having neuronotrophic and gliastatic activity. The neuronotrophic activity is seen in the prolonged survival of neuronal cells. The gliastatic activity is observed in the inhibition of growth of glial cells in the presence of PEDF or active fragment thereof. It is another object of the invention to provide methods for treating neuronal cells so as to promote/enhance neuron survival and prevent growth of glial cells, comprising treating such cell populations with an effective amount of PEDF or an active fragment thereof.

It is yet another object of the present invention to provide antibodies which specifically recognize PEDF, either monoclonal or polyclonal antibodies, raised against native protein, the recombinant protein or an immunoreactive fragment thereof. It is an object of the invention to provide methods for detecting PEDF by immunoassay using such antibody preparation in determining aging and/or other degenerative diseases. Another object of the invention relates to a method of using PEDF antibodies to specifically inhibit PEDF activity.

These and other objects and advantages of the present invention, as well as additional inventive features, will be apparent from the description of the invention provided herein.

DESCRIPTIONS OF THE FIGURES

FIG. 1: Human PEDF Gene Structure: Restriction map and organization of the human PEDF gene. The human full length genomic PEDF sequence is represented by SEQ ID NO: 43. Exons 1–8 are indicated by black boxes and numbered 1–8. Introns and flanking DNA are represented by horizontal line and are labeled A–G. Positions of several genomic clones are shown above and below the diagrammed gene. Recognition sites for the restriction endonuclease, NotI ("N"), BamHI ("B") and EcoRI ("E") are indicated by vertical arrows.

Figure 2A:
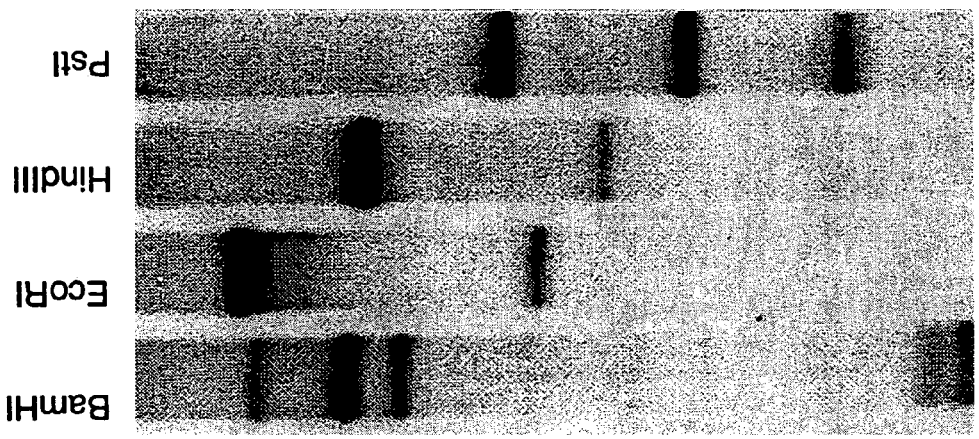
Figure 2B:
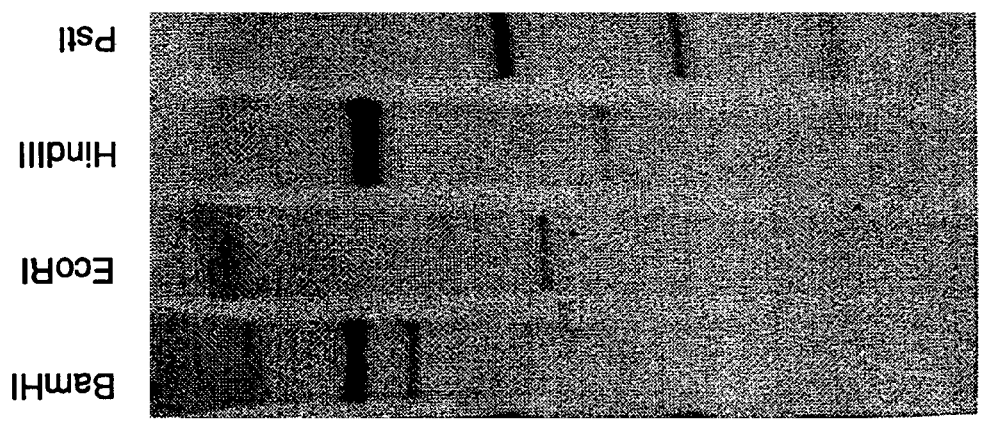

FIG. 2: Southern analysis of human genomic DNA (A) and P147 (B) restricted with Bam HI, EcoRI, HindIII and PstI endonuclease. Southern membranes from Pulsed-field electrophoretic gel profiles were probed with radioactively labelled PEDF cDNA. The pattern of hybridization of P147 DNA is consistent with total human genomic DNA. Size markers are indicated.

FIG. 3: 5' Flanking region of the PEDF gene. The human full length genomic PEDF sequence is represented by SEQ ID NO: 43. The first exon (capital letters) and the first 1050 bp of 5 prime flanking region are shown. Two Alu repetitive sequences are underlined. Possible binding sites for HNF-1, PEA3, Octomer (Oct), c/EBP are underlined and labeled. The putative AP-1 sites are shown in bold, and TREp/RAR are double underlined. The underlined (dashed) sequence in exon 1 was determined by the 5' race.

Figure 4C:
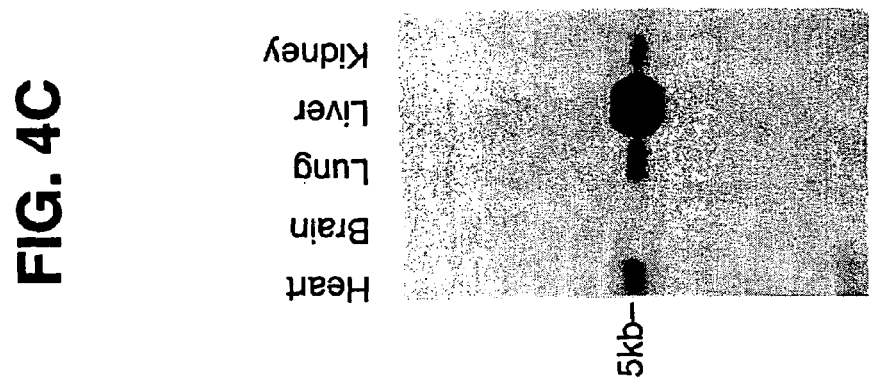
Figure 4B:
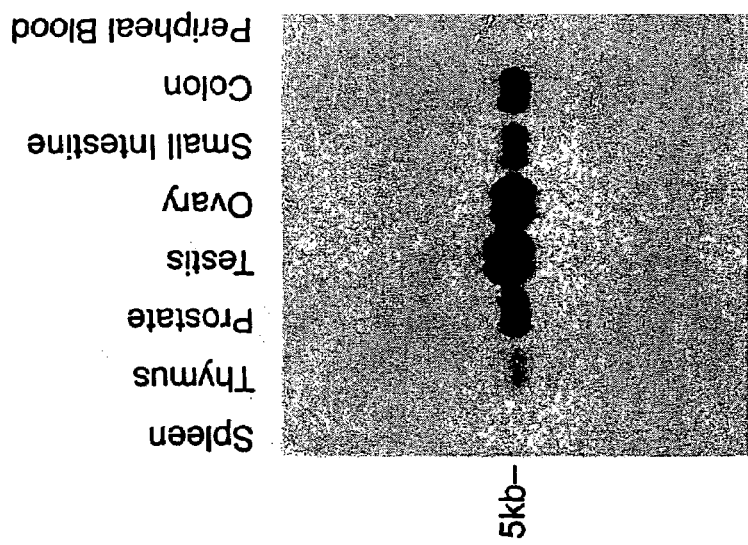
Figure 4A:
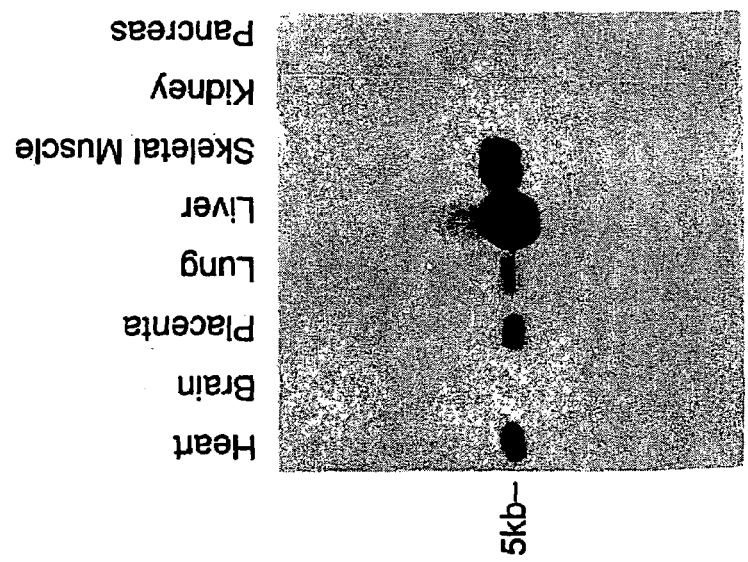

FIG. 4: Northern Blot analysis of PEDF mRNA: Gene expression analysis of the human PEDF transcript in a number of human adult and fetal tissues. Tissues from which RNA was obtained are shown above corresponding lanes. Membranes contain 2 ug poly (A) RNA for each sample and were probed with radioactively labelled cDNA for human PEDF. A single 1.5 kb transcript is seen in both adult and fetal tissues with the greatest intensity of hybridization in liver, testis, skeletal muscle and ovary while the signal for brain, pancreas and thymus was significantly weaker than that for other tissues. No significant signal was detected for adult kidney and spleen. A significant difference in PEDF mRNA levels seen between adult and fetal kidney.

Figure 5C:
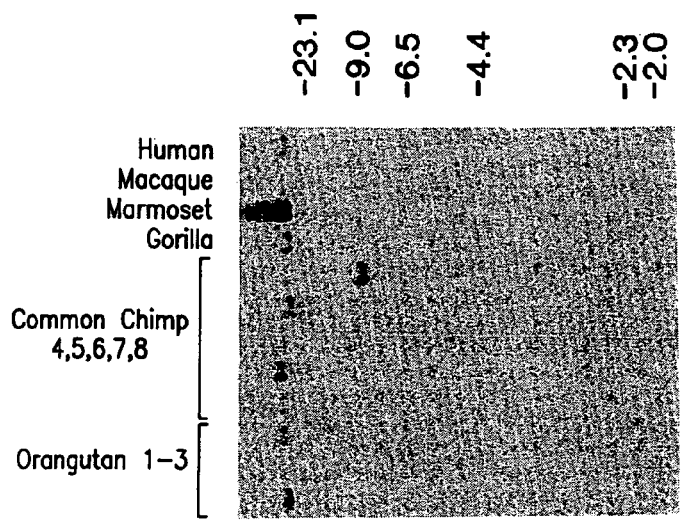

FIG. 5: Evolutionary relatedness of the Human PEDF gene: Each lane represents a total of 8 ug of genomic DNA for each species digested with Eco RI. Southern blot analysis is shown with a PEDF probe. Hybridization signals for chicken (A), mammals (B) and primates (C) is shown. A large fragment of approximately 23 kb is seen in all primates and many mammalian species. In addition several polymorphisms are seen in the different mammalian species examined.

Figure 6A:
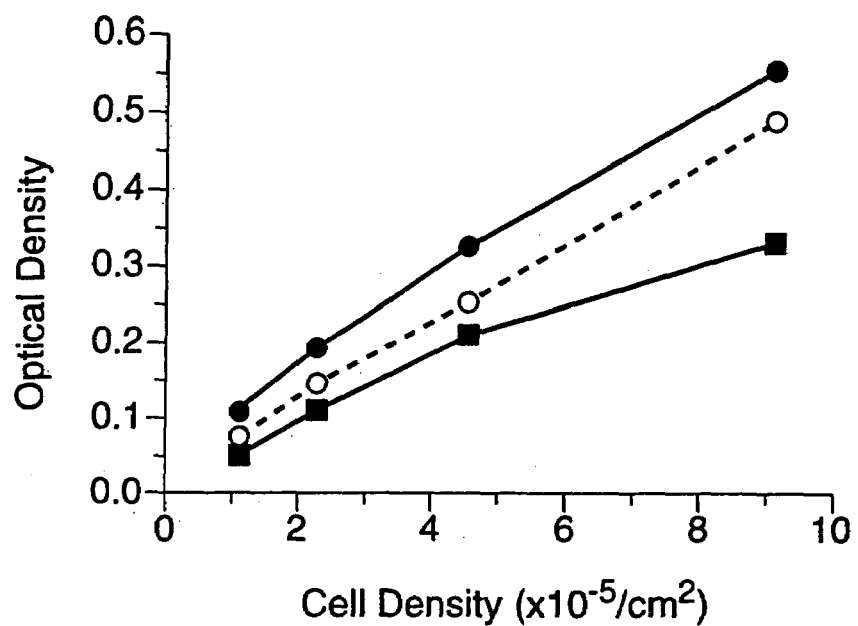
Figure 6B:
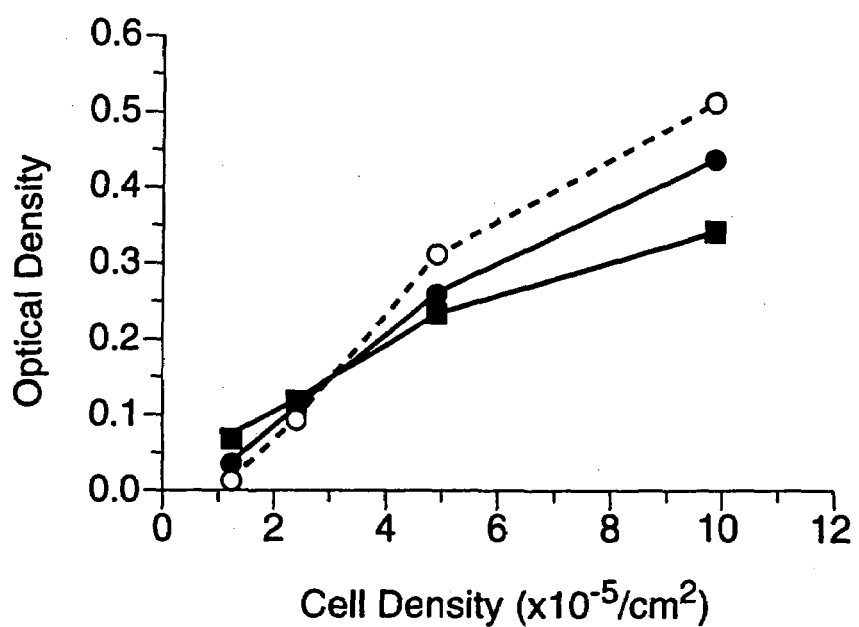

FIGS. 6A & 6B: Relationship between cell density plated and optical density measured by MTS assay. Different concentrations of postnatal-day 8 cerebellar granule cells were added to 96 well plate and cultured in serum-containing medium (6A), or chemically defined medium (6B). Optical density was measured on days in vitro (DIV) 1, 4, or 7. Square, DIV 1; Solid circle, DIV 4; Open circle, DIV7. The data are plotted as function of cell density (n=6).

Figure 7:
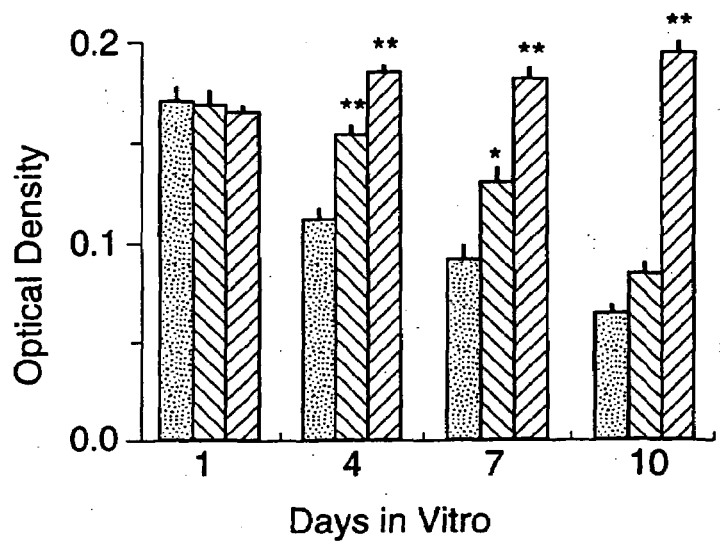

FIG. 7: Time course for PEDF stimulation of cell survival in chemically-defined medium. Postnatal-day 8 cerebellar granule cells were cultured in 96 well plate. PEDF was added at DIV 0 and the optical density was then measured on DIV 1, 4, 7, or 10. Solid bar, control; cross-hatched bar, PEDF treated (50 ng/ml); striped bar, PEDF treated (500 ng/ml). The data are expressed as optical density/well (means±SEM, n=6). Statistical analysis was done by two way ANOVA post-hoc Scheefe test. **$P<0.0001$ versus control.

Figure 8:
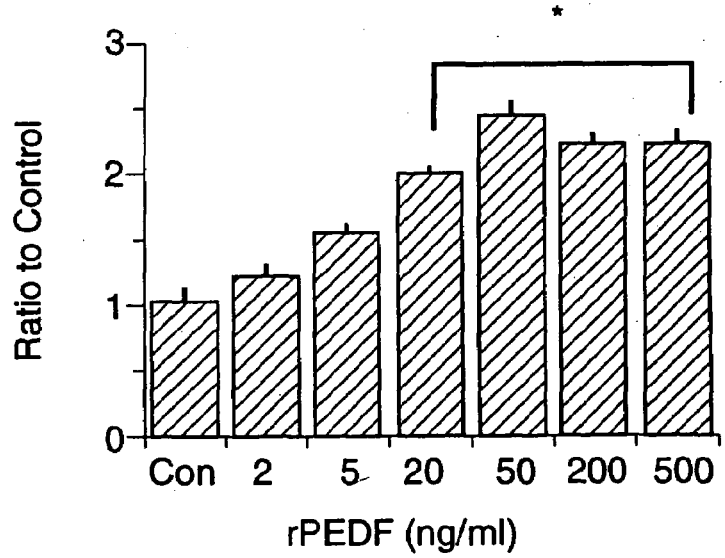

FIG. 8: Dose-response curve for PEDF in chemically defined medium. Different concentrations of PEDF were added on DIV 0 and MTS assay was carried out on DIV 7. The data are expressed as ratio to control (mean±SEM, n=6). Statistical analysis was done by one way ANOVA post-hoc Scheffe F test. **$P<0.0001$ vesus control.

Figure 9:
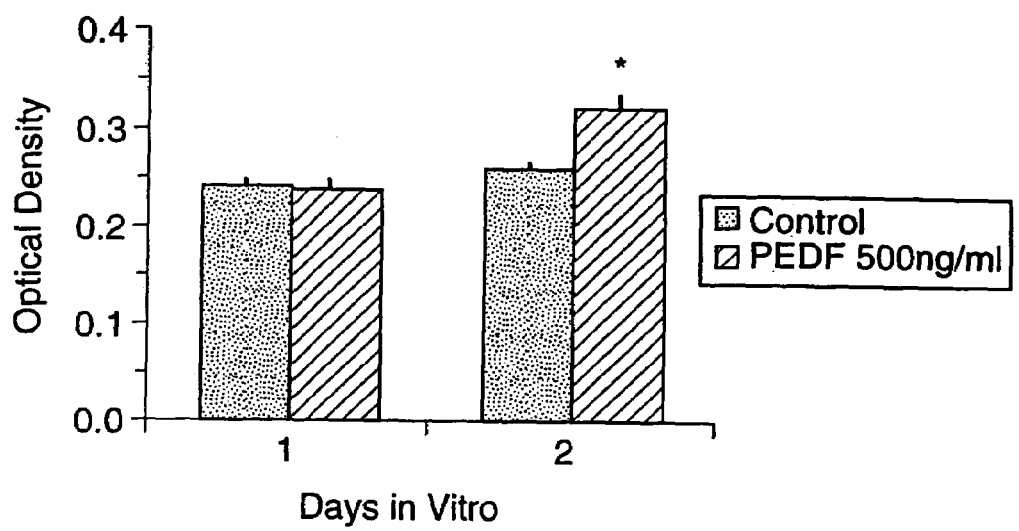

FIG. 9: MTS assay of postnatal day 5 cerebellar granule cells at DIV 1 and DIV 2. Postnatal-day 5 cerebellar granule cells were cultured in 96 well plate using serum-containing medium without Ara-C (A), or chemically defined medium without F12(B). The MTS assay was carried out on DIV 1 and 2. Solid bar, control; Striped bar, PEDF treated (500 ng/ml). The data are expressed as optical density/well (means±SEM, n=6). Statistical analysis was done by two way ANOVA post-hoc Scheffe F test. **$Pc0.0005$ vesus control.

Figure 10:
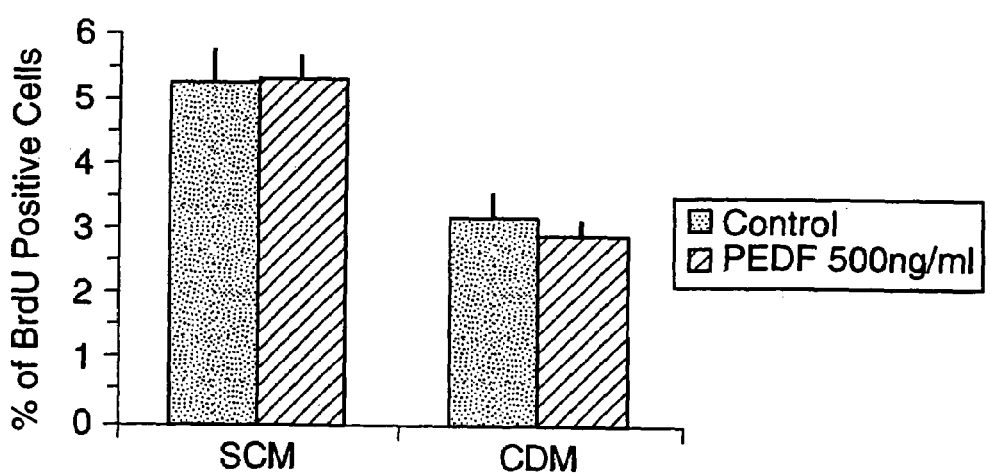

FIG. 10: BrdU incorporation into postnatal day 5 cerebellar granule cells. Postnatal-day 5 cerebellar granule cells were cultured in a 96 well plate using serum-containing medium (SCM) without Ara-C, or chemically defined medium (CDM) without F12. PEDF was added on DIV 0, BrdU was added on DIV 1 and the cells were fixed on DIV 2. Solid bar, control; Striped bar, PEDF treated (500 ng/ml).

The number of labeled nucleic acids are expressed as a percentage of total cell population (mean±SEM). For each value, 3000 cells was counted at least.

Figure 11:
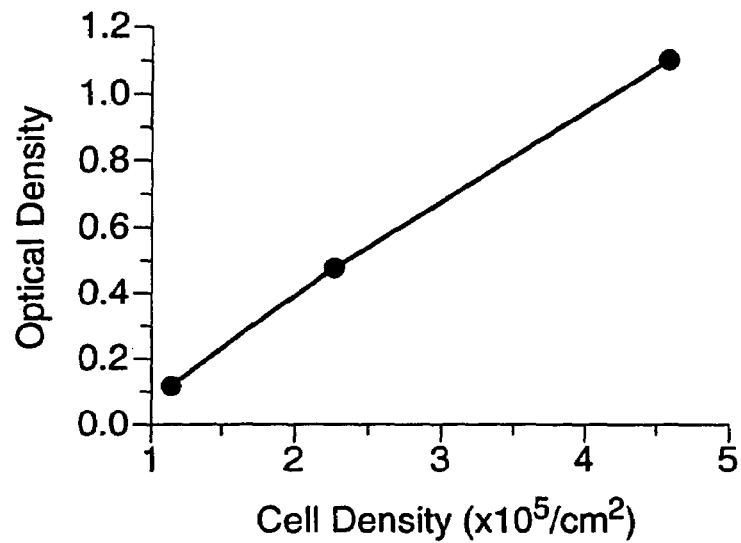

FIG. 11: Relationship between cell density and neurofilament content measured by ELISA. Different concentrations of postnatal-day 8 cerebellar granule cells are added to 96 wells and cultured. Optical density was measured on DIV 7. The data are plotted as a function of cell density.

Figure 12:
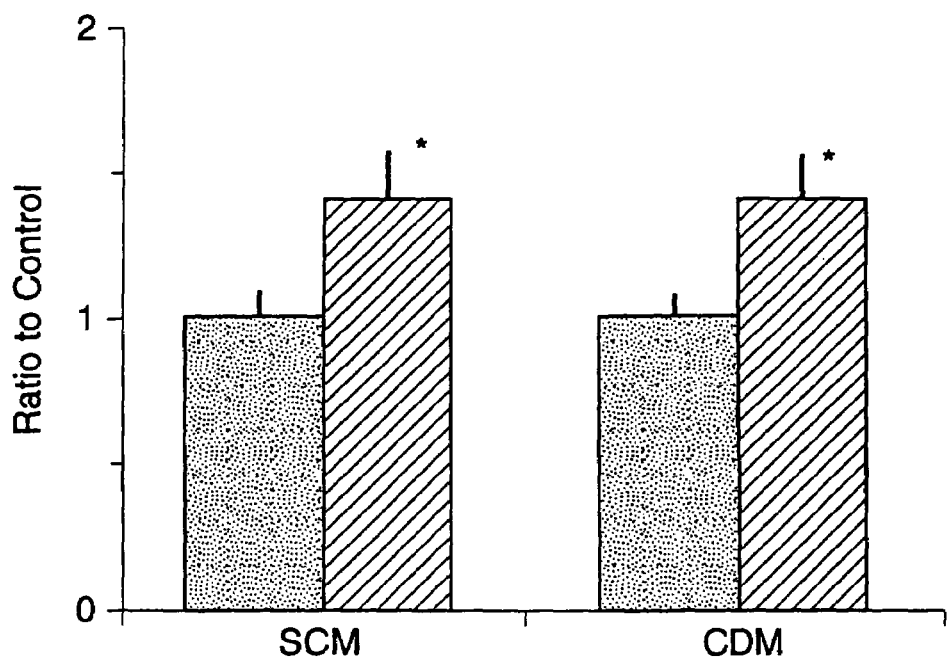

FIG. 12: Neurofilament ELISA assay in postnatal-day 8 cerebellar granule cells. Cells were cultured in a 96 well plate with or without PEDF using serum-containing medium (SCM) or chemically defined medium (CDM). After fixing cells on DIV 7, the neurofilament ELISA was carried out and the data are expressed as ratio to control (mean±SEM, n=6 to 10). Solid bar, control; Striped bar, PEDF treated (500 ng/ml). Statistical analysis was done by two way ANOVA post-hoc Scheffe F test. *P<0.05 vesus control.

Figure 13:
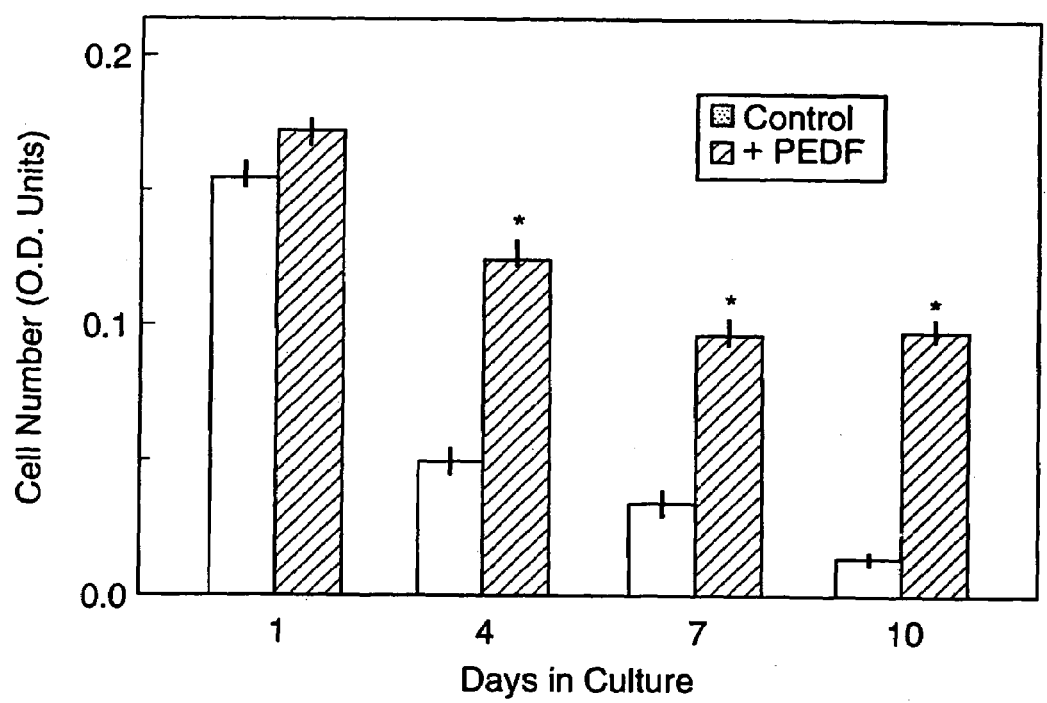

FIG. 13: Summary of PEDF neuronotrophic effects through 10 days in culture.

Figure 14:
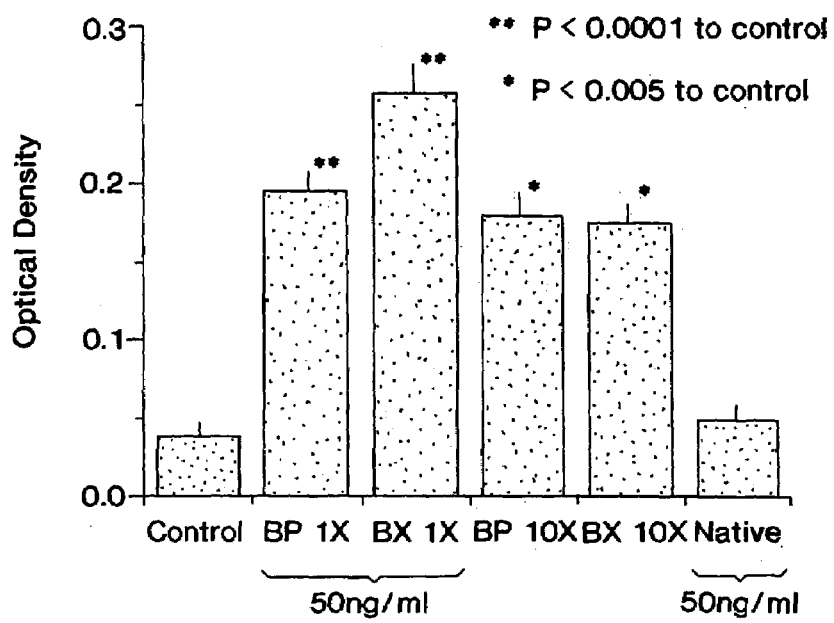

FIG. 14: Effects of truncated peptides BP and BX on CGC viability.

Figure 15:
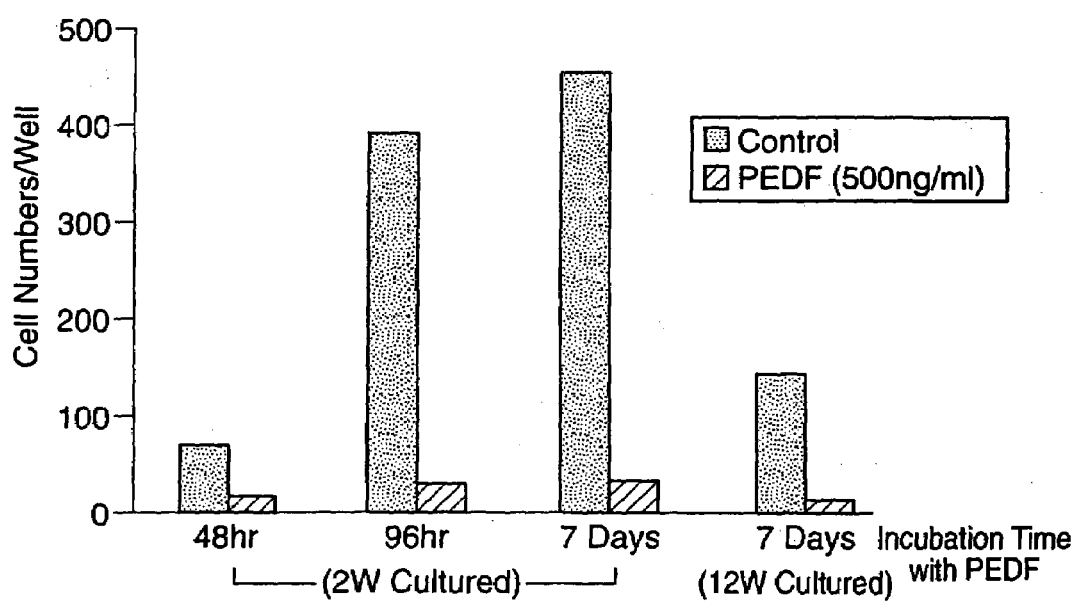

FIG. 15: Effect of PEDF on astroglia from cerebellum.

Figure 16:
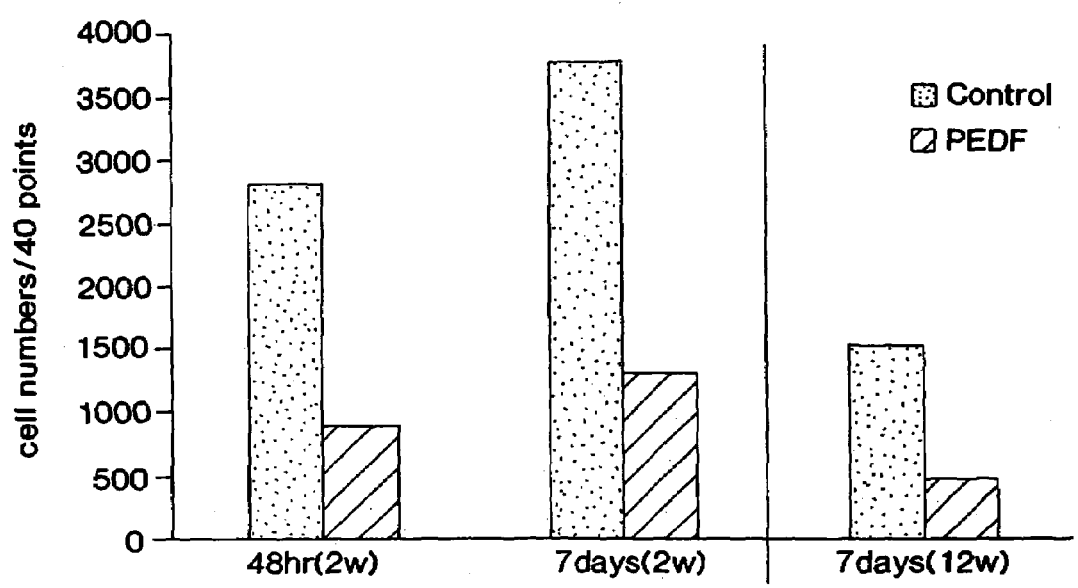

FIG. 16: Effect of PEDF on cerebellar microglia.

Figure 17A:
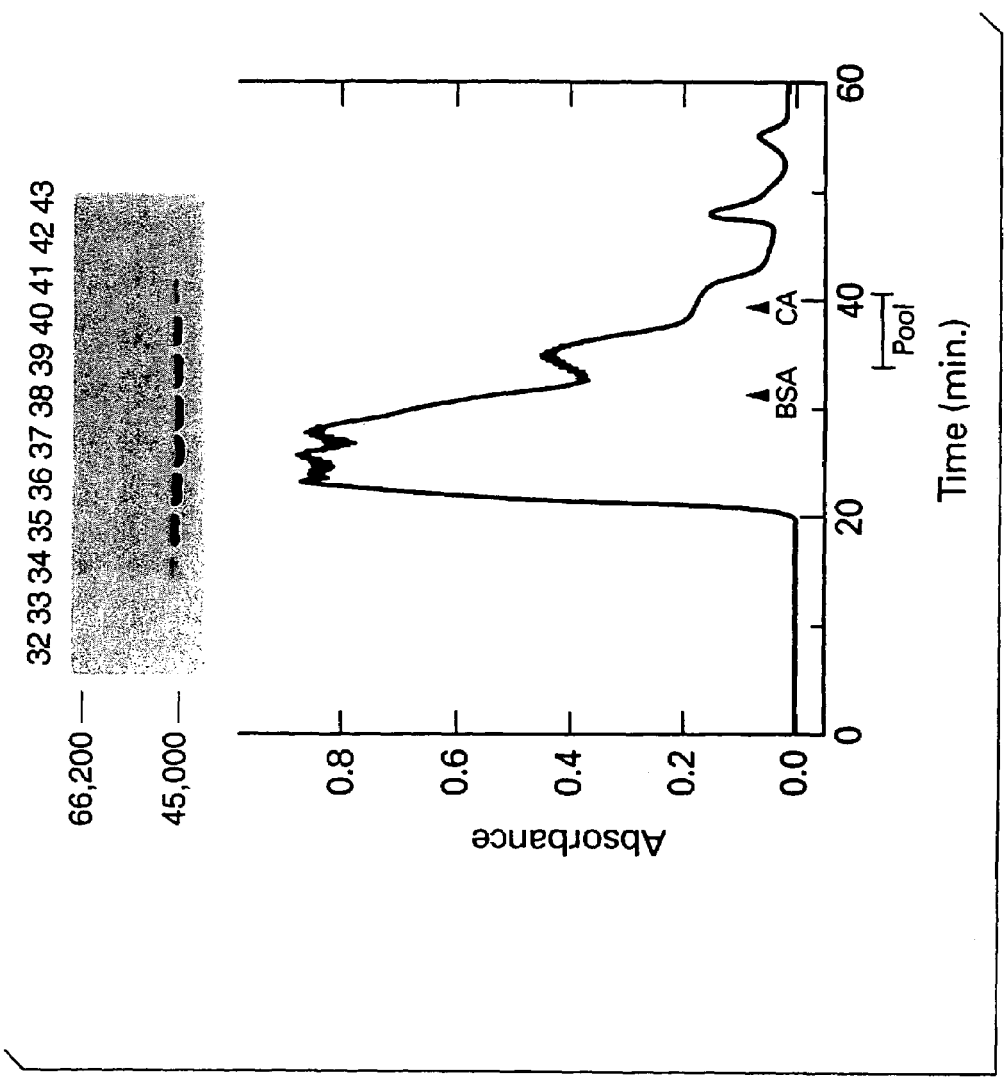
Figure 17B:
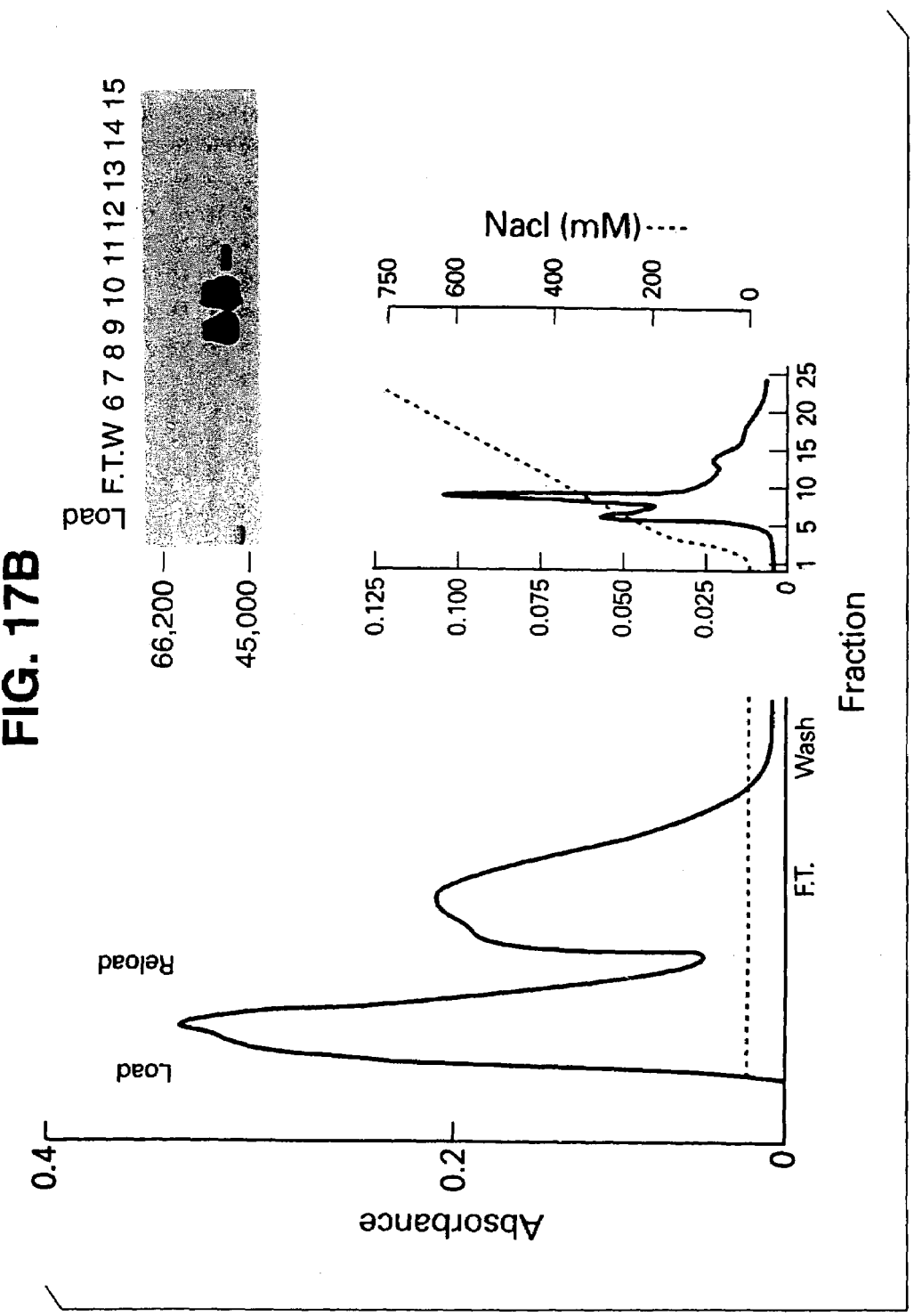

FIG. 17: Purification of PEDF-immunoreactive protein from bovine IPM. Washes of bovine IPM were subjected to A) TSK-3000 size-exclusion chromatography followed by B) Mono-S chromatography. Western blot inserts demonstrate the fractions containing PEDF.

Figure 18B:
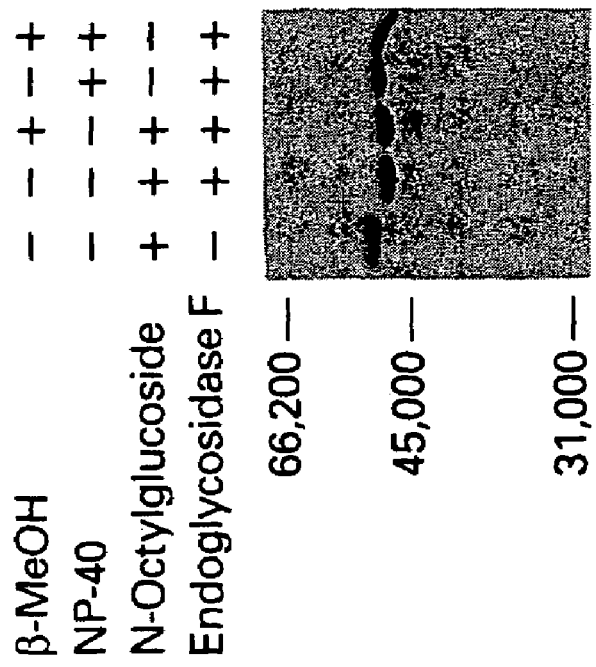
Figure 18A:
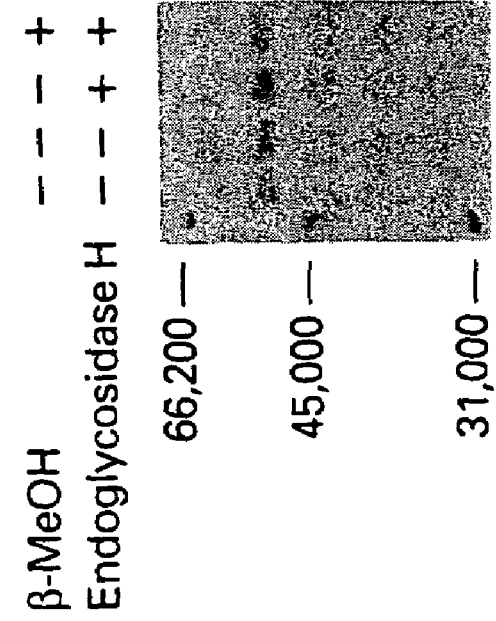

FIG. 18: Enzymatic deglycosylation of PEDF as demonstrated by Western blotting. PEDF treatment is given at the top of each lane. Numbers indicate positions of mol. wt. standards.

Figure 19B:
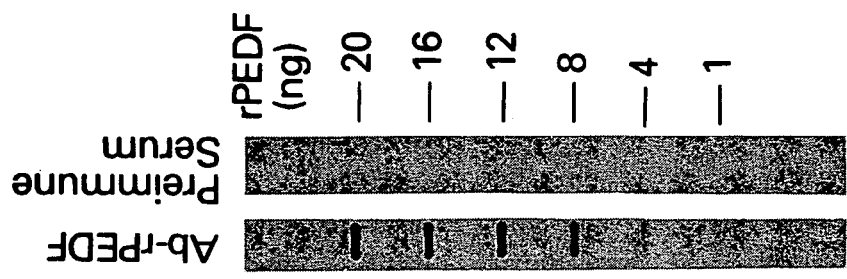
Figure 19A:
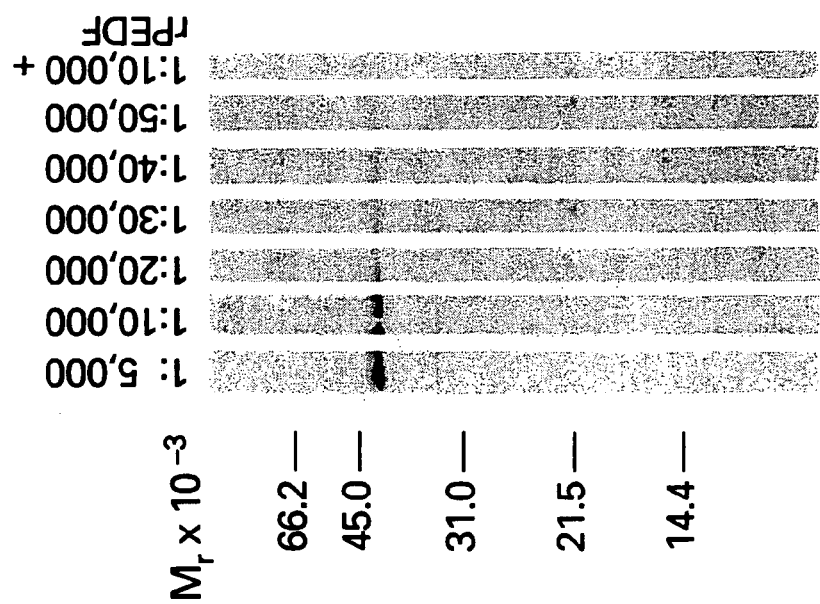

FIG. 19: Antibody to rPEDF specifically recognizes native PEDF at a high titer. A) Western blot demonstrating effectiveness of the antibody to at least 1:50,000 dilution and that addition of excess rPEDF completely blocks band visualization. B) Slot-blot analysis shows the ability to detect $\leq 1$ ng of native bovine PEDF protein.

Figure 20:
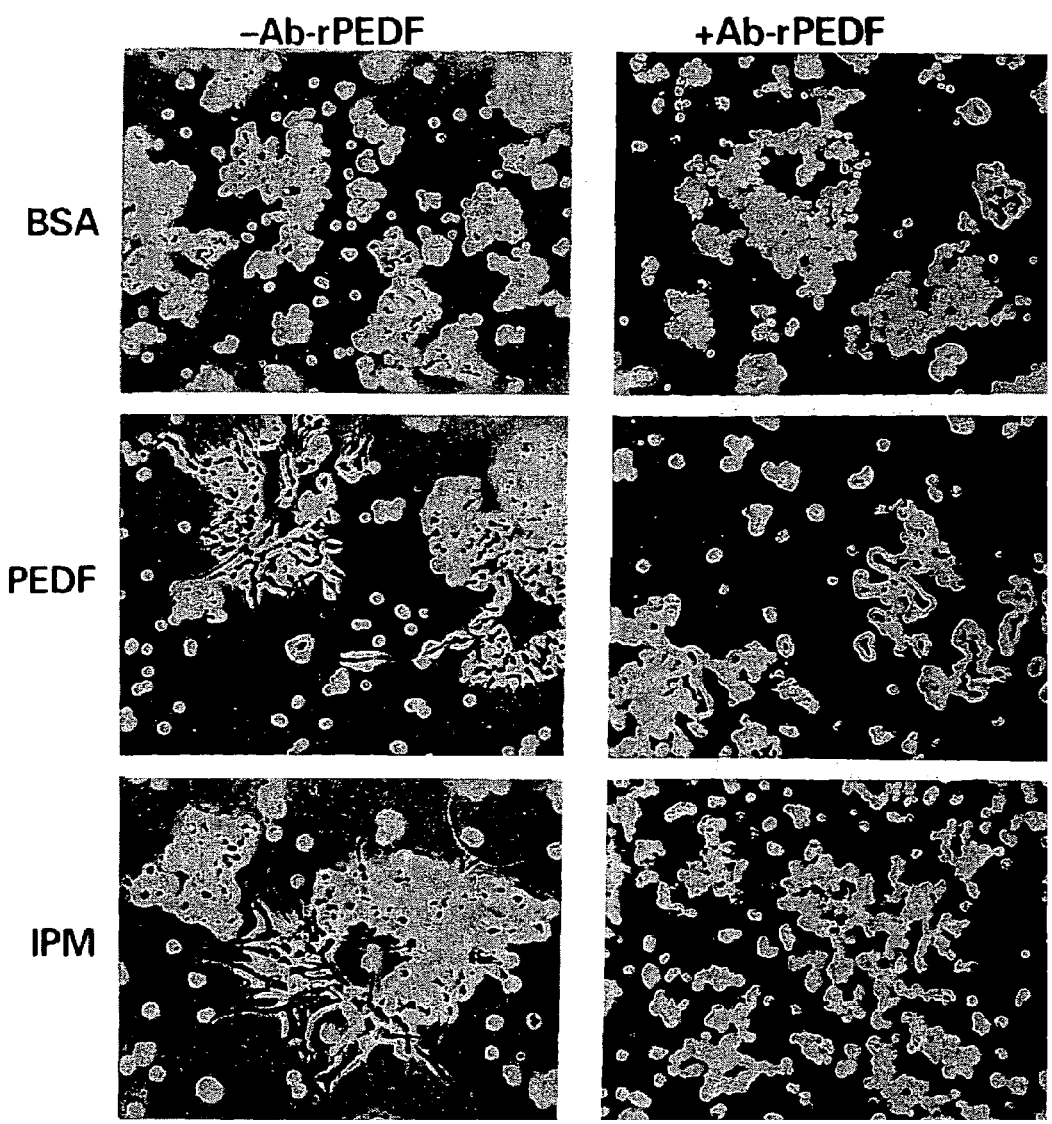

FIG. 20: Negative effect of PEDF antibody on neurite extension in Y-79 cells. Top row: bovine serum albumin (BSA) control cultures. Middle row: antibody effect on neurite-induction by native bovine PEDF protein. Bottom row: antibody effect on neurite induction by interphotoreceptor matrix (IPM).

Figure 21A:
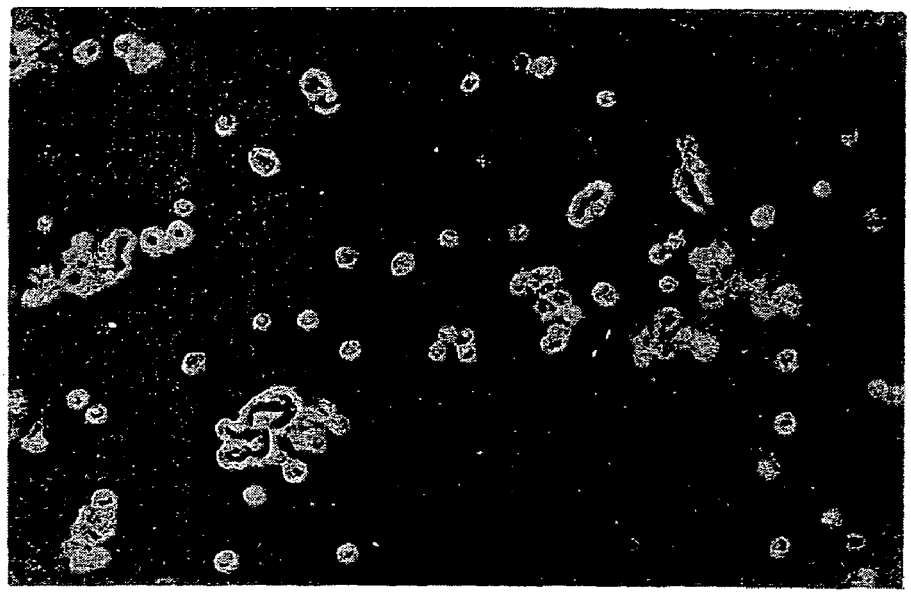
Figure 21B:
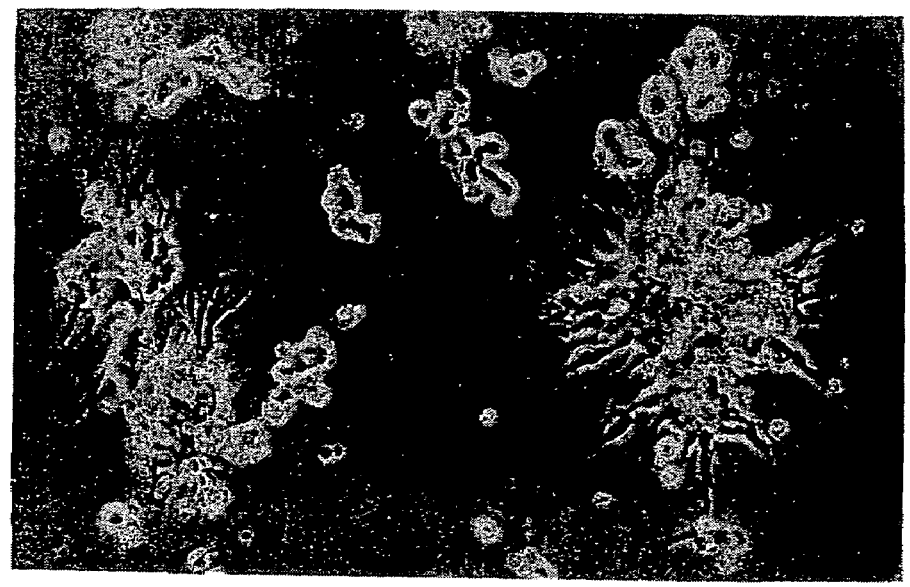

FIG. 21: Phase microscopy analysis of neurite outgrowth in the presence or absence of PEDF.

FIG. 22: Phase microscopy analysis of neurite outgrowth in the presence of recombinant PEDF and native, isolated PEDF.

Figure 23:
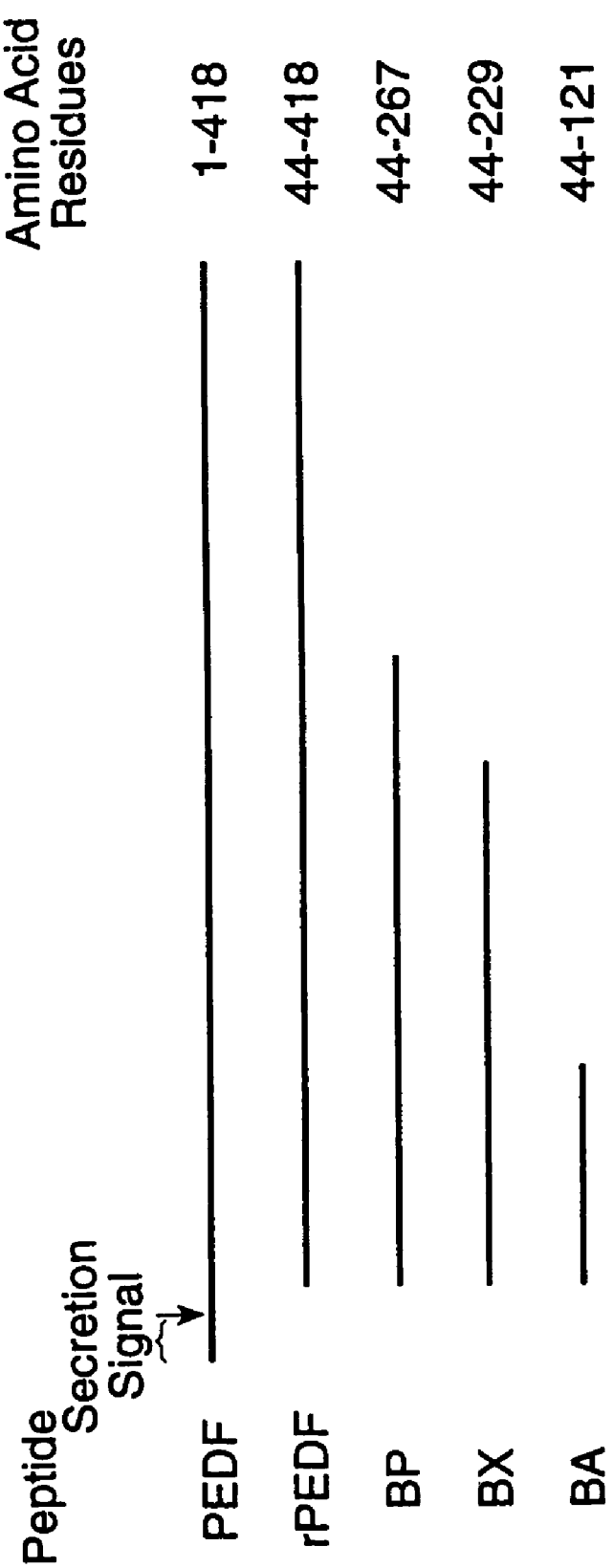

FIG. 23: Schematic Diagram of C-terminal deletions of rPEDF: PEDF is as shown in SEQ. ID NO: 2. rPEDF represents amino acids 44–418 of SEQ ID NO: 2. BP represents amino acids 44–267 of SEQ ID NO: 2. BX represents amino acids 44–229 of SEQ ID NO: 2. BA represents amino acids 44–121 of SEQ ID NO: 2.

DETAILED DESCRIPTION OF THE INVENTION

The present invention relates to a protein having novel, important and unobvious properties. Pigment epithelium-derived factor (PEDF) is a protein having neurotrophic, neuronotrophic and gliastatic characteristics. The present invention further relates to the DNA sequences coding for the PEDF gene, the genomic DNA containing the PEDF gene and fragments of the PEDF gene encoding for protein fragments of PEDF having biological activity.

"Neurotrophic" activity is defined herein as the ability to induce differentiation of a neuronal cell population. For example, PEDF's ability to induce differentiation in cultured retinoblastoma cells is considered neurotrophic activity.

"Neuronotrophic" activity is defined herein as the ability to enhance survival of neuronal cell populations. For example, PEDF's ability to act as a neuron survival factor on neuronal cells is neuronotrophic activity.

"Gliastatic" activity is defined herein as the ability to inhibit glial cell growth and proliferation. For example, PEDF's ability to prevent growth and/or proliferation of glial cells is gliastatic activity.

Based upon the protein amino acid sequence elucidated in the present invention, PEDF has been found to have extensive sequence homology with the serpin gene family, members of which are serine protease inhibitors. Many members of this family have a strictly conserved domain at the carboxyl terminus which serves as the reactive site of the protein. These proteins are thus thought to be derived from a common ancestral gene. However the developmental regulation differs greatly among members of the serpin gene family and many have deviated from the classical protease inhibitory activity (Bock (1990) Plenum Press, New York Bock, S.C., *Protein Eng.* 4, 107–108; Stein et al. (1989) *Biochem. J.* 262, 103–107). Although PEDF shares sequence homology with serpins, analysis of the cDNA sequence indicates that it lacks the conserved domain and thus may not function as a classical protease inhibitor.

Genomic sequencing and analysis of PEDF has provided sequences of introns and exons as well as approximately 4 kb of 5'-upstream sequence. The present invention demonstrates the localization of the gene for PEDF to 17p13.1 using both in situ hybridization and analyses of somatic cell hybrid panels (Tombran-Tink, et al., (1994) *Genomics*, 19:266–272). This is very close to the p53 tumor suppressor gene as well as to the chromosomal localization of a number of hereditary cancers unrelated to mutations in the p53 gene product. PEDF thus becomes a prime candidate gene for these cancers.

The full length human genomic PEDF sequence is represented by SEQ ID NO:43. The PEDF gene encompasses approximately 16 Kb and contains 8 exons all of which have conventional consensus splice-sites. The 5' flanking region of the PEDF gene contains two Alu repetitive elements which cover approximately two thirds of the first 1050 bp of the putative promoter sequence. There are also several sequence motifs which may be recognized by members of several families of transcription factors. The presence of two possible binding sites for the ubiquitous octamer family of transcription factors, may explain the presence of PEDF in most tissues tested. The presence of other more specific elements, however, suggests that PEDF is under precise control and supports previous work including its effects on such diverse processes as neuronal differentiation and fibroblast senescence.

The genomic PEDF sequence or fragments thereof are useful as a probe for detecting the gene in a cell. In addition, such a probe is useful in a kit for identification of a cell type carrying the gene. Mutations, deletions or other alternations in the gene organization can be detected through the use of a DNA probe derived from the PEDF genomic sequence.

Tissue Distribution

Although PEDF is particularly highly expressed by RPE cells, it is detectable in most tissues, cell types, tumors, etc. by Northern and Western blot analyses. It is readily detected, for example in vitreous and aqueous humors. The important question of subcellular localization of PEDF has also been addressed. Although the bulk of the PEDF appears to be secreted, we have used a PEDF antibody to probe cultured monkey RPE cells and found that PEDF is associated with the nucleus as well as with very specific cytoskeletal structures in the cytoplasm. Importantly, this varies as to the age of the cells and the specific cell-cycle state examined. For example, the protein appears to concentrate at the tips of the pseudopods of primate RPE cells that interact with the substratum during the initial stages of attachment. Later though, this staining disappears and there is appearance of the protein in association with specific cytoskeletal structures and the nucleus. Thus it appears that PEDF plays an important intracellular role in both nucleus and cytoplasm.

Involvement in Cell Cycle

The present invention indicates that there is expression in dividing, undifferentiated Y-79 cells and little or no expression in their quiescent, differentiated counterparts (Tombran-Tink, et al. (1994) *Genomics,* 19:266–272). Pignolo et al. (1993) *J. Biol. Chem.,* 268:2949–295) have demonstrated that the synthesis of PEDF in WI-38 fibroblast cells is restricted to the $G_0$ stage of the cell cycle in young cells. Moreover, in old senescent cells, PEDF messenger RNA is absent.

Production of Recombinant PEDF

Segmentation of the PEDF polypeptide is basic to studies on structure-function. For this purpose, expression vectors containing fragments of PEDF coding sequences provide an excellent source for synthesizing and isolating different regions of the PEDF polypeptide. Expression of human fetal PEDF sequences was achieved with *E. coli* expression vectors and the human fetal PEDF cDNA. We have shown that the recombinant PEDF product (rPEDF) is a biologically-active neurotrophic factor and is obtained in yields on the order of 1.3 mg/g of wet *E. coli* cells. Truncated peptides can also be made from appropriate molecular biological constructs and expressed in *E. coli*. Using these products, we have evidence that two distinct regions on the PEDF primary structure can be distinguished: 1) an "active site" conferring neurotrophic activity on the molecule that is located within amino acid residues 44–121 near the N-terminal of the protein and 2) a region near the C-terminal with homology to a serpin exposed loop i.e., the "classical" serpin active site. These results suggest 1) that the overall native conformation of PEDF is not required for neurite outgrowth and 2) that inhibition of serine proteases can not account for the biological activity of PEDF. We now have a series of truncated rPEDF constructs that span the protein sequence and can pinpoint the specific neurotrophic "active site" near the N-terminal.

Characterization with a Highly Specific Polyclonal Antibody

Purified recombinant human PEDF was used to develop a polyclonal antibody ("Anti-rPEDF") that specifically blocks the PEDF-mediate neurotrophic activity. Furthermore, the anti-rPEDF completely blocks the IPM-induced neurotrophic activity.

Neuronotrophic Properties of PEDF

In addition to demonstrating that native PEDF and rPEDF are neurotrophic in the Y-79 and Weri tumor cell systems, the present invention determined whether PEDF had an effect on normal neurons in primary culture. For this purpose, studies were conducted using cultures of normal cerebellar granule cells (CGCs) prepared from the 8-day postnatal rat. Cells treated with rPEDF did not respond to treatment by exhibiting a more neuronal morphological appearance. However, PEDF had a large effect on granule cell survival. Since these cells are not tumorous or transformed cells, they have a finite life in culture, dying in about 21 days depending on the culture medium. PEDF-treated culture, however, contained up to 10-fold more cells after 10 days of culture in serum-free medium compared to non-treated culture (FIG. 4). These results were determined; 1) by direct microscopic observation and cell counting and 2) use of an MTS (tetrazolium/formazan) assay which determines live cell numbers (See example 11). Thus, PEDF has a dramatic effect on CNS neuron survival and should be added to the short list of newly-emerging "neuronotrophic" proteins.

In General Tissue Culture Research:

Two problems that generally plague any tissue culture experiment using neurons and glia is that the neurons tend to die quickly and that glia tend to overrun the culture dish. PEDF or its peptides can help in both regards. Thus, one commercial use of PEDF might be as a general culture medium additive when CNS cells are to be cultured.

In CNS Transplantation Studies:

It is thought that transplantation of neurons may cure certain pathologies. For example, in Parkinson's disease, transplantation of specific fetal brain cells into patients could alleviate or cure the problems associated with the disease. One of the major problems to contend with, though, would be to prolong the life of the transplanted cells and to keep them differentiated, e.g. secreting the proper substances, etc. Pretreatment of the cells with PEDF could aid in both of these areas. Similarly, transfection of either neurons or astroglia with the PEDF gene before implantation can be a long-term source of PEDF at the transplantation site.

There is much activity in attempts at transplantation of neural retina and photoreceptor cells to help cure blindness. Attempts to date have not been fruitful both due to non-differentiation and death of the grafts. Again, PEDF may help in both regards. Specifically, photoreceptor neurons to be transplanted can be pretreated with PEDF or the gene transfected into the cells before surgery. Alternatively, PEDF can be transfected at high levels into adjacent retinal pigment epithelial (RPE) cells where they can serve as a supranormal source of the protein. Several investigators have now shown that cultured RPE cells survive very well after transplantation into the interphotoreceptor space of test animals. Transfection of human RPE cells in vitro with the PEDF gene then use of them in retinal transplantation thus is feasible.

In Neurodegenerative Diseases:

Many neurodegenerative diseases and other insults to the CNS (brain and retina) are typified by death of neurons and overpopulation by glia (gliosis). PEDF can be used effectively in these conditions to prolong the life and functioning of the primary neurons and to stave off the glial advance. PEDF can be effective, for example, in blocking microglial activation in response to CNS injury as well as prolonging/sparing the lives of neurons.

In the retina, it is predictable that PEDF inhibits the Muller glial cells. Since Muller cells are similar to astroglia, PEDF would be similarly effective in blocking gliosis in conditions such as retinal detachment, diabetes, Retinitis Pigmentosa, etc. as well as sparing the lives of the retinal neurons.

In Glial Cancers:

Most of the major forms of cancer that strike the CNS involve glial elements, PEDF is a gliastatic factor that can be used in combination with other forms of therapy. For example, along with surgery, PEDF can effectively inhibit the spread or reoccurrence of the disease.

Genetic Analysis

The present invention relates to the determination of the organization of the human PEDF gene and its promoter and analysis of its evolutionary relatedness and expression in a variety of human fetal and adult tissues.

The present invention provides, among other things, a nucleic acid which encodes PEDF. In particular, a human cDNA sequence is provided as set forth in SEQ ID NO:1. This cDNA sequence codes for PEDF, which has the amino acid sequence set forth in SEQ ID NO:2. Further genomic sequences are mapped in FIG. 1 and provided SEQ ID NO:43. Additional fragments of the genomic PEDF sequence are provided in SEQ ID NO: 9 through SEQ ID NO: 12. The location of intron-exon junctions are identified in table 1 and SEQ ID NO: 25 through SEQ ID NO: 40 and SEQ ID NO:43.

The term "nucleic acid" refers to a polymer of deoxyribonucleic acid (DNA) or ribonucleic acid (RNA), which can be derived from any source, can be single- or double-stranded, and can optionally contain synthetic, non-natural, or altered nucleotide which are capable of being incorporated into DNA or RNA polymers. The nucleic acid of the present invention is preferably a segment of DNA.

The present invention further provides truncated versions of PEDF. The largest of these is referred to as rPEDF, and comprises the amino acid sequence Met-Asn-Arg-Ile fused to $Asp^{44}$ . . . $Pro^{418}$ of PEDF, the amino terminus of which has been deleted. The rPEDF protein comprises the amino acid sequence of SEQ ID NO:3. The present invention also provides a nucleic acid which encodes a protein comprising the amino acid sequence of rPEDF, i.e., the amino acid sequence of SEQ ID NO:3.

One who is skilled in the art will appreciate that more than one nucleic acid may encode any given protein in view of the degeneracy of the genetic code and the allowance of exceptions to classical base pairing in the third position of the codon, as given by the so-called "Wobble rules". Accordingly, it is intended that the present invention encompass all nucleic acids that encode the amino acid sequences of SEQ ID NO:2 and SEQ ID NO:3, as well as equivalent proteins. The phrase "equivalent nucleic acids" is intended to encompass all of these nucleic acids.

It also will be appreciated by one skilled in the art that amino acid sequences may be altered without adversely affecting the function of a particular protein. In fact, some alterations in amino acid sequence may result in a protein with improved characteristics. The determination of which amino acids may be altered without adversely affecting the function of a protein is well within the ordinary skill in the art. Moreover, proteins that include more or less amino acids can result in proteins that are functionally equivalent. Accordingly, it is intended that the present invention encompass all amino acid sequences that result in PEDF protein or functional protein fragments thereof.

Some examples of possible equivalent nucleic acids and equivalent proteins include nucleic acids with substitutions, additions, or deletions which direct the synthesis of the rPEDF protein and equivalent protein fragments thereof; nucleic acids with different regulatory sequences that direct the production of rPEDF proteins; variants of rPEDF which possess different amino acids and/or a number of amino acids other than four fused to the amino terminal end of the protein; and PEDF and rPEDF and functional protein fragments thereof with amino acid substitutions, additions, deletions, modifications, and/or posttranslational modifications, such as glycosylations, that do not adversely affect activity. Since the neurotrophic activity has been correlated to a particular portion of the PEDF protein fragments containing these residues are clearly within the scope of the present invention.

The present invention also provides a vector which comprises a nucleic acid of SEQ ID NO:1, a nucleic acid which encodes a protein comprising the amino acid sequence of SEQ ID NO:2 or an equivalent protein, a nucleic acid which encodes a protein comprising the amino acid sequence of SEQ ID NO:3 or conservatively modified variant proteins, and conservatively modified variant nucleic acids thereof.

In particular, the present invention provides the vector πFS17, which comprises the nucleic acid of SEQ ID NO:1, and the vector pEV-BH, which comprises a nucleic acid which encodes a protein comprising the amino acid sequence of SEQ ID NO:3. It will be appreciated by those skilled in the art that the cDNA inserts described can be present in alternative vectors. For example, inserts can be in vectors of different nature, such as phages, viral capsids, plasmids, cosmids, phagemids, YACs, or even attached to the outside of a phage or viral capsid. The vectors can differ in host range, stability, replication, and maintenance. Moreover, the vectors can differ in the types of control exerted over cloned inserts. For example, vectors can place cloned inserts under the control of a different promoter, enhancer, or ribosome binding site, or even organize it as part of a transposon or mobile genetic element.

The present invention also provides a host cell into which a vector, which comprises a nucleic acid of SEQ ID NO:1, a nucleic acid which encodes a protein comprising the amino acid sequence of SEQ ID NO:2 or an equivalent protein, a nucleic acid which encodes a protein comprising the amino acid of SEQ ID NO:3 or an equivalent protein, or an equivalent nucleic acid thereof, has been introduced. In particular, the host cell may have the vector πFS17, which comprises the nucleic acid of SEQ ID NO:1, or the vector pEV-BH, which comprises a nucleic acid which encodes a protein comprising the amino acid sequence of SEQ ID NO:3.

The vectors of the present invention can be introduced into any suitable host cell, whether eukaryotic prokaryotic. These host cells may differ in their preferred conditions for growth, their nutritive requirements, and their sensitivity to environmental agents. Any appropriate means of introducing the vectors into the host cells may be employed. In the case of prokaryotic cells, vector introduction may be accomplished, for example, by electroporation, transformation, transduction, conjugation, or mobilization. For eukaryotic cells, vectors may be introduced through the use of, for example, electroporation, transfection, infection, DNA coated microprojectiles, or protoplast fusion.

The form of the introduced nucleic acid may vary with the method used to introduce the vector into a host cell. For example, the nucleic acid may be closed circular, nicked, or linearized, depending upon whether the vector is to be maintained as an autonomously replicating element, integrated as provirus or prophage, transiently transfected, transiently infected as with a replication-disabled virus or phage, or stably introduced through single or double crossover recombination events.

The present invention also provides a method of producing PEDF, rPEDF, and equivalent proteins, which method comprises expressing the protein in a host cell. For example, a host cell into which has been introduced a vector which comprises a nucleic acid of SEQ ID NO:1, a nucleic acid which encodes a protein comprising the amino acid sequence of SEQ ID NO:2 or an equivalent protein, a nucleic acid which encodes a protein comprising the amino acid of SEQ ID NO:3 or an equivalent protein, or an equivalent nucleic acid thereof, may be cultured under suitable conditions to produce the desired protein. In particular, a host cell into which has been introduced the vector πFS17, which comprises the nucleic acid of SEQ ID NO:1, or the vector pEV-BH, which comprises a nucleic acid which encodes a protein comprising the amino acid sequence of SEQ ID NO:3, may be cultured under suitable conditions to produce the proteins comprising the amino acid sequences of SEQ ID NO:2 and SEQ ID NO:3, respectively.

The present invention also provides recombinantly produced PEDF, and functional protein fragments thereof which have been produced in accordance with the aforementioned present inventive method of culturing an appropriate host cell to produce the desired protein. The production of a protein such as PEDF by recombinant means enables the obtention of large quantities of the protein in a highly purified state, free from any disease-causing agents which may accompany the protein isolated or purified from a naturally occurring source organism, and obviates the need to use, for example, fetal tissue as a source for such a protein.

Recombinant PEDF and functional protein fragments thereof may be supplied as active agents to cells by a variety of means, including, for example, the introduction of nucleic acids, such as DNA or RNA, which encode the protein and may be accordingly transcribed and/or translated within the host cell, the addition of exogenous protein, and other suitable means of administration as are known to those skilled in the art. In whatever form in which supplied, the active agent can be used either alone or in combination with other active agents, using pharmaceutical compositions and formulations of the active agent which are appropriate to the method of administration. Pharmaceutically acceptable excipients, i.e., vehicles, adjuvants, carriers or diluents, are well-known to those who are skilled in the art, and are readily available. The choice of excipient will be determined in part by the particular compound, as well as by the particular method used to administer the compound. Accordingly, there is a wide variety of suitable formulations which can be prepared in the context of the present invention. However, pharmaceutically acceptable excipients not altering the neurotrophic, neuronotrophic and gliastatic activities of the recombinant protein are preferred.

The following examples serve to illustrate further the present invention and are not to be construed as limiting its scope in any way.

EXAMPLE 1

This example describes the trypsin digestion of PEDF and the amino acid sequencing of the resulting fragments.

PEDF was purified from the medium of a primary culture of human fetal RPE cells by high performance liquid chromatography (HPLC). The HPLC-purified PEDF was then reduced and alkylated. Afterwards, it was dried and redissolved in 50 μl of CRA buffer (8 M urea, 0.4 M ammonium carbonate, pH 8.0), and 5 μl of 45 mM dithiothreitol (DTT) (Calbiochem, San Diego, Calif.) were added. After heating at 50° C. for 15 minutes, the solution was cooled, and 5 μl of 100 mM iodoacetic acid (Sigma Chem. Co., St. Louis, Mo.) were added. After 15 minutes, the solution was diluted to a concentration of 2 M urea and subjected to trypsin digestion (Boehringer-Mannheim, Indianapolis, Ind.) for 22 hours at 37° C. using an enzyme:substrate ratio of 1:25 (wt/wt). Tryptic peptides were separated by narrowbore, reverse-phase HPLC on a Hewlett-Packard 1090 HPLC, equipped with a 1040 diode array detector, using a Vydac 2.1 mm×150 mm C18 column. A gradient of 5% B at 0 minutes, 33% B at 63 minutes, 60% B at 95 minutes, and 80% B at 105 minutes, with a flow rate of 150 μl/minute, was used. In this gradient, buffer A was 0.06% trifluoroacetic acid/$H_2O$, and buffer B was 0.055% trifluoroacetic acid/acetonitrile. Chromatographic data at 210 and 277 nm, and UV spectra from 209 to 321 nm, of each peak were obtained. Samples for amino-terminal sequence analysis were applied to a polybrene precycled glass fiber filter and subjected to automated Edman degradation (Harvard Microchemical Facility, Boston, Mass.) on an ABI model 477A gas-phase protein sequencer (program NORMAL 1). The resulting phenylthiohydantoin amino acid fractions were manually identified using an on-line ABI Model 120A HPLC and Shimadzu CR4A integrator.

Trypsin digestion of purified PEDF and amino acid analysis of the resulting fragments yielded nonoverlapping peptide sequences, including the sequences JT-3 (SEQ ID NO:6):

```
Thr Ser Leu Glu Asp Phe Tyr Leu Asp Glu
 1               5                    10
Glu Arg Thr Val Arg Val Pro Met Met
                15
``` and JT-8 (SEQ ID NO:7):

```
Ala Leu Tyr Tyr Asp Leu Ile Ser Ser Pro
 1               5                    10
Asp Ile His Gly Thr Tyr Lys Glu Leu Leu
                15       20
Asp Thr Val Thr Ala Pro Gln Xaa Asn
                25
```

EXAMPLE 2

This example describes the construction of oligonucleotides, based on the peptide sequences of Example 1, the use of the oligonucleotides in the isolation of PEDF cDNA, and the sequencing of PEDF cDNA.

Based on the JT-3 and JT-8 peptide sequences of Example 1 and codon usage data, the oligonucleotides oFS5665 (SEQ ID NO:4): 5'-AGYAAYTTYTAYGAYCTSTA-3' and oFS5667 (SEQ ID NO:5): 5'-CTYTCYTCRTCSAGRT-ARAA-3' were constructed on an ABI 392 DNA/RNA Synthesizer and used as primers in a polymerase chain reaction (PCR).

A human fetal eye Charon BS cDNA library (obtained from Dr. A. Swaroop of the Kellog Eye Institute) was amplified once (Sambrook et al., *Molecular Cloning: A*

Laboratory Manual, 2nd ed., Cold Spring Harbor Press, Cold Spring Harbor, N.Y. (1989)) and screened by PCR (Friedman et al., Screening of λgt11 Libraries, In: *PCR Protocols: A Guide to Methods and Applications*, Innis et al., eds., Academic Press, NY (1990), pp. 253–260) using a Techne thermal cycler and standard reagents (GeneAMP, Perkin-Elmer Cetus), except that $MgSO_4$ was used at 3 mM. A PCR amplification fragment of about 350 bp was isolated on a 3% NuSieve 3:1 gel (FMC Biochemicals, Rockland, Me.) using NA-45 DEAE-cellulose paper (Schleicher and Scheull) (Sambrook et al., supra). The fragment was labeled with $\alpha^{32}P$-dCTP (Amersham Corp., Arlington Heights, Ill.) by random priming (Random Priming kit, Boehringer-Mannheim, Indianapolis, Ind.), and used to screen 200,000 plaque-forming units (PFUs) of the human fetal eye library.

Eight positive clones were isolated (Sambrook et al., supra), and DNA of the positive clones was purified according to Qiagen Maxi preparation protocols (Qiagen, Inc., Chatsworth, Calif.). The inserts of the positive clones were cut out with Not I (BRL, Gaithersburg, Md.), circularized with T4 DNA ligase (New England Biolabs, Beverly, Mass.), transformed into *Escherichia coli* Epicurian Sure competent cells (Stratagene, Inc., La Jolla, Calif.), and plated onto Luria broth (LB) plates containing ampicillin and 5-bromo-4-chloro-3-indolyl-β-D-galactoside (X-gal).

White colonies were selected on the basis that such colonies should possess an insert, and plasmid DNA from single colony cultures were isolated by the Qiagen plasmid miniprep protocol. Purified plasmids were digested with EcoR I and Hind III (BRL). These restriction sites were added during library construction through the ligation of linkers to the 5' and 3' ends of the insert, thus EcoR I–Hind III digestion excises the insert present in isolated plasmids. These fragments were electrophoresed on a 0.7% agarose gel to determine insert size. The plasmid possessing the largest insert, namely πFS17, was selected for mapping and subsequent sequencing using the Sequenase 2.0 sequencing kit (United States Biochemical Corp., Cleveland, Ohio) to confirm the identity of the clone. Sequence analysis was performed using the MacVector software package (International Biotechnologies, Inc.) and the GenBank® Sequence Data Bank (Intelligenetics, Mountain View, Calif.).

Sequence analysis of λFS17 revealed a base sequence comprising SEQ ID NO:1, with a long, open reading frame (ORF) encoding the 418 amino acids of SEQ ID NO:2, a typical ATG start codon, and a polyadenylation signal (not shown in SEQ ID NO:1). The coding sequence of the clone aligns exactly with all previously determined PEDF peptide sequences. The deduced amino acid sequence also contains a stretch of hydrophobic amino acids that could serve as a signal peptide. A comparison of the coding sequence and peptide sequence with the GenBank® Data Bank indicates that PEDF is a unique protein having significant homology to the serpin (serine protease inhibitor) gene family, which includes human [α]-1-antitrypsin. Although some of the members of this gene family exhibit neurotrophic activity (Monard et al. (1983) *Prog. Brain Res.*, 58, 359–364; Monard (1988) TINS, 11, 541–544), PEDF lacks homology to the proposed consensus sequence for the serpin reactive domain.

EXAMPLE 3

This example describes the construction of an expression vector for the production of recombinant PEDF.

An expression vector was constructed using the plasmid πFS17, which contains the full-length cDNA for human PEDF as described in Example 2. The PEDF coding sequence was placed under the control of a bacteriophage lambda $P_L$ promoter present in the plasmid pEV-vrf2 (Crowl et al., *Gene*, 38, 31–38 (1985)) to obtain the vector pEV-BH. This was accomplished by obtaining a BamH I–Hind III fragment of πFS17 comprising a portion of the PEDF coding region (namely, nucleotide 245 to 1490 of SEQ ID NO:1), digesting plasmid pEV-vrf2 with EcoR I–Hind III, rendering both fragments blunt by means of a fill-in reaction at the BamH I and EcoR I ends with DNA polymerase I (Klenow fragment), and ligating the resultant blunt-ended/compatible-ended fragments to each other. The resultant vector pEV-BH places a distance of 8 nucleotide between the Shine-Dalgarno (SD) sequence and the PEDF coding region. The construct specifies Met-Asn-Arg-Lle-Asp$^{44}$—Pro$^{418}$ such that a protein of 379 amino acids, known as rPEDF, is encoded as indicated in SEQ ID NO:3. The amino acids at the amino terminus of the rPEDF protein do not occur in native PEDF and result from the fusion of nucleic acids during the construction of pEV-BH.

To verify production of the recombinant PEDF protein by pEV-BH, the plasmid was propagated in *E. coli* strain RRI (Maniatis et al. (1982) *Molecular Cloning: A Laboratory Manual*, Cold Spring Harbor Laboratory, Cold Spring Harbor, N.Y.), bearing the low copy-number compatible plasmid pRK248cIts that contains a gene for encoding a temperature-sensitive λcIAt2 repressor (Bernard et al. (1979) *Methods in Enzymology*, 68, 482–492). Protein induction was performed as described in Becerra et al. (1991) *Biochem.*, 30, 11707–11719, with the following modifications. Bacterial cells containing pEV-BH were grown in LB medium containing 50 μg/ml ampicillin at 32° C. to early logarithmic phase, such that $OD_{600nm}=0.2$. The temperature of the culture was rapidly increased to 42° C. by incubating the flask in a 65° C. water bath, and the bacteria were subsequently grown at 42° C. for 2–3 hours in an air-flow incubator at 340 rpm. Aliquots were taken for absorbance readings at 600 nm.

Nascent proteins, synthesized following protein induction, were radiolabeled. After the temperature of the culture had reached 42° C., 150 μCi of L-[$^{35}$S]methionine (1040 Ci/mmol, Amersham Corp., Arlington Heights, Ill.) were added per ml of culture, and incubation was continued at 42° C. for 10 minutes and 30 minutes. Cells were harvested by centrifugation and washed with TEN buffer (10 mM Tris-HCl, pH 7.5, 1 mM EDTA, and 100 mM NaCl). $^{35}$S-labeled peptides from total bacterial extracts were resolved and analyzed on SDS-12% PAGE followed by fluorography. A band corresponding to a 42,820 $M_r$ polypeptide was detected 10 and 30 minutes post-induction. The size obtained for the recombinant protein expressed by pEV-BH matched the expected size for the coding sequence subcloned in pEV-BH. In a similar manner, smaller fragments (BP=28,000 $M_r$; BX=24,000 $M_r$; BA=9,000 $M_r$) can be synthesized and purified. BP peptide includes PEDF amino acids 44 through 269, BX peptide includes PEF amino acids 44 through 227, and BA peptide includes PEDF amino acids 44 through 121.

EXAMPLE 4

This example describes the construction of expression vectors containing the full-length PEDF cDNA.

In a manner similar to that described in Example 3 for the construction of pEV-BH, the PEDF ORF of plasmid πFS17 was placed under the control of the bacteriophage lambda $P_L$ promoter present in the plasmids pRC23 and pEV-vrf1

(Crowl et al. *Gene*, 38, 31–38 (1985)). This was accomplished by obtaining the SfaN I–Hind III fragment of πFS17 comprising a portion of the PEDF cDNA (namely, nucleotide 107 to 1490 of SEQ ID NO:1), digesting the plasmids with EcoR I–Hind III, rendering the fragments blunt by means of a fill-in reaction at the SfaN I and EcoR I ends with DNA polymerase I (Klenow fragment), and ligating the resultant blunt-ended/compatible-ended fragments to each other. The resulting vectors pRC-SH and pEV-SH place a distance of 14 and 8 nucleotide, respectively, between the SD sequence and the PEDF coding region. The construct pRC-SH encompasses the full-length PEDF ORF, and specifies a PEDF protein of 418 amino acids, with its naturally occurring amino terminus, as set forth in SEQ ID NO: 2. The construct pEV-SH encompasses the full-length PEDF ORF, and specifies a PEDF amino-terminal fusion protein of 425 amino acids, with Met-Asn-Glu-Leu-Gly-Pro-Arg (SEQ ID NO:8) preceding the PEDF sequence of SEQ ID NO:2. These additional amino acids at the amino terminus do not occur in native PEDF, and the codons in pEV-SH specifying these additional amino acids result from the fusion of nucleic acids during the construction of pEV-SH.

To verify production of the recombinant proteins specified by the two vectors, the vectors were introduced into *E. coli* strain RRI [pRK248cIts], and protein induction was performed and monitored by metabolic labeling with $^{35}$S-methionine during induction in a manner similar to that set forth in Example 3. The induced expression of the proteins specified by pRC-SH and pEV-SH had a negative effect on bacterial cell growth. In comparison with bacterial cultures containing the parental plasmids, cultures containing pRC-SH and pEV-SH grew and divided more slowly. This negative effect on bacterial growth correlated with the distance between the initiation codon and the SD, which may suggest that a shorter such distance results in more efficient translation of the recombinant protein. A 46,000 candidate polypeptide for PEDF was not detected in the media or cell lysates of bacterial cultures containing pRC-SH and pEV-SH. However, a 35,000 M protein was observed in extracts of cultures containing pRC-SH and pEV-SH, but not in extracts of cultures containing parental plasmids. This may indicate that the amino-terminal end of PEDF is protease-sensitive and that recombinant full-length PEDF is metabolized in this particular host. Alternatively, failure to observe the anticipated-sized recombinant PEDF proteins may reflect an experimental artifact which could be overcome through the use of alternative expression vectors, hosts, inducible promoters, subcloning sites, methods of recombinant protein isolation or detection, or means of protein induction.

EXAMPLE 5

This example describes a method for producing large quantities of recombinantly produced PEDF.

A total of 1 g of *E. coli* cells containing rPEDF was resuspended in 50 ml 20 mM Tris-HCl, pH 7.5, 20% sucrose, and 1 mM EDTA. The cells were maintained on ice for 10 minutes, sedimented by centrifugation at 4000×g, and were resuspended in 50 ml of ice-cold water for 10 minutes. Lysed outer cell walls were separated from spheroplasts by centrifugation at 8000×g.

The pelleted spheroplasts were resuspended in 10 ml of phosphate buffered saline (PBS) containing 5 mM EDTA, 1 µg/ml pepstatin and 20 µg/ml aprotinin. The suspension was probe-sonicated with a sonicator (Ultrasonics, Inc., model W-225) to lyse the cell membranes. Three bursts at 30 second pulses with a 30 second pause were performed while the sample was immersed in an ice-water bath. RNase TI (1300 units, BRL) and DNase I (500 µg, BRL) were added to the sonicated cell suspension, and the suspension was incubated at room temperature for 10 minutes. This suspension was diluted by the addition of 40 ml of phosphate buffered saline (PBS) containing 5 mM EDTA, 1 µg/ml pepstatin and 20 µg/ml aprotinin, and the crude inclusion bodies were sedimented by centrifugation at 13,000×g for 30 minutes. The particulate material consisting of inclusion bodies was resuspended in 40 ml of PBS containing 25% sucrose, 5 mM EDTA, and 1% Triton X-100, incubated on ice for 10 minutes, and centrifuged at 24,000×g for 10 minutes. The washing step was repeated three times. Finally, the inclusion bodies were resuspended in 10 ml of denaturation buffer containing 50 mM Tris-Cl, pH 8.0, 5 M guanidine-Cl, and 5 mM EDTA. The suspension was probe-sonicated briefly for 5 seconds in an ice-water bath. The resulting suspension was incubated on ice for an additional hour. After centrifugation at 12,000×g for 30 minutes, the supernatant was added to 100 ml of renaturation buffer containing 50 mM Tris-Cl, pH 8.0, 20% glycerol, 1 mM DTT, 1 µg/ml pepstatin, and 20 µg/ml aprotinin, and stirred gently at 4° C. overnight to renature the protein. The soluble and insoluble fractions were separated by centrifugation at 13,500×g for 30 minutes.

The soluble fraction was further purified by concentrating it to 1 ml using a Centricon 30 microconcentrator (Amicon Div., W. R. Grace & Co., Beverly, Mass.), and dialyzing it against Buffer A (50 mM sodium phosphate, 1 mM DTT, 20% glycerol, 1 mM EDTA, 1 µg/ml pepstatin, and 1 mM benzamidine) at 4° C. for 3 hours. The dialyzed extract was centrifuged at 14,000 rpm in an Eppendorf Centrifuge (Model 5415C) for ten minutes. The supernatant fraction was layered on a S-Sepharose fast-flow (Pharmacia, New Market, N.J.) column (1 ml bed volume) pre-equilibrated with buffer A. The column was washed with two column-volumes of buffer A. Finally, recombinant rPEDF was eluted with a step gradient of 50, 100, 150, 200, 300, 400, 500, and 1000 mM NaCl in buffer A. Fractions of 1 ml were collected by gravity flow, and were dialyzed against buffer A. Fraction 300, containing recombinant rPEDF, was stored at −20° C. The recovery in fraction 300 was 50 µg per gram of packed cells, which represents 25% of the total protein.

Most of the rPEDF was recovered from the insoluble fraction by dissolving the fraction in 10 ml of 6M guanidinium-Cl in buffer B (50 mM Tris-Cl, pH 8.0, 1 mM DTT, 2 mM EDTA). The solution was centrifuged at 10,000×g for 5 minutes. The supernatant was layered onto a Superose-12 (Pharmacia, New Market, N.J.) column attached in tandem to a second Superose-12 column (each column 2.6 cm×95 cm) pre-equilibrated with buffer containing 4 M guanidinium-Cl in buffer B. The flow rate was 3 ml/minute. Recombinant rPEDF containing fractions from the Superose-12 column were pooled and dialyzed against buffer C (4 M urea, 50 mM sodium phosphate, pH 6.5, 1 mM benzamidine, 1 µg/ml pepstatin, 4 mM EDTA). The dialyzed fraction was passed through a 0.22 µm filter (Miller-GV, Millipore Corp., Bedford, Mass.). The filtered solution was layered onto a mono-S (Pharmacia, New Market, N.J.) column (1 cm×10 cm, d×h) pre-equilibrated with buffer C. The column was washed with buffer C, and recombinant rPEDF was eluted with a gradient of 0 mM–500 mM NaCl in buffer C at 0.5 ml/min. Two-ml fractions were collected, and the peak fractions of recombinant rPEDF were pooled. The recovery in the pooled fractions was 0.5 mg of recombinant PEDF per gram of packed cells.

EXAMPLE 6

This example describes the use of purified recombinant PEDF as a differentiation agent.

Y79 cells (ATCC, HTB18) were grown in Eagle's Minimal Essential Medium with Earl's salts (MEM) supplemented with 15% fetal bovine serum and antibiotics (10,000 u/ml penicillin and 10 mg/ml streptomycin) at 37° C. in a humidified incubator under 5% $CO_2$. Cells were propagated for two passages after receipt from the ATCC, and then frozen in the same medium containing 10% DMSO. A few of the frozen aliquots were used for each differentiation experiment. All experiments were performed in duplicate.

After thawing, the cells were kept, without further passaging, in the serum-containing medium until the appropriate number of cells were available. Cells were collected by centrifugation and washed twofold in PBS, resuspended in PBS, and counted. At that point, $2.5 \times 10^5$ cells were plated into each well of a 6-well plate (Nunc, Inc., Roskilde, Denmark) with 2 ml of serum-free medium (MEM, supplemented with 1 mM sodium pyruvate, 10 mM HEPES, 1× non-essential amino acids, 1 mM L-glutamine, 0.1% ITS mix (5 µg/ml insulin, 5 µg/ml transferrin, 5 ng/ml selenium, Collaborative Research, Bedford, Mass.), and antibiotics as described above.

Differentiation effectors and control buffers were added 12–16 hours after plating, and the cultures were incubated and left undisturbed for 7 days. On the eighth day, cells were transferred to poly-D-lysine-coated six-well plates (Collaborative Research, Bedford, Mass.), and the old medium was replaced with 2 ml of fresh serum-free medium, upon attachment of the cells to the substrate. The cultures were maintained under these conditions for up to 11 days. Post-attachment cultures were examined daily for morphological evidence of differentiation as well as quantification of neurite outgrowth using an Olympus CK2 phase-contrast microscope.

Figure 22A:
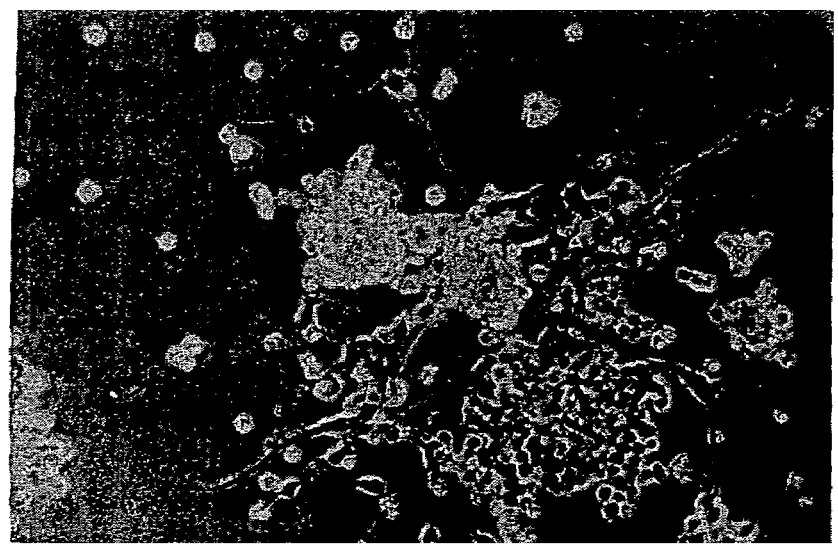
Figure 22B:
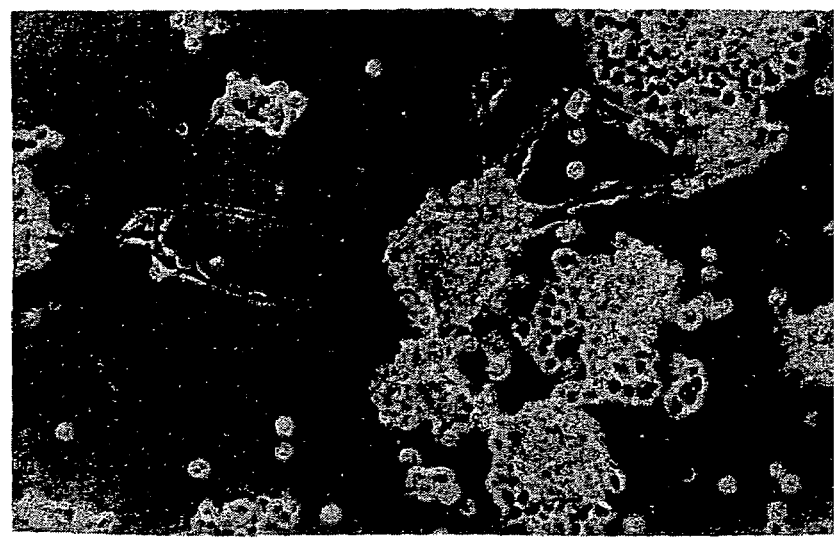

In comparison with untreated cells, only Y79 cultures that were exposed to recombinant rPEDF showed any significant evidence of neuronal differentiation. Some neurite outgrowth (below 5%) was detectable in control cultures treated with the same buffer used to solubilize rPEDF, and no evidence of differentiation was found in cultures processed in the same manner without the addition of rPEDF or buffer (FIG. 22A, "control"). Phase contrast microscopy of rPEDF treated cultures showed that between 50–65% of the cell aggregates had neurite extensions by day 3 post-attachment on poly-D-lysine (FIG. 22B, "PEDF"). These 3-day neurite extensions appeared as short projections from pear-shaped cells at the edges of the cell aggregates. The number of differentiating aggregates, the number of differentiating cells per aggregate, and the length of the neurite-like processes increased with post-attachment time.

By day 5 post-attachment, about 75–85% of the aggregates showed signs of differentiation with neurites extending from most of their peripheral cells. rPEDF-treated cultures reached the maximum extent of differentiation on day 7 post-attachment, when 85–95% of the cells aggregate. At that time, two types of neuronal processes were observed, i.e., single neurites 2–3 fold longer than those observed on day 3 extending from peripheral cells of isolated aggregates, and much longer and thinner processes forming a branching network between neighbor cell aggregates. Upon extended incubation, i.e., beyond 10 days post-attachment, there was a marked decrease in the proportion of the network connections, and no further growth of the single neurites, although the viability of the cell aggregates was not severely affected, and remained at about 75–80% in different experiments. No differences were observed between purified native PEDF and recombinant PEDF (rPEDF) as seen in FIG. 23.

The PEDF and rPEDF cDNA clones not only provide means to produce large quantities of the PEDF and rPEDF proteins but also serve as sources for probes that can be used to study the expression and regulation of the PEDF gene. In addition, these sequences can be used in the antisense technique of translation arrest to inhibit the translation of endogenous PEDF.

The recombinantly produced PEDF and rPEDF proteins and equivalent proteins can be used as potent neurotrophic agents in vitro and in vivo. Additional biochemical activities of these proteins as neurotrophic agents can be determined through standard in vitro tests, which will enable the development of other therapeutic uses for these proteins in the treatment of inflammatory, vascular, degenerative and dystrophic diseases of the retina. Given that these proteins are such potent neurotrophic agents, it can be envisioned that these proteins could be modified for therapeutic utility in the treatment of tissues other than the retina, which also respond to neurotrophic factors. These proteins may even find more generic utility as "differentiation" factors for non-neural tissues and certain types of cancer.

EXAMPLE 7

Along with the 3,000 mol. wt. recombinant PEDF, smaller recombinant constructs have been synthesized to determine if they have neurotrophic activity. Smaller peptides could offer a variety of advantages over the full-length construct such as greater solubility, better membrane penetration, less antigenicity, greater ease in preparation, etc.

FIG. 23 shows only three of the constructs that have been tested. BP, BX and BA are about 28,000, 24,000 and 9,000 mol. wts. respectively and represent C-terminal deletion mutants. All of these show neurotrophic activity similar to that depicted in FIGS. 21 and 22. The novel finding here is that even the 9,000 m.w. peptide (only about 20% of the full m.w. of the native protein) exhibits striking neurotrophic activity. Moreover, the active neurotrophic peptide represents sequences at the N-terminal rather than at the C-terminal which is known to contain the serpin active site. Thus, that the active site is at the N-terminal and activity can be elicited with such a small molecule are surprising findings that could not have been predicted based on any previous findings.

TABLE 1

Exon and Intron Organization of the human PEDF Gene

| Exon Number | Exon Size (bp.) | 5' Splice Donor | SEQ. ID. NO. | Intron Bize (Kb) |
|---|---|---|---|---|
| | | Promotor ...aaggagta | | |
| 1 | 128 | TATCCACAG/gtaaagtag... | 25 | 4806 bp |
| 2 | 92 | CCGGAGGAG/gtcagtagg... | 26 | 2862 bp |
| 3 | 199 | TCTCGCTGG/gtgagtgct... | 27 | 980 bp |
| 4 | 156 | TTGAGAAGA/gtgagtcgc... | 28 | 688 bp |
| 5 | 204 | ACTTCAAGG/gtgagcgcg... | 29 | 2982 bp |
| 6 | 143 | AGCTGCAAG/gtctgtggg... | 30 | 1342 bp |
| 7 | 211 | AGGAGATGA/gtatgtctg... | 31 | 444 bp |
| 8 | 377 | TTTATCCCT/aacttctgt... | 32 | |

TABLE 1-continued

Exon and Intron Organization of the human PEDF Gene

| 3' Splice Acceptor | SEQ. ID. NO. | Intron No. |
|---|---|---|
| GCTGTAATC | 33 | 1 |
| ...ttcttgcag/GCCCCAGGA | 34 | 2 |
| ...tcctgccag/GGCTCCCCA | 35 | 3 |
| ...ctctggcag/GAGCGGACG | 36 | 4 |
| ...tcttctcag/AGCTGCGCA | 37 | 5 |
| ...tcttttccag/GGCAGTGGG | 38 | 6 |
| ...ttgtctcag/ATTGCCCAG | 39 | 7 |
| ...tctctacag/AGCTGCAAT | 40 | 8 |

Table 1: Exons are in upper case and introns sequences in lower case. The 5' donor GT and 3' acceptor AG are underlined. Exon and intron sizes are given in bp and kb respectively.

EXAMPLE 8

Cloning and Sequencing of the Human PEDF Gene

Materials—Restriction enzymes, SuperScript® RT and Kanamycin were purchased from GIBCO-BRL (Gaithersburg, Md.). Dynabeads® Oligo dT$_{(25)}$ were purchased from Dynal Inc. (Lake Success, N.Y.). Retrotherm™ RT was obtained from Epicentre Technologies (Madison, Wis.). RNAsin® was purchased from Promega (Madison, Wis.). Taq polymerase was purchased from Perkin-Elmer (Norwalk, Conn.), or Stratagene (La Jolla, Calif.). The plasmid vector pBlueScript® used for subcloning was purchased from Stratagene (La Jolla, Calif.). Total RNA from neural retina and retinal pigment epithelium was purified from human tissue obtained from the National Disease Research Interchange (NDR1, Philadelphia, Pa.) as previously described (Chomczynki and Sacchi, 1987). [$^{32}$P]α-DATP and [$^{32}$P]γ-ATP (3000 Ci/mmol) used for labeling and sequencing (respectively) were purchased from Amersham) Arlington Hts, Ill.). Superbroth (Bacto-Tryptone 12 g/L, yeast extract 24 g/L, K$_2$HPO$_4$ 12.5 g/L, HK$_2$PO$_4$ 3.8 g/L and glycerol 5 mL/L), denaturing solution (0.2 N NaOH, 1.5 M NaCl), neutralizing solution (1 M Tris-Cl pH 7.0, 1.5 M NaCl), 20×SSC (3.0 M NaCl, 0.3 mM sodium citrate), 10×TBE (1 M Tris-borate, 2 mM EDTA, pH 8.3), and 50×TAE (2 M Tris-acetate 50 mM EDTA, pH 8.0) were purchased from Quality Biologicals (Gaithersburg, Md.). 20× SSPE (3M NaCl, 0.2 M NaH$_2$PO$_4$, 20 mM EDTA pH 7.4) was purchased from Digene Diagnostics, Inc. (Silver Spring, Md.). Ampicillin was purchased from Sigma Chemical Co. (St. Louis, Mo.) dissolved in water and filter-sterilized.

Polymerase chain reaction (PCR). A 2×PCR mix was prepared containing 1.6 μmoles/mL of GeneAmp® dNTPs (400 μM each), 2× GeneAmp® PCR buffer and 50 U/mL Taq polymerase. These reagents were purchased from Perkin-Elmer (Norwalk, Conn.). In general, the template and oligonucleotides (100 ng of each oligo) were mixed in 25 μL volume and 25 μL of the 2× mix were then added followed by 50 μL of mineral oil. The template was initially denatured for 2 min at 95° C., 30 sec annealing (temperature between 55 and 65° C. depending on the primers) and an extension at 72° C. for 1–5 min depending on the length of the product amplified.

cDNA synthesis on Dynabeads® oligo (dT)$_{25}$. The cDNA was synthesized on Dynabeads as previously described (Rodriguez and Chader 1992). The Dynabeads (0.5 mg) were washed with 100 μL of 10 mM Tris-Cl pH 7.0, 1 mM EDTA, 1 M KCl. The total RNA 30 μL, (30 μg, ~1 μL), in water was mixed with 30 μL of the above buffer and the equilibrated Dynabeads (0.5 mg) then heated to 55° C. for 2 minutes. The poly+ A RNA was allowed to anneal to the beads for 15 min at room temperature and the excess RNA removed by binding the beads for 15 min at room temperature and the excess RNA removed by binding the beads to the MPC-E magnetic separator (Dynal Inc.). The beads with the annealed poly+ A mRNA were then suspended in 2.5 μL buffer A (200 mM Tris-Cl pH 8.3, 1.0 M KCl), 2.5 μL buffer B (30 mM MgCl$_2$, 15 mM MnCl), 20 μL 10 mM dNTP's (2.5 mM each), 1 μL RNAsin, 2 μL SuperScript RT, 5 μL of Retrotherm RT (1 Unit/μl) and 16 μL of H$_2$O to make a final volume of 50 μL. The reaction mixture was incubated at 40° C. for 10 min, than at 65° C. for 1 hr. The beads were again bound to the MPC-E magnetic separator and the excess RT reaction mix removed. The beads were then washed once with 100 μL 0.2N NaOH, once with 10× SSPE, and twice in 1×TE. The cDNA-containing beads were suspended in a final volume of 100 μL 1×TE.

5' Rapid Amplification of cDNA Ends (RACE). The 5'-RACE was performed using a modified method based on the 5'-AmpliFINDER RACE kit purchased from Clontech (Rodriguez et al. 1994). First, cDNA was synthesized on Dynabeads® Oligo dT$_{(25)}$ as described above (Rodriguez and Chader, 1992). The AmpliFINDER anchor primer (Clontech) was ligated to the 3' ends tips of the Dynabead-immobilized retinal pigment epithelium cDNA using the same conditions as for soluble cDNA described in the 5'-AmpliFINDER RACE kit. The Ampli-FINDER anchor primer was used in combination with an PEDF-specific primer #2744 to PCR amplify the 5' prime end. The amplification was done as described above with 2 μL of anchor-ligated human retinal pigment epithelium-Dynabeads cDNA used as template. The amplification was performed for 30 cycles.

Sequence of oligonucleotides. Oligonucleotide primers were synthesized in an Applied Biosystems Inc. (Foster City, Calif.) DNA synthesizer model 392. The oligonucleotides were deprotected and used without further purification.

Screening of genomic libraries. The human genomic cosmid library (Clontech) was plated on LB plates containing 150 mg/mL ampicillin, 20 mg/mL Kanamycin at a density of 10,000 colonies per plate. Nitrocellulose filters were used to lift the colonies and the filters were treated and hybridized as described in Sambrook et al., (1989). The library was probed with [$^{32}$P]-labeled PCR product obtained from amplifying a PEDF cDNA clone (Steele et al. 1993) using T7/T3 primers. This resulted in the isolation of the p10A cosmid. A λDASH™II library (Stratagene) was screened by Lark Sequencing Technologies Inc. (Houston, Tex.) using the insert from the PEDF cDNA clone mentioned above. This resulted in the isolation of the 7 Kb NotI-Not fragment (JT6A). A P-1 clone, p147, containing the entire PEDF gene and flanking regions was isolated using oligos 1590/1591 by Genome Systems (St. Louis, Mo.).

Cloning of PCR products: Four sets of primers, 603:604; 605:606; 2238:354 and 2213:2744 designed from the internal coding regions of the PEDF cDNA sequenced were synthesized as decribed above for use as primers in a polymerase chain reaction (PCR) experiments. The primer sequences are as follows: 603: 5'-ACA AGC TGG CAG CGG CTG TC-3' (SEQ ID NO: 13), 604: 5'-CAG AGG TGC CAC AAA GCT GG-3' (SEQ ID NO: 14); 605: 5'-CCA GCT TTG TGG CAC CTC TG-3' (SEQ ID NO: 15), 606: 5'-CAT CAT GGG GAC CCT CAC GG-3' (SEQ ID NO: 16), 2213: 5'-AGG ATG CAG GCC CTG GTG CT-3' (SEQ ID NO: 17), 2744: 5'CCT CCT CCA CCA GCG CCC CT-3' (SEQ ID NO: 18); 2238: 5'-ATG ATG TCG GAC CCT AAG GCT GTT-3' (SEQ ID NO: 19), 354: 5'-TGG GGA CAG TGA GGA CCG CC-3' (SEQ ID NO: 20). The amplifications, subcloning and sequencing of the PCR products generated with primers 603:604 and 605:606 was performed by Lark Sequencing Technologies Inc. using human genomic DNA as template. The product generated from 603:604 is –2 kb (jt8A) and expands from exon 3 to exon 5. The product generated using 605:606 is ~3.3 kb (jt 9) and expands from exon 5 to exon 6. The primers set 2213–2744 was used to amplify a ~2.5 Kb product (jt15; also referred to as JT115) from the P1 clone p147. This product was then sent to Lark Sequencing Technologies Inc. for subcloning and sequencing. The 2238:354 primers were used to amplify from exon 6 to exon 7 across intron E. This product was not subcloned but was sequenced directly and entirety by us.

DNA sequencing. The P-1 clone (p147), subclones of this clone and PCR products from this clone were sequenced. Most of the sequencing was performed by Lark Sequencing Technologies Inc. using standard sequencing techniques. All important areas (e.g. intron-exon boundaries), and junctions between clones were sequenced in our laboratory. DNA from the PCR products was prepared for sequencing using Wizard™ PCR Preps DNA purification kit purchased from Promega Corp. (Madison, Wis.). The P-1 clone, and plasmid subclones were purified using Qiagen Inc. (Chatsworth, Calif.) Midi plasmid purification kit. The purified PCR products and plasmids were sequenced using the PRISM™ DyeDeoxy Terminator Cycle Sequencing Kit (Applied Biosystems a Division of Perkin-Elmer Corp., Foster City, Calif.), following the manufacturer's protocol. Typically, 0.5 pmoles of template and 3 pmoles of primer were used per sequencing reaction. The sequencing reaction products were purified using Select-D G-50 columns (5 Prime–3 Prime; Boulder, Colo.) and dried. Each sample was then dissolved in 5 µL formamide, 1 µL 50 mM EDTA, heated and located in a Model 370A Automated Fluorescent Sequencer (ABI, Foster City, Calif.). All splice-sites junctions, intron F and junctions across clones were sequenced.

Southern blot. An EcoRI digested genomic (8 µg) blot of DNA from a variety of species was purchased from BIOS Laboratories, New Haven, Conn. The blot was probed with the PEDF cDNA using standard techniques (Sambrook et al., 1989).

5' RACE of PEDF. The 5' RACE was performed as described above by ligating the anchor oligo to human retinal pigment epithelium cDNA previously synthesized on Dynabeads. The 5' end was amplified using the anchor primer (AmpliFinder's kit) and the PEDF-specific primer 2744. The amplification was performed for 30 cycles. One main band was observed at ~230 bp. The PCR products were cloned in pGEM-T (Promega Corp., Madison, Wis.) and sequenced. The longest of these clones was found to extend the 5' end of PEDF by 20 bp.

Isolation of the PEDF gene. The PEDF gene was isolated in a P-1 clone (p147) by Genome Systems (St. Louis, Mo.) using primers 1590 and 1591(1590: 5'-GGA-CGC TGG ATT AGA AGG CAG CAA A-3' (SEQ ID NO: 23); and 1591: 5'-CCA CAC CCA GCC TAG TCC C-3' (SEQ ID NO: 24)). In order to determine if this clone contained the entire PEDF gene, both p147 and human genomic DNA were digested with BamHI, EcoHI, HindIII and PstI then separated by agarose gel electrophoresis in a pulse field apparatus. The agarose gel was blotted and probed with the PEDF cDNA clone (Steele et al. (1993) *Proc. Natl. Acad. Sci. USA* 90:1526–1530). Comparison of the band pattern between the P-1 clone and genomic DNA indicates that the entire PEDF gene is contained in this clone. Furthermore, this result is also indicative that there is only one gene for PEDF.

Sequence of the PEDF gene. A scale map of the gene is shown in FIG. 1. The PEDF gene was sequence in its entirety (SEQ ID NO:43). The clones jt1, jt14, jt6A and related PCR products (jt15, jt8A and jt9)(FIG. 1) were sequenced by Lark Sequencing Technologies Inc. The rest of the gene was sequenced by amplifying different portions of the gene using the p147 clone as template. All exons, intron-exon junctions and the entire intron F were sequenced in both directions in our laboratory as described above from PCR products generated from the P-1 clone, p147. The Not I site downstream from exon 1 was also confirmed by amplifying across it and sequencing the product. The gene expands approximately 16 Kb with 8 exons. All intron-exon junctions obey the AG/GT rule. The intron-exon junctions and flanking sequences are shown in Table I.

jt1: A 7.1 kb cosmid clone isolated from a human genomic cosmid library (Clontech) containing exon 7, exon 8 and the 3' flanking region of the PEDF gene. The 5' end of this clone, an area of approximately 2.1 Kb, is not part of PEDF. This was apparently caused by a rearrengement of the cosmid. This clone was sequenced entirely by Lark Sequencing Technologies Inc.

jt6A: This is a 7.2 kb Not I fragment isolated by Lark Sequencing Technologies Inc. from a λDASHII human genomic library (Statagene). This clone contained >6 Kb of the 5' flanking region, exonl and 424 bp of intron A of the PEDF gene. This clone was sequenced entirely by Lark Sequencing Technologies Inc.

jt8A: This cloned PCR product JT8A generated from genomic DNA using primers 603:604. This clones expands from exon 3 to exon 5 including exon 4 and introns C and D. It was amplified, cloned and sequenced entirely by Lark Sequencing Technologies Inc.

jt9: This cloned PCR product JTBA was generated from genomic DNA using primers 605:606. It contains the entire intron E and portions of exon 5 and exon 6. It was amplified, cloned and sequenced entirely by Lark Sequencing Technologies Inc.

jt15: This clone was obtained from a PCR product amplified using the primer pair 2213:2744 from p147. The clone expands from exon 2 to exon 3 across intron B. The PCR product was submitted to Lark Sequencing Technologies Inc. for subcloning and sequencing.

P1 clone p147: This clone was isolated by Genome Systems Inc. using oligonucleotides 1590:1591. This clone was used to obtain the sequence of intron F (2238:354), and the subclone jt14. It was also used to confirm the intron-exon boundaries initially obtained from the above mentioned clones. All the exons and intron boundaries were amplified (using p147 as template) using intron-specific oligos and the products sequenced. All splice junctions sequences were confirmed as well as the sizes of introns and exons.

jt14: This is a subclone of p147 containing most of intron A, exon 2 and a portion of intron B. This clone was isolated by us and sent to Lark Sequencing Technologies Inc. for sequencing.

Thus from the sequence analysis of all the above mentioned clones and PCR products the structure and size of exons and introns of the human PEDF gene were determined. The 5' splice donor and 3' splice acceptor sites in all junctions conform to the GT/AG consensus.

EXAMPLE 9

Analysis of the PEDF Promoter

In order to obtain some understanding as to the possible transcriptional elements that may be regulating PEDF and guidance for future experiments on PEDF expression, we performed a theoretical analysis of the PEDF 5' flanking region (FIG. 3). The 5' flanking region of the PEDF gene lacks the classical TATAAA signal or TATA-box. However, it contains several impressing features and elements recognized by important transcription factors. There are two Alu repetitive elements from −164 to −591, and from −822 to −1050. Outside the Alu regions, there are two possible sites for the ubiquitous octamer family of transcription factors (Oct) at −29 (ATCCAAAT) and again at −113 (GTG-CAAAT) which deviate by one base from the consensus ATGCAAAT (Parslow et al. (1984) *Proc. Natl. Acad. Sci. U.S.A.* 81:2650–2654; Falkner et al. (1984) *Nature* 310: 71–74; Srurm et al. (1988) *Genes & Devel.* 2:1582–1599, Faisst and Meyer (1992)*Nuc. Acids Res.* 20–3-26). Another element of possible interest is located at −62. This element; GTAAAGTTAAC (SEQ ID NO: 44), which resembles the HNF-1 (hepatocyte nuclear factor) binding consensus GTAATNATTAAC (SEQ ID NO: 45) (Frain, M., et al. (1989) Cell 59.145–147). This is a homedomain-containing transcription factor which transactivates many predominately hepatic genes (Kuo et al. (1990) *Proc. Natl. Acad. Sci. USA* 87.9838–9842) but has been implicated in endodermic differentiation (Baumhueter et al. (1990) *Genes Dev.* 4:371–379). The sequence TCAGGTGATGCACACCTGC (SEQ ID NO: 46) at −202 is very similar to the artificial palindromic sequence (TREp) TCAGGTCATGACCTGA (SEQ ID NO; 47) which is recognized by AP-1 and possibly transactivated by retinoic acid (Umescono et al. (1988) Nature 336:262–265; Linney (1992) *Curr. Topics in Dev. Biol.* 27:309–350). The sequences TGAGTGCA at −22 and TGATGCA at −207 (within the TREp), are similar to the AP-1 consensus sequence TGACTCA (Schule, et al. (1990) *Cell* 61:497–504). The sequence AGGTCATGCACCT (SEQ ID NO: 48) at −204 contained within the TREp is also similar to the developmentally regulated RAR (retinoic acid receptor) motif whose consensus is AGGTCATGACCT (SEQ ID NO: 49) (Faisst and Meyer (1992) *Nuc. Acids. Res.* 20:3–26). The PEA3 element (polyomavirus enhancer activator 3) AGGAAG/A (Martin et al. (1988) *Proc. Natl. Acad. Sci.* USA 85:5839–5843; Faisst and Meyer (1992) *Nuc. Acids Res.* 20:3–26) is present in tandem at −122 and −129, then again at −141 PEA3 is a member of the ETS family of transcription factors (Macleod et al. (1992) TIBS 17:251–256) and its activity seems to be regulated by non-nuclear oncogenes (Wasylyk et al. (1989) EMBO J. 8:3371–3378). One of the most interesting elements is located at −654 with the sequence GTGGTTATG. This element is within the consensus sequence GTGGT/AT/AT/AG (SEQ ID NO: 50) recognized by the C/EBP (CAAT) enhancer binding protein) family of transcription factors (Faisst and Meyer (1992) *Nuc. Acids Res.* 20:3–26) This factor seems to be involved in differentiation that leads to an adult phenotype (Vellanoweth et al. (1994) *Laboratory Investigation* 70:784–799). Three possible CACCC boxes are present one at −845 and two in the reverse orientation at −826 and −905. These are all within the Alu repeat. A possible SpI site (CCCGGC) is present at −153 before the Alu repeat and a consensus SpI site GGCGGG is present −1030 inside the Alu repeat.

EXAMPLE 10

Expression of PEDF mRNA in Cultured Cells Gene Expression Analysis

Multiple human tissue mRNA Northern blots (Clonetech) with 2 ug Poly-(A) RNA per lane were hybridize with a radioactively-labelled 667 bp PCR amplified PEDF product (Tombran-Tink et al., 1994 *Genomics*, 19:266–272). Blots were prehybridized for 15 min at 68° C. in QuickHyb rapid hybridization solution (Stratagene, La Jolla, Calif.) and hybridized for 1 hr at 68° C. in the same solution containing $5 \times 10^6$ cpm DNA/ml. Hybridized blots were washed twice with 100 ml of 2×SSC, 0.1% SDS for 15 min at room temperature and once with 200 ml of 0.1×SSC, 0.1% SDS for 30 min at 68° C. The blots were autoradiographed at −70° C. for 2 hr using Kodax XAR-5 film and DuPont intensifying screens.

Gene Expression:

In order to determine whether expression of the PEDF messenger RNA occurs in human tissues other than in cultured human fetal RPE cells, we analyzed multiple tissue human adult and fetal RNA blots containing equal amounts of poly-(A) RNA for each tissue examined. The results are shown in FIG. 4. The PEDF probe identified a single primer 1.5 kb transcript of varying intensity of hybridization in 14 of the 16 adult tissue analyzed. No signal is detected in either adult kidney or peripheral blood leucocytes. Only a weak signal can be observed in adult brain, pancreas, spleen and thymus. The greatest amount of hybridization for PEDF messenger RNA is seen in human adult liver, skeletal muscle, testis and ovary. Surprisingly, only a very weak signal is observed in total brain RNA. In the fetal tissues examined, a very strong PEDF signal is seen in liver tissue, and interestingly a signal of significant intensity in fetal kidney as compared to no PEDF hybridization in adult kidney samples.

In contrast to the single 1.5 kb transcript observed in the adult tissues, an additional minor transcript of less than 500 bp is labelled variably and with lower intensity in fetal heart, lung and kidney. This may be due to partial degradation of the message or an alternative splicing phenomenon. PEDF is also only expressed in early passaged monkey RPE cells (1st–5th passage) and not in late passaged cells (10th passage). These data demonstrate the relevance of PEDF to senescence.

EXAMPLE 11

Comparative Analysis Of PEDF in a Variety of Phylogenetically Related Species

Evolutionary Conservation Analysis 8 ug of genomic DNA from lymphocytes of a variety of species including a number of mammalian and primate species (BIOS laboratories, New Haven Conn.) was digested with Eco-R1 and separated in 1% agarose gels. The gels were transblotted and membranes containing the digested DNA hybridized using the same procedure and conditions as that for Northern analysis.

Figure 5B:
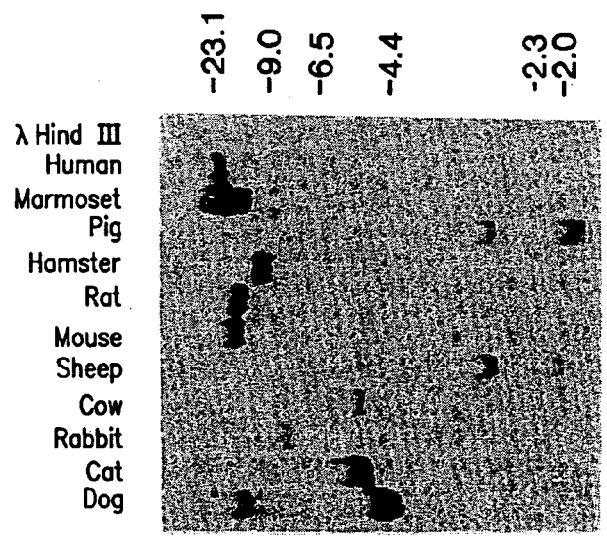
Figure 5A:
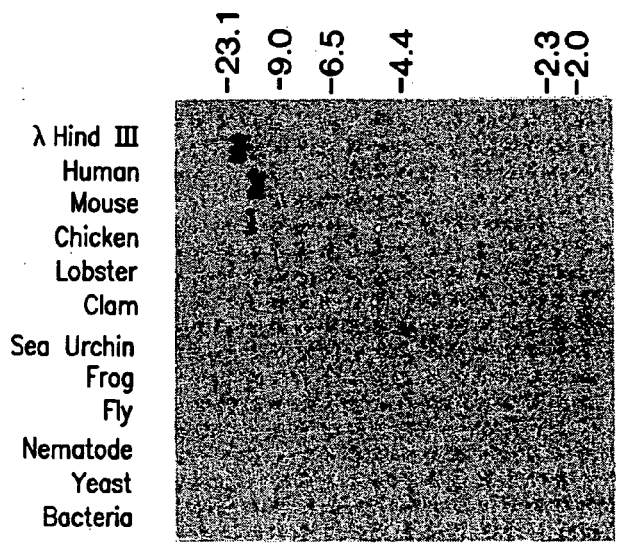

Evolutionary Conservation:

The evolutionary conservation of PEDF among a number of phylogenetically related species was examined. The results are presented in FIG. 5. Using these high stringency hybridization conditions, a large EcoRI restriction fragment of approximately 23 kb is observed in aves, mammals and primates. No hybridization signals were seen in lower species (FIG. 5A) possible due to weak homology of the human PEDF probe used. The EcoRI fragment for both chicken and mouse is somewhat smaller than that for humans. An interesting restriction pattern emerges in several of the mammalian species examined (FIG. 5B). Several smaller restriction fragments ranging in size between 6 kb and 2 kb are seen. The larger fragments range in size between 9 kb and 23 kb and are seen in all primates species examined which has an additional strongly hybridizing polymorphic fragment at approximately 9 kb.

EXAMPLE 12

Neuronotrophic Effects of Pigment Epithelium Derived Factor on Cerebellar Granule Cells in Culture Cell Culture Cerebellar granule cells (CGC) were prepared from 5 or 8-day-old Sprague-Dawley rat pups as described by Novelli et al. (1988, *Brain Res.*, 451:205–212). In brief, tissue free of meninges was minced in a buffer containing 124 mM NaCl, 1 mM $NaH_2PO_4$, 1.2 mM $MgSO_4$, 3 mg/ml bovine serum albumin (BSA), 27 µM phenol red, and 25 mM HEPES (pH 7.4), and centrifuged at 550×g for 3 min. The tissue pellet from 10–20 animals was resuspended and trypsinized (15 min, 37° C.) in 30 ml of the same buffer containing 250 µg/ml trypsin; a further 15 ml of buffer was added containing 26 µg/ml DNase I, 166 ug/ml soybean trypsin inhibitor, and 0.5 mM additional $MgSO_4$ and the tissue was centrifuged again as described above. The pellet was resuspended in 1 ml of buffer supplemented with 80 µg/ml DNase, 0.52 mg/ml of trypsin inhibitor, and 1.6 mM additional $MgSO_4$, and triturated 60 times with a Pasteur pipette. The suspension was diluted with 2 ml of buffer containing 0.1 mM $CaCl_2$ and 1.3 mM additional $MgSO_4$, and undissociated material allowed to settle for 5 min. The supernatant was transferred to another tube, cells were recovered by brief centrifugation and resuspended in serum-containing medium (Eagle's basal medium with 25 mM KCl, 2 mM glutamine, 100 µg/ml gentamycin, and 10 heat inactivated fetal calf serum) or chemically defined medium (DMEM:F 12 (1:1) with 5 µg/ml insulin, 30 nM selenium, 100 µg/ml transferrin, 1000 nM putrescine, 20 nM progesterone, 50 U/ml penicillin, 50 µg/ml streptomycin, and 2 mM glutamine) (Bottenstein, 1985 *Cell Culture in the Neurosciences*, J. E. Bottenstein and G. Sato, eds. New York Plenum Publishing Corp. p. 3–43). Cells were plated in poly-L-lysine-coated 96 well plates (for MTS assay and neurofilament ELISA assay) or 8-well chamber slides (for immunocytochemistry and BrdU labelling) at $2.5 \times 10^5$ cells/$cm^2$ and grown at 37° C. in an atmosphere consisting of 5% $CO_2$ in air. After 1 day in culture, cytosine arabinoside (Ara-C) was added only to cells in serum-supplemented medium (final concentration 50 µM).

MTS Assay

Cerebellar granule cells in 96 well plates were incubated in a $CO_2$ incubator for 4 hours with MTS (3-(4,5-dimethylthiazol-2-yl)-5-(3-carboxymethoxyphenyl)-2-(4-sulfophenyl)-2H-tetrazolium, inner salt) and PMS (phenazine methosulfate) final concentration; 333 µg/ml MTS and 25 µM PMS) (Promega Corp.). In the presence of PMS, MTS is converted to a water-soluble formazan by a dehydrogenase enzyme found in metabolically active cells (Cory et al. (1991) *Cancer Comm*, 3:207–212). The quantity of formazan product was determined by spectrophotometry at 490 nm.

Immunocytochemistry

After 7 days in vitro (DIV), the cells were washed three times in calcium- and magnesium-free phosphate-buffered saline (PBS) and fixed with 2% paraformaldehyde for 10 min, followed by 10 min at −20° C. in 95% ethanol/5% acetic acid. Incubation with primary antibodies against NSE (neuron specific enolase), GABA, calbindin, or glial fibrillary acidic protein (GFAP) was carried out for 60 min at RT. Antibodies were applied at 1:1000–1:5000 in the presence of 2% normal goat serum and 0.2% BSA. The antibodies were visualized using the ABC system (Vector Laboratories) and diaminobenzidine. At least 20 fields were counted from 2–3 wells for each experiment. The average number of cells per field was then calculated to determine the ratio for the number of cells stained by the other antibodies relative to NSE-positive cells in control cultures.

Bromodeoxyridine (BrdU) Labeling

BrdU labeling was performed by the method of Gao et al. (1991 *Neuron*, 6: 705–715) with the following modification. The cells were plated in 8-well chamber slides and rPEDF added immediately. After 24 hours, BrdU (1:100; Amersham cell proliferation kit) was added to the culture medium for 24 hours, after which the cells were fixed in 2% paraformaldehyde (10 min), treated with 95% ethanol/5 acetic acid (10 min), and incubated with an anti-BrdU monoclonal antibody (1:20 for 2 hrs). The cultures were then incubated with a horseradish peroxidase-conjugated goat anti-mouse secondary antibody for 60 min. After diaminobenzidine-peroxidase, the cells were mounted in Gel Mount. The mitotic index was determined by counting the percentage of labeled cells with a microscopy. For each value, a random sample of 3000 cells was counted.

Neurofilament ELISA Assay

The neurofilament ELISA was performed according to the method of Doherty et al. (1984 *J. Neurochem.*, 42:1116–1122) with slight modification. Cultures grown in 96-well microtiter plates were fixed with 4% paraformaldehyde in PBS at 4° C. for 2 hr. The fixed cells were permeabilized by treatment for 15 min with 0.1% Triton X-100 in PBS, followed by incubation for 60 min with PBS containing 10% goat serum to block nonspecific binding. The cultures were then incubated with a monoclonal anti-neurofilament antibody overnight at 4° C. (RMO-42 at 1:100; which stains only neurites in the cultures of cerebellar granule cells). After washing twice with PBS containing 10% goat serum, cells were incubated with secondary antibody (horseradish peroxidase-conjugated goat anti-mouse at 1:1000) for 1 hr. Following sequential washing with PBS and water, the cultures were incubated with 0.2% O-phenylenediamine and 0.02% $H_2O_2$ in 50 mM citrate buffer (pH 5.0) for 30 min. The reaction was stopped by adding an equal volume of 4.5 M $H_2SO_4$. Product formation was quantitated by reading the optical density (O.D.) of an aliquot of the reaction product at 490 nm using a microplate reader.

In order to validate the MTS assay as a measure of live cells, and to determine the range of cell number over which the results would be linear, the experiments shown in FIG. 6 were carried out. In serum-containing medium (SCM) (FIG. 6A), optical density (O.D.) was proportional to cell number plated over a range from $1-9 \times 10^5$ cells/cm$^2$. In contrast, for cells grown in chemically-defined medium (CDM) (FIG. 6B), the linear range covered $1-5 \times 10^5$ cells/cm$^2$. For all subsequent experiments, cells were plated at $2.5 \times 10^5$ cells/cm$^2$, in the middle of the linear range for either type of culture medium.

FIG. 7 shows that PEDF caused a significant increase in cell number by DIV4 with a larger difference at DIV7 and 10. However, the 2–3 fold increases were the result of large decreases in cell numbers in the control cultures. The dose-response curve in chemically-defined medium (FIG. 8), showed that there is a statistically significant effect at 20 ng/ml. Increasing the concentration of PEDF above 50 ng/ml did not produce further increases in CDM.

In order to determine whether the increase in O.D. (MTS assay) in response to PEDF reflected an increase in surviving cells or an increase in proliferation, a BrdU labeling study was performed using cultures from postnatal day 5 (P5) animals (a time when cerebellar granule cells are still dividing in the animal). FIG. 9 shows the effect of PEDF on P5 CGC cultures at DIV1 and 2. Using the MTS assay, PEDF had no effect at DIV1 but caused a small increase in O.D. at DIV2 in either serum-containing medium or chemically defined medium. Therefore, BrdU was added at day 1 and cells were fixed on day 2. The BrdU labeling index was 5% in SCM and 3% in CDM, under control conditions, and PEDF did not increase the BrdU labeling index in either culture medium (FIG. 10). The lack of stimulation of the BrdU labeling index by PEDF implies that enhanced survival rather than increased cell division is responsible for the increased O.D. measured by the MTS assay after exposure to PEDF.

Immunocytochemistry was used to identify the cells present in cultures before and after treatment with PEDF. P8 cultures grown for 7 days with and without PEDF (500 ng/ml) were stained with four different antibodies: a polyclonal rabbit antibody to neuron-specific enolase (NSE), which recognizes all cerebellar neurons (Schmechel et al. (1978) *Science*, 199:313–315); a polyclonal antibody to GABA, which is synthesized in all cerebellar neurons except cerebellar granule cells (Gruol and Crimi (1988) Dev. Brain Res., 41:135–146); an antibody to calbindin, which is a neuron-specific protein and GFAP, an intermediate filament protein present only in astrocytes. The results are summarized in Table 2. PEDF significantly increased the number of NSE-positive cells in both SCM (30% increase) and in CDM (60% increase). There was a small, not statistically significant, increase in the number of GABA-positive neurons and Purkinje cells (calbindin-positive). Thus, PEDF is neurotrophic only for granule neurons. In addition, PEDF significantly decreased the number of GFAP-positive astrocytes present in the cultures (30% decrease in SCM and 40% decrease in CDM). This "gliastatic" property of PEDF is further discussed in Example 14.

TABLE 2

Immunocytochemistry demonstrates that PEDF Increased The Number of NSE-Positive Cells (Neurons) But Decreased GFAP-Positive Cells (Glia)

| Antigen | Treatment | SCM | CDM |
| --- | --- | --- | --- |
| NSE | Control PEDF | 100.0 ± 6.2 | 100.0 ± 4.5 |
|  | PEDF | 127.0 ± 5.9* | 157.2 ± 7.4* |
| GABA | Control | 2.8 ± 0.2 | 1.4 ± 0.2 |
|  | PEDF | 3.2 ± 0.2 | 1.8 ± 0.2 |
| Calbindin | Control | 0.06 ± 0.01 | 0.07 ± 0.02 |
|  | PEDF | 0.07 ± 0.02 | 0.12 ± 0.02 |
| GFAP | Control | 0.86 ± 0.07 | 0.99 ± 0.07 |
|  | PEDF | 0.60 ± 0.03* | 0.60 ± 0.06* |

Postnatal-day 8 cerebellar granule cells were cultured in 8-well chamber slides. PEDF (500 ng/ml) was added at DIV 0, the cells were fixed on DIV 7, and the immunocytochemistry was carried out using antibodies against NSE, GABA, Calbindin and GFAP. At least 20 fields were counted from 2–3 wells for each experiment. Data are expressed as percent of control of NSE-positive cells. Each experiment value represents mean cell number ± SEM.
*$P < 0.005$ compared with each other control by using non-paired test.

In order to investigate the effects of PEDF on neurite outgrowth, a neurofilament ELISA assay was used. Immunocytochemistry had shown that the monoclonal antibody RMO-42, stained only the neurites of cerebellar granule cells in culture, so this antibody was used as a direct measure of neurofilament present only in processes and not the cell body (FIG. 11). PEDF slightly increased neurofilament content, both in SCM and CDM, but the increase was directly proportional to the increase in cell number (FIG. 12).

FIG. 13 summarizes the data from this Example. By 10 days in culture, most untreated CGCs die (control) but 60% or more of the PEDF-treated cells remain viable. PEDF is thus a potent survival factor for brain neurons.

EXAMPLE 13

Neuronotrophic Properties of rPEDF Peptides, BP and BX

Described in the previous sections on the "neuronotrophic" activity of PEDF is the fact that we can produce relatively large amounts of a recombinant PEDF (rPEDF) that exhibits potent neurotrophic activity. Using appropriate recombinant molecular biological technology, we can also produce smaller fragments of the PEDF molecule that can be tested for either neurotrophic or neuronotrophic activity. FIG. 14 shows the effects of two of these truncated forms of PEDF on CGC viability. BX and BP are 24 and 28 kDa fragment from the amino-terminal portion of the PEDF molecule, respectively. Both fragments at 1× or 10× concentrations act as neuron-survival factors, significantly promoting the life of the CGC's. In this experiment, the peptide was given once at the beginning of the experiment and the cell number was determined 7 days later. We conclude that, along with the full PEDF molecule, smaller recombinant peptides near the N-terminal of the molecule are "neuronotrophic".

EXAMPLE 14

Gliastatic Properties of PEDF

Along with neurons in the primary cultures of rat cerebellar granule cells are a small number of different types of glia. Glia are the "support" elements in the CNS for neurons, forming the architectural framework and the metabolic support system on which neurons depend. Glia are also of clinical importance since tumors of the brain are mostly formed by glia and gliosis is a problem in several neurodegenerative diseases. In our system, we first noticed an effect of PEDF on glia when we immunocytochemically stained the cultured mixed population of cells with antibodies specific for neurons and other antibodies specific for different types of glia. For this purpose, we used the standard markers Neuron-Specific Enolase (NSE) and others to demonstrate the presence of neurons, Glial Fibrillary Acidic Protein (GFAP) to demonstrate the presence of astroglia and OX-42 to stain microglia. In this experiment (Table 2), we found the expected increase in NSE staining with PEDF treatment since we then knew that the neurons were living longer but we found an unexpected decrease in GFAP staining. This indicated the possibility of fewer astrocytes in the PEDF-treated cultures.

Because of the distinctive morphology of astroglia and microglia in the culture dishes and their selective staining for GFAP or OX-42, it is possible to individually count their numbers under the microscope under different experimental conditions. This has now been done as outlined in FIGS. 15 and 16. FIG. 15 shows the effects of PEDF on numbers of astroglia in cultures obtained from rat brain at 2 weeks (2w) or 12 weeks (12w) in culture. Times given are 48 hrs, 96 hrs or 7 days after treatment with PEDF. Clearly, under all the conditions tested, PEDF treatment results in a dramatic decrease in the number of astroglia. FIG. 16 shows a parallel analysis of microglia in the same cultures. Administration of PEDF for 48 hrs. or 7 days resulted in fewer numbers of the cells whether they has been cultured for 2 weeks (2 W) or 12 weeks (12 W). Thus, PEDF substantially decreases glial elements over a very long period of time while acting as a survival factor for neurons.

EXAMPLE 15

Characterization of Native Bovine PEDF

Since the specific antibody indicated the presence of PEDF in the adult IPM, we used bovine IPM washes as a source for purification of native PEDF. Although RPE and retinal cells express PEDF mRNA, anti-BH could not detect PEDF bands on Western transfers in these cell extracts, suggesting a rapid PEDF release into the IPM. We now estimate that PEDF is present in bovine IPM at less than 1% of the total soluble protein (i.e. about 2–5 ng/bovine eye). At physiological temperatures, the PEDF protein in the IPM remains stable for extended periods of time and does not form non-reduced complexes resistant to SDS. Thus, its potential usefulness in culture experiments and transplantation in vivo. is greatly enhanced due to its stable nature.

Purification to apparent homogeneity is achieved by a simple two-step procedure (FIG. 17). Components of IPm were fractionated by size-exclusion column chromatography (TSK-3000). The PEDF-immunoreactive fractions were pooled, applied to a cation-exchange column (Mono-S) and immunoreactivity was eluted with a NaCl linear gradient. Purification protocol is detailed in Materials and Methods. Elution profiles of each chromatography are shown in: panel A, TSK-3000 size-exclusion column chromatography, and panel B, mono-S column chromatography. Absorbance at 280 nm is represented by _, and NaCl concentration by - - -, PEDF-immunoreactivity was followed with antiserum Ab-rPEDF. The inserts correspond to Western blot analysis of the indicated fractions. Immunoreaction was performed with a 1:10,000 dilution of Ab-rPEDF and stained with 4-chloro-1-napthtol. Molecular size standards for the TSK-3000 chromatography were: BSA, bovine serum albumin (66,000); and CA, bovine carbonic anhydrase (29,000).

Starting with a wash of soluble IPM components, the first step involves removal of the most abundant protein, IRBP, by size exclusion chromatography. PEDF elutes as a monomeric polypeptide around 50 kDa in size. Since we have determined that PEDF's isoelectric point is 7.2–7.8, we have used S-sepharose column chromatography at pH 6.0 in the second step of our procedure to simultaneously purify and concentrate the protein. Purified protein is recovered at about 2 ug protein per adult bovine eye with a recovery of about 40%. Native PEDF behaves like a monomeric glycoprotein with an apparent molecular weight of 49,500±1,000 on SDS-PAGE.

The purified protein is sensitive to glycosidase F, revealing N-linked oligosaccharides that account for up to 3,000-Mr of the native protein (FIG. 18). To remove asparagine-linked oligosaccharides purified PEDF protein was treated with endoglycosidase H and N-Glycosidase F. Enzymatic reactions were performed as described in Materials and Methods with a total of 200 ng of PEDF protein in the presence or absence of β-mercaptoethanol. Reactions mixtures were applied to SDS-12.5% polyacrylamide gel. Photographs of western transfers of endoglycosidase H (left panel) and N-Glycosidase F (right panel) reactions are shown. Immunoblots were treated with antiserum Ab-rPEDF diluted 1:10,000. Addition in each reaction are indicated at the top. The numbers at the right side of each photograph indicate the migration of biotinylated SDS-PAGE standards: bovine serum albumin (66,200), ovalbumin (45,000) and bovine carbonic anhydrase (31,000). We have shown that purified bovine PEDF promotes neurite outgrowth on Y-79 cells and Weri retinoblastoma cells, and that this activity is blocked by Anti-rPEDF (see below).

The present invention provides the tools for determining the effect of authentic PEDF on the expression of neuronal and glial markers in the CGC cultures and Y-79 tumor cells including NSE, GFAP, neurofilament (NF-200) protein.

EXAMPLE 16

Pigment Epithelium-Derived Factor: Characterization Using a Highly Specific Polyclonal Antibody We have used purified recombinant human PEDF produced in E. coli to develop polyclonal antibodies against PEDF. Anti-rPEDF specifically recognized one polypeptide on Western transfer of IPM wash from adult bovine eyes (FIG. 19). Polyclonal antiserum to human recombinant PEDF specifically recognizes rPEDF. Western transfer and slot blot of human rPEDF were treated with rabbit polyclonal antiserum to rPEDF, Ab-rPEDF. Photographs of immunostaining with 4-chloro-naphthol are shown. Panel A, Western transfers of 0.5 μg of rPEDF were used to assay increasing dilutions of antiserum. rPEDF protein was resolved by SDS-12.5% PAGE before transfer. Dilutions are indicated at the top of each lane. Diluted antiserum was preincubated with rPEDF at 5 μg/ml before using for immunodetection and is indicated as 1:10,000+rPEDF. The numbers to the left indicate the molecular weight of biotinylated SDS-PAGE standards. Panel B increasing amounts of rPEDF in 1% BSA/PBS were applied to a nitrocellulose membrane with a manifold. The membranes were treated with antiserum Anti-rPEDF and rabbit preimmune serum diluted 1:10,000. The numbers to the right indicate the amounts of rPEDF protein blotted on the membrane. The sera used in each paper are indicated at the top of the figure.

Anti-BH specifically recognizes human PEDF on Western transfers at dilutions as low as 1:50,000; importantly, it does not recognize serum $\alpha_1$-antitrypsin. The antibody recognizes one major band on Western transfers of conditioned medium from juvenile monkey RPE cells in culture as well as of IPM from adult bovine eyes. Anti-rPEDF blocked the IPM-promoting neurotrophic activity (FIG. 20). Human retinoblastoma Y-79 cells exponentially growing in serum containing medium were washed twice with PBS, and plated ($2.5\times10^5$) cell per ml) in serum-free MEM supplemented with insulin, transferring and selenium (ITS mix, Collaborative Research Products). Effectors were then added to the cultures. After 7 days at 37° C. in 5% $CO_2$, the cells were attached to poly-D-lysine coated plates with fresh serum-free medium. The differentiation state of the cultures was monitored at different intervals after attachment. Morphology characteristic of 9-day post-attachment cultures is shown. Addition of effectors were as indicated in each panel at the following final concentrations: 125 µg/ml BSA, 1% IPM, and 100 ng/ml purified bovine PEDF. In order to block the neurite outgrowth inducing activity each effector was preincubated with an excess of antiserum Anti-rPEDF (1 µl) in 1% BSA/PBS at 4° C. for at least 6 hours. All photographs are shown at ×50 magnification.

The anti-rPEDF also blocked the neurite-outgrowth activity promoted by the purified PEDF. Our data indicate that PEDF is the only neurotrophic factor in the IPM. These results also suggest that the anti-rPEDF will be useful in probing the PEDF neurotrophic active site as well as the physiological role of PEDF in the IPM and other tissues (e.g. brain) as well. Further, these results indicate that PEDF is a bona fide component of the IPM and is probably the sole neurotrophic component in the extracellular matrix. Moreover, the protein is present in a wide range of tissues and extracellular spaces. The blocking antibody is useful in studies probing the physiological functions of PEDF.

EXAMPLE 17

Pigment Epithelium-Derived Factor:
A Serpin with Neurotrophic Activity

The amino acid sequence derived from a fetal human PEDF cDNA shares identity of its primary structure (~30%) with the serine protease inhibitor (serpin) family, preserving 90% of the residues essential for the structural integrity of serpins. However, recombinant PEDF does not inhibit the serine proteases trypsin, chymotrypsin, elastase or cathepsin G. A natural target for PEDF has not yet been identified. We have analyzed proteins from the interphotoreceptor matrix (IPM), the space between the retinal pigment epithelium and the retina by immunodetection on Western blots with antibodies raised against PEDF and by zymography in gels containing casein as a proteolytic substrate. Our results show that bovine IPM contains a stable, glycosylated PEDF polypeptide (50,000 Mr) at about 2–5 µg per eye. Limited proteolysis of bovine PEDF produced a polypeptide of 46,000 Mr with trypsin, subtilisin, chymotrypsin and elastase, suggesting a globular structure with a hinge region susceptible to proteolytic cleavage. On the other hand, casein SDS-PAGE zymography revealed low protease activity in the IPM which migrated as a double of about 80,000±5,000 Mr. The caseinolytic activities were inhibited 100% with 1 µg/ml aprotinin and 10 mM PMSF added to the gel mixture, but were not affected by E64 or EDTA. Importantly, IPM protein did not react with antibody against plasminogen, a serine protease of about 80,000 Mr. When rPEDF protein was added at 1 µg/ml, the signal for these caseinolytic activities, as well as another serine protease activity of unknown origin, diminished by about 50%. Our results suggest the IPM as a natural extracellular site for a novel serine protease and the serpin PEDF, both present at ≦1% of the total protein.

All of the references cited herein are hereby incorporated in their entireties by reference.

The present invention discloses the general structural features of PEDF and beginnings of understanding of how these relate to function of the protein. PEDF possesses the structural features and general tertiary characteristics previously attributed to serpins but not its anti-protease activity. PEDF is a neurotrophic protein and appears to be the sole component of the IPM that promotes neurite-outgrowth on retinoblastoma cells. However, the reactive center for serine protease inhibition found near the carboxy terminal of classical serpins is not necessary for PEDF's neurotrophic biological activity. Specifically, a polypeptide chain containing a domain from the amino-terminal portion of the molecule (BA) is sufficient for neurotrophic and neuron-survival activity. The present invention further allows for determination of whether the CGC neurons normally die by apoptosis and whether PEDF is an apoptosis inhibitor. In other words, the present invention allows one to determine by what mechanism PEDF "saves" neurons and "inhibits" glia growth or proliferation.

The present invention is useful in determining the specific neurotrophic "active site". Further, the use of rPEDF truncated peptides allows us to define the elements necessary for neuronotrophic and perhaps gliastatic activity of PEDF. The present invention further provides necessary tools to study the interactions of PEDF that trigger the signal for differentiation of retinoblastoma. Recent experiments demonstrate that $^{125}$I-BH binds to retinoblastoma cells in competitive fashion only when added in medium that had been previously "conditioned" by retinoblastoma cells. This suggests that one or more co-factors produced by the cells could be required for binding. The present invention further provides the tools necessary to identify and characterize a putative cell-surface receptor for PEDF or for a PEDF complex from our CGC and retinoblastoma test systems.

Recombinant mutated proteins, proteolytic products and synthetic peptides have become instrumental in domain mapping of functional sites of proteins. Further, the recombinant proteins of the present invention allow the mapping of neurotrophic and neuronotrophic "active sites" on the PEDF molecule and the determination of the cellular transduction mechanism through which this interesting protein exerts its dramatic biological effects.

While this invention has been described with an emphasis upon preferred embodiments, it will be obvious to those of ordinary skill in the art that variations in the preferred nucleic acids coding for, and the amino acid sequences of, PEDF, rPEDF, and equivalent proteins, (BP, BX, BA) the vectors utilizing any such nucleic acids, the recombinant methods of producing such proteins, and the methods of using such proteins, may be realized and that it is intended that the invention may be practiced otherwise than as specifically described herein. Accordingly, this invention includes all modifications encompassed within the spirit and scope of the invention as defined by the following claims.

What is claimed is:

1. An isolated nucleic acid molecule for a human pigment epithelium derived factor (PEDF), wherein said isolated nucleic acid molecule encodes an amino acid sequence comprising SEQ ID NO: 2, or a conservatively modified variant of an amino acid sequence as set forth in SEQ ID NO: 2, wherein said conservatively modified variant induces neurite out growth in Y-79 cells.

2. A vector comprising the nucleic acid molecule of claim 1.

3. An isolated host cell comprising the vector of claim 1.

4. A method for producing a human PEDF protein, the method comprising the steps of:
   a) culturing the host cell of claim 3 sunder conditions suitable for the expression of the polypeptide; and
   b) recovering the polypeptide from the host cell culture.

5. The nucleic acid molecule of claim 1 which encodes SEQ ID NO: 2.

6. A vector comprising the nucleic acid of claim 5.

7. An isolated host cell comprising the vector of claim 6.

8. A method for producing a human PEDF protein, the method comprising the steps of:
   a) culturing the host cell of claim 7 under conditions suitable for the expression of the polypeptide; and
   b) recovering the polypeptide from the host cell culture.

9. The method according to claim 8, wherein the host cell is a eukaryotic cell.

10. The method according to claim 8, wherein the host cell is a prokaryotic cell.

11. An isolated nucleic acid molecule for a human pigment epithelium derived factor (PEDF), wherein said isolated nucleic acid molecule encodes an amino acid sequence consisting of SEQ ID NO: 2; a functional fragment of the amino acid sequence as set forth in SEQ ID NO: 2; or a conservatively modified variant of the amino acid sequence consisting of SEQ ID NO: 2, wherein said functional fragment and conservatively modified variant each induce neurite out growth in Y-79 cells.

12. A vector comprising the nucleic acid molecule of claim 11.

13. An isolated host cell comprising the vector of claim 12.

14. A method for producing a human PEDF protein, the method comprising the steps of:
   a) culturing the host cell of claim 13 under conditions suitable for the expression of the polypeptide; and
   b) recovering the polypeptide from the host cell culture.

15. The method according to claim 14, wherein the host cell is a eukaryotic cell.

16. The method according to claim 14, wherein the host cell is a prokaryotic cell.

17. An isolated nucleic acid molecule for a human pigment epithelium derived factor (PEDF) consisting of a nucleic acid sequence that encodes amino acid residues 44–121 of SEQ ID NO: 2, wherein the encoded amino acid residues 44–121 induce neurite out growth in Y-79 cells.

18. A vector comprising the nucleic acid molecule of claim 17.

19. An isolated host cell comprising the vector of claim 18.

20. A method for producing a human PEDF protein, the method comprising the steps of:
   a) culturing the host cell of claim 19 under conditions suitable for the expression of the polypeptide; and
   b) recovering the polypeptide from the host cell culture.

21. The method according to claim 20, wherein the host cell is a eukaryotic cell.

22. The method according to claim 20, wherein the host cell is a prokaryotic cell.

23. An isolated nucleic acid molecule for a human pigment epithelium derived factor (PEDF), wherein said isolated nucleic acid molecule encodes an amino acid sequence comprising SEQ ID NO: 3, or a conservatively modified variant of an amino acid sequence as set forth in SEQ ID NO: 3, wherein said conservatively modified variant induces neurite out growth in Y-79 cells.

24. A vector comprising the nucleic acid molecule of claim 23.

25. An isolated host cell comprising the vector of claim 24.

26. A method for producing a human PEDF protein, the method comprising the steps of:
   a) culturing the host cell of claim 25 under conditions suitable for the expression of the polypeptide; and
   b) recovering the polypeptide from the host cell culture.

27. The method according to claim 26, wherein the host cell is a eukaryotic cell.

28. The method according to claim 26, wherein the host cell is a prokaryotic cell.

29. The nucleic acid molecule of claim 23 which encodes SEQ ID NO: 3.

30. A vector comprising the nucleic acid of claim 29.

31. An isolated host cell comprising the vector of claim 30.

32. A method for producing a human PEDF protein, the method comprising the steps of:
   a) culturing the host cell of claim 31 under conditions suitable for the expression of the polypeptide; and
   b) recovering the polypeptide from the host cell culture.

33. The method according to claim 32, wherein the host cell is a eukaryotic cell.

34. The method according to claim 32, wherein the host cell is a prokaryotic cell.

35. An isolated nucleic acid molecule for a human pigment epithelium derived factor (PEDF), wherein said isolated nucleic acid molecule encodes an amino acid sequence consisting of SEQ ID NO: 3; a functional fragment of the amino acid sequence as set forth in SEQ ID NO: 3; or a conservatively modified variant of the amino acid sequence consisting of SEQ ID NO: 3, wherein said functional fragment and conservatively modified variant each induce neurite out growth in Y-79 cells.

36. A vector comprising the nucleic acid molecule of claim 35.

37. An isolated host cell comprising the vector of claim 36.

38. A method for producing a human PEDF protein, the method comprising the steps of:
   a) culturing the host cell of claim 37 under conditions suitable for the expression of the polypeptide; and
   b) recovering the polypeptide from the host cell culture.

39. The method according to claim 38, wherein the host cell is a eukaryotic cell.

40. The method according to claim 38, wherein the host cell is a prokaryotic cell.

41. An isolated nucleic acid molecule for a pigment epithelium derived factor (PEDF) comprising residues 137 to 1393 of SEQ ID NO: 1.

42. A vector comprising the nucleic acid molecule of claim 41.

43. An isolated host cell comprising the vector of claim 42.

44. A method for producing a human PEDF protein, the method comprising the steps of:
  a) culturing the host cell of claim 43 under conditions suitable for the expression of the polypeptide; and
  b) recovering the polypeptide from the host cell culture.

45. The method according to claim 44, wherein the host cell is a eukaryotic cell.

46. The method according to claim 44, wherein the host cell is a prokaryotic cell.

47. The isolated nucleic acid molecule of claim 41 comprising SEQ ID NO: 1.

48. A vector comprising the nucleic acid molecule of claim 47.

49. An isolated host cell comprising the vector of claim 48.

50. A method for producing a human PEDF protein, the method comprising the steps of:
  a) culturing the host cell of claim 49 under conditions suitable for the expression of the polypeptide; and
  b) recovering the polypeptide from the host cell culture.

51. The method according to claim 50 wherein the host cell is a eukaryotic cell.

52. The method according to claim 50 wherein the host cell is a prokaryotic cell.

* * * * *

UNITED STATES PATENT AND TRADEMARK OFFICE
CERTIFICATE OF CORRECTION

| | |
|---|---|
| PATENT NO. | : 7,179,621 B1 |
| APPLICATION NO. | : 09/630629 |
| DATED | : February 20, 2007 |
| INVENTOR(S) | : Gerald J. Chader et al. |

It is certified that error appears in the above-identified patent and that said Letters Patent is hereby corrected as shown below:

<u>Title Page</u>,
Item (75), Inventor:
Delete second inventor "Ignacio R. Rodriguez, Rockville, MD (US);".

<u>Title Page</u>,
Item (60), Related U.S. Application Data:
Lines 7-8, delete "Jul. 4, 1992," and insert -- Jun. 4, 1992, --.

<u>Title Page</u>,
Item (57), ABSTRACT,
Line 2, delete "epithelium derived" and insert -- epithelium-derived --.

<u>Column 3</u>,
Line 51, delete "line" and insert -- lines --.

<u>Column 4</u>,
Line 17, after "levels" insert -- was --.
Line 50, delete "vesus" and insert -- versus --.
Line 59, delete "Pc0.0005 vesus" and insert -- P<0.0005 --.
Line 59, delete "vesus" and insert -- versus --.

<u>Column 5</u>,
Line 17, delete "vesus" and insert -- versus --.
Line 38, delete "$\leqq 1$" and insert -- $\leq 1$ --.)
Line 51, delete "rPEDF:" and insert -- rPEDF. --.

<u>Column 10</u>,
Line 55, after "eukaryotic" insert -- or --.

<u>Column 13</u>,
Line 43, delete "$\lambda$FS17" and insert -- $\pi$FS17 --.

<u>Column 14</u>,
Line 56, delete "PEF" and insert -- PEDF --.

<u>Column 15</u>,
Line 36, after "46,000" insert -- $M_T$ --.
Line 39, delete "M" and insert -- $M_T$ --.

UNITED STATES PATENT AND TRADEMARK OFFICE
CERTIFICATE OF CORRECTION

PATENT NO. : 7,179,621 B1
APPLICATION NO. : 09/630629
DATED : February 20, 2007
INVENTOR(S) : Gerald J. Chader et al.

It is certified that error appears in the above-identified patent and that said Letters Patent is hereby corrected as shown below:

Column 19,
Line 37, delete "(NDR1," and insert -- (NDRI, --.
Line 38, delete "DATP" and insert -- dATP --.
Line 56, delete "2× GeneAmp®" and insert -- 2×GeneAmp® --.
Line 60, delte "2× mix" and insert -- 2×mix --.

Column 20,
Line 20, delete "10× SSPE," and insert -- 10×SSPE, --.

Column 21,
Line 12, delete "–2 kb" and insert -- ~2 kb --.
Line 16, delete "~2.5 Kb" and insert -- ~2.5 kb --.
Line 21, delete "entirety" and insert -- entirely --.
Line 62, delete "5'-GGA-CGC" and insert -- 5'-GGA CGC --.

Column 22,
Line 28, delete "rearrengement" and insert -- rearrangement --.
Line 44, delete "JTBA" and insert -- JT8A --.

Column 23,
Line 17, delete "impressing" and insert -- interesting --.
Line 26, delete "Srurm" and insert -- Sturm --.
Line 27, delete "20–3-26)." and insert -- 20:3-26). --.
Line 28, delete "element;" and insert -- element, --.
Line 32, delete "Cell 59.145–147)," and insert -- Cell 59:145–147). --.
Line 35, delete "87.9838-9842)" and insert -- 87:9838-9842) --.
Line 37, delete "TCAGGTGATGCACACCTGC" and insert
-- TCAGGTGATGCACCTGC --.
Line 40, delete "(SEQ ID NO; 47)" and insert -- (SEQ ID NO: 47) --.
Line 46, delete "AGGTCATGCACCT" and insert -- AGGTGATGCACCT --.
Line 55, delete "–141 PEA3" and insert -- –141. PEA3 --.
Line 62, delete "(CAAT)" and insert -- (CAAT --.
Line 64, delete "20:3–26) This" and insert -- 20:3–26). This --.
Line 65, after "involved in" insert -- terminal --.

Column 24,
Line 3, delete "SpI" and insert -- Sp1 --.
Line 4, delete "SpI" and insert -- Sp1 --.

UNITED STATES PATENT AND TRADEMARK OFFICE
CERTIFICATE OF CORRECTION

PATENT NO. : 7,179,621 B1
APPLICATION NO. : 09/630629
DATED : February 20, 2007
INVENTOR(S) : Gerald J. Chader et al.

It is certified that error appears in the above-identified patent and that said Letters Patent is hereby corrected as shown below:

<u>Column 25,</u>
Line 35, delete "550×g" and insert -- 550 xg --.
Line 52, delete "10 heat" and insert -- 10% heat --.

<u>Column 29,</u>
Line 37, delete "has" and insert -- have --.
Line 57, delete "vivo." and insert -- vivo, --.

<u>Column 32,</u>
Line 8, delete "$\leqq 1\%$" and insert -- $\leq 1\%$ --.

<u>Column 93,</u>
Line 11, delete "claim 1." and insert -- claim 2. --.
Line 14, delete "sunder" and insert -- under --.

Signed and Sealed this

Twenty-ninth Day of April, 2008

JON W. DUDAS
*Director of the United States Patent and Trademark Office*

SEQUENCE LISTING

<160> NUMBER OF SEQ ID NOS: 50

<210> SEQ ID NO 1
<211> LENGTH: 1512
<212> TYPE: DNA
<213> ORGANISM: Artificial Sequence
<220> FEATURE:
<223> OTHER INFORMATION: Synthetic construct

<400> SEQUENCE: 1

```
gctgtaatct gaagcctgct ggacgctgga ttagaaggca gcaaaaaaag ctctgtgctg      60
gctggagccc cctcagtgtg caggcttaga gggactaggc tgggtgtgga gctgcagcgt     120
atccacaggc cccaggatgc aggccctggt gctactcctc tgcattggag ccctcctcgg     180
gcacagcagc tgccagaacc ctgccagccc cccggaggag ggctcccag accccgacag      240 cacaggggcg ctggtggagg aggaggatcc tttcttcaaa gtccccgtga acaagctggc     300
agcggctgtc tccaacttcg gctatgacct gtaccgggtg cgatccagca tgagccccac     360
gaccaacgtg ctcctgtctc ctctcagtgt ggccacggcc ctctcggccc tctcgctggg     420
agcggagcag cgaacagaat ccatcattca ccgggctctc tactatgact tgatcagcag     480
cccagacatc catggtacct ataaggagct ccttgacacg tcactgccc ccagaagaa      540 cctcaagagt gcctcccgga tcgtctttga aagaagcta cgcataaaat ccagctttgt     600
ggcacctctg gaaaagtcat atgggaccag gcccagagtc ctgacgggca accctcgctt     660
ggacctgcaa gagatcaaca actgggtgca ggcgcagatg aaagggaagc tcgccaggtc     720
cacaaaggaa attcccgatg agatcagcat tctccttctc ggtgtggcgc acttcaaggg     780
gcagtgggta acaaagtttg actccagaaa gacttccctc gaggatttct acttggatga     840
agagaggacc gtgagggtcc ccatgatgtc ggaccctaag ctgtttac gctatggctt      900 ggattcagat ctcagctgca agattgccca gctgcccttg accggaagca tgagtatcat     960
cttcttcctg cccctgaaag tgacccagaa tttgaccttg atagaggaga gcctcacctc    1020
cgagttcatt catgacatag accgagaact gaagaccgtg caggcggtcc tcactgtccc    1080
caagctgaag ctgagttacg aaggcgaagt caccaagtcc ctgcaggaga tgaagctgca    1140
atccttgttt gattcaccag actttagcaa gatcacaggc aaacccatca agctgactca    1200
ggtggaacac cgggctggct ttgagtggaa cgaggatggg gcgggaacca ccccagccc    1260 agggctgcag cctgcccacc tcaccttccc gctggactat caccttaacc agcctttcat    1320
cttcgtactg agggacacag acacaggggc ccttctcttc attggcaaga ttctggaccc    1380
caggggcccc taatatccca gtttaatatt ccaatacct agaagaaaac ccgagggaca    1440
gcagattcca caggacacga aggctgcccc tgtaaggttt caatgcatac aataaaagag    1500
ctttatccct gc                                                        1512
```

<210> SEQ ID NO 2
<211> LENGTH: 418
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (117)..(1373)
<223> OTHER INFORMATION: /note= "product= "pigment epithelial-derived
    factor" gene- "PEDF" condon_start= 1"
<220> FEATURE:

-continued

```
<221> NAME/KEY: misc_feature
<222> LOCATION: (117)..(1373)
<223> OTHER INFORMATION: /note= "product= "pigment epithelial-derived
      factor" gene- "PEDF" condon_start= 1"

<400> SEQUENCE: 2
```

| Met | Gln | Ala | Leu | Val | Leu | Leu | Leu | Cys | Ile | Gly | Ala | Leu | Leu | Gly | His |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Ser | Cys | Gln | Asn | Pro | Ala | Ser | Pro | Pro | Glu | Glu | Gly | Ser | Pro | Asp |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Pro | Asp | Ser | Thr | Gly | Ala | Leu | Val | Glu | Glu | Asp | Pro | Phe | Phe | Lys |
|-----|-----|-----|-----|-----|-----|-----|-----|-----|-----|-----|-----|-----|-----|-----|
|     |     | 35  |     |     |     |     | 40  |     |     |     |     | 45  |     |     |

| Val | Pro | Val | Asn | Lys | Leu | Ala | Ala | Val | Ser | Asn | Phe | Gly | Tyr | Asp |
|-----|-----|-----|-----|-----|-----|-----|-----|-----|-----|-----|-----|-----|-----|-----|
|     | 50  |     |     |     |     | 55  |     |     |     |     | 60  |     |     |     |

| Leu | Tyr | Arg | Val | Arg | Ser | Met | Ser | Pro | Thr | Thr | Asn | Val | Leu | Leu |
|-----|-----|-----|-----|-----|-----|-----|-----|-----|-----|-----|-----|-----|-----|-----|
| 65  |     |     |     | 70  |     |     |     |     | 75  |     |     |     |     | 80  |

| Ser | Pro | Leu | Ser | Val | Ala | Thr | Ala | Leu | Ser | Ala | Leu | Ser | Leu | Gly | Ala |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Glu | Gln | Arg | Thr | Glu | Ser | Ile | Ile | His | Arg | Ala | Leu | Tyr | Tyr | Asp | Leu |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ile | Ser | Ser | Pro | Asp | Ile | His | Gly | Thr | Tyr | Lys | Glu | Leu | Leu | Asp | Thr |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Val | Thr | Ala | Pro | Gln | Lys | Asn | Leu | Lys | Ser | Ala | Ser | Arg | Ile | Val | Phe |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Glu | Lys | Lys | Leu | Arg | Ile | Lys | Ser | Ser | Phe | Val | Ala | Pro | Leu | Glu | Lys |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Ser | Tyr | Gly | Thr | Arg | Pro | Arg | Val | Leu | Thr | Gly | Asn | Pro | Arg | Leu | Asp |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Leu | Gln | Glu | Ile | Asn | Asn | Trp | Val | Gln | Ala | Gln | Met | Lys | Gly | Lys | Leu |
|-----|-----|-----|-----|-----|-----|-----|-----|-----|-----|-----|-----|-----|-----|-----|-----|
|     |     |     |     | 180 |     |     |     |     | 185 |     |     |     |     | 190 |     |

| Ala | Arg | Ser | Thr | Lys | Glu | Ile | Pro | Asp | Glu | Ile | Ser | Ile | Leu | Leu | Leu |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Gly | Val | Ala | His | Phe | Lys | Gly | Gln | Trp | Val | Thr | Lys | Phe | Asp | Ser | Arg |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Lys | Thr | Ser | Leu | Glu | Asp | Phe | Tyr | Leu | Asp | Glu | Glu | Arg | Thr | Val | Arg |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Val | Pro | Met | Met | Ser | Asp | Pro | Lys | Ala | Val | Leu | Arg | Tyr | Gly | Leu | Asp |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Ser | Asp | Leu | Ser | Cys | Lys | Ile | Ala | Gln | Leu | Pro | Leu | Thr | Gly | Ser | Met |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Ser | Ile | Ile | Phe | Phe | Leu | Pro | Leu | Lys | Val | Thr | Gln | Asn | Leu | Thr | Leu |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Ile | Glu | Glu | Ser | Leu | Thr | Ser | Glu | Phe | Ile | His | Asp | Ile | Asp | Arg | Glu |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Leu | Lys | Thr | Val | Gln | Ala | Val | Leu | Thr | Val | Pro | Lys | Leu | Lys | Leu | Ser |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Tyr | Glu | Gly | Glu | Val | Thr | Lys | Ser | Leu | Gln | Glu | Met | Lys | Leu | Gln | Ser |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Leu | Phe | Asp | Ser | Pro | Asp | Phe | Ser | Lys | Ile | Thr | Gly | Lys | Pro | Ile | Lys |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Leu | Thr | Gln | Val | Glu | His | Arg | Ala | Gly | Phe | Glu | Trp | Asn | Glu | Asp | Gly |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

| Ala | Gly | Thr | Thr | Pro | Ser | Pro | Gly | Leu | Gln | Pro | Ala | His | Leu | Thr | Phe |
|-----|-----|-----|-----|-----|-----|-----|-----|-----|-----|-----|-----|-----|-----|-----|-----|
|     | 370 |     |     |     |     | 375 |     |     |     |     | 380 |     |     |     |     |

```
Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro
```

<210> SEQ ID NO 3
<211> LENGTH: 379
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: /note= "Met1....Ile 4 is an N-terminal fusion
      to Asp 26...Pro 400 of SEQ ID NO:2; Met-18....Glu 25 of SEQ ID NO:
      2 is deleted"

<400> SEQUENCE: 3

```
Met Asn Arg Ile Asp Pro Phe Phe Lys Val Pro Val Asn Lys Leu Ala
1               5                   10                  15

Ala Ala Val Ser Asn Phe Gly Tyr Asp Leu Tyr Arg Val Arg Ser Ser
            20                  25                  30

Met Ser Pro Thr Thr Asn Val Leu Leu Ser Pro Leu Ser Val Ala Thr
        35                  40                  45

Ala Leu Ser Ala Leu Ser Leu Gly Ala Glu Gln Arg Thr Glu Ser Ile
    50                  55                  60

Ile His Arg Ala Leu Tyr Tyr Asp Leu Ile Ser Ser Pro Asp Ile His
65                  70                  75                  80

Gly Thr Tyr Lys Glu Leu Leu Asp Thr Val Thr Ala Pro Gln Lys Asn
                85                  90                  95

Leu Lys Ser Ala Ser Arg Ile Val Phe Glu Lys Lys Leu Arg Ile Lys
            100                 105                 110

Ser Ser Phe Val Ala Pro Leu Glu Lys Ser Tyr Gly Thr Arg Pro Arg
        115                 120                 125

Val Leu Thr Gly Asn Pro Arg Leu Asp Leu Gln Glu Ile Asn Asn Trp
130                 135                 140

Val Gln Ala Gln Met Lys Gly Lys Leu Ala Arg Ser Thr Lys Gln Ile
145                 150                 155                 160

Pro Asp Glu Ile Ser Ile Leu Leu Leu Gly Val Ala His Phe Lys Gly
                165                 170                 175

Gln Trp Val Thr Lys Phe Asp Ser Arg Lys Thr Ser Leu Glu Asp Phe
            180                 185                 190

Tyr Leu Asp Glu Glu Arg Thr Val Arg Val Pro Met Met Ser Asp Pro
        195                 200                 205

Lys Ala Val Leu Arg Tyr Gly Leu Asp Ser Asp Leu Ser Cys Lys Ile
    210                 215                 220

Ala Gln Leu Pro Leu Thr Gly Ser Met Ser Ile Ile Phe Phe Leu Pro
225                 230                 235                 240

Leu Lys Val Thr Gln Asn Leu Thr Leu Ile Glu Glu Ser Leu Thr Ser
                245                 250                 255

Glu Phe Ile His Asp Ile Asp Arg Glu Leu Lys Thr Val Gln Ala Val
            260                 265                 270

Leu Thr Val Pro Lys Leu Lys Leu Ser Tyr Glu Gly Glu Val Thr Lys
        275                 280                 285

Ser Leu Gln Glu Met Lys Leu Gln Ser Leu Phe Asp Ser Pro Asp Phe
```

```
                290             295             300
Ser Lys Ile Thr Gly Lys Pro Ile Lys Leu Thr Gln Val Glu His Arg
305                 310                 315                 320

Ala Gly Phe Glu Trp Asn Glu Asp Gly Ala Gly Thr Thr Pro Ser Pro
                325                 330                 335

Gly Leu Gln Pro Ala His Leu Thr Phe Pro Leu Asp Tyr His Leu Asn
            340                 345                 350

Gln Pro Phe Ile Phe Val Leu Arg Asp Thr Asp Gly Ala Leu Leu
        355                 360                 365

Phe Ile Gly Lys Ile Leu Asp Pro Arg Gly Pro
    370                 375

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
agyaayttyt aygayctsta                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
ctytcytcrt csagrtaraa                                              20

<210> SEQ ID NO 6
<211> LENGTH: 19
<212> TYPE: PRT
<213> ORGANISM: Artificial Sequence
<220> FEATURE:
<223> OTHER INFORMATION: Synthetic construct

<400> SEQUENCE: 6

Thr Ser Leu Glu Asp Phe Tyr Leu Asp Glu Glu Arg Thr Val Arg Val
1               5                   10                  15

Pro Met Met

<210> SEQ ID NO 7
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (28)..(28)
<223> OTHER INFORMATION: Xaa can be any naturally occurring amino acid

<400> SEQUENCE: 7

Ala Leu Tyr Tyr Asp Leu Ile Ser Ser Pro Asp Ile His Gly Thr Tyr
1               5                   10                  15

Lys Glu Leu Leu Asp Thr Val Thr Ala Pro Gln Xaa Asn
            20                  25

<210> SEQ ID NO 8
<211> LENGTH: 7
```

-continued

```
<212> TYPE: PRT
<213> ORGANISM: Artificial Sequence
<220> FEATURE:
<223> OTHER INFORMATION: Synthetic construct

<400> SEQUENCE: 8

Met Asn Glu Leu Gly Pro Arg
1               5

<210> SEQ ID NO 9
<211> LENGTH: 4421
<212> TYPE: DNA
<213> ORGANISM: Homo sapiens
<220> FEATURE:
<221> NAME/KEY: misc_feature
<223> OTHER INFORMATION: JT 1 - 7.1 kb Bam HI fragment derived from
      human placental genomic DNA; a; so referred to as JT101

<400> SEQUENCE: 9 ggatccttg gttgggtgt tggggaaggc agggtttaa cggaaatctc tctccatctc      60
tacagagctg caatccttgt ttgattcacc agactttagc aagatcacag gcaaacccat   120
caagctgact caggtggaac accgggctgg ctttgagtgg aacgaggatg gggcgggaac   180
cacccccagc ccagggctgc agcctgccca cctcaccttc ccgctggact atcaccttaa   240
ccagcctttc atcttcgtac tgagggcaca agacacaggg gcccttctct tcattggcaa   300
gattctggac cccaggggcc cctaatatcc cagtttaata ttccaatacc ctagaagaaa   360
acccgaggga cagcagattc cacaggacac gaaggctgcc cctgtaaggt ttcaatgcat   420
acaataaaag agctttatcc ctaacttctg ttacttcgtt cctcctccta ttttgagcta   480
tgcgaaatat catatgaaga gaaacagctc ttgaggaatt tggtggtcct ctacttctag   540
cctggtttta tctaaacact gcaggaagtc accgttcata agaactctta gttacctgtg   600
ttggataagg cacggacagc ttctctgctc tgggggtatt tctgtactag gatcagtgat   660
cctcccggga ggccatttcc tgcccccata atcagggaag cctgctcgta acaacacat    720 ggacagatag gagaggccat tgtaactta aggaaacgga cccgatacgt aaagattctg    780
aacatattct ttgtaaggag gtatgcctat tttacaaagt acagccgggt gtggtggctc   840
atggctataa tcccagcact tgggaggcc gaggcgggcg gatcacctga gatcaggagt    900
ttgagaccag cctgaccaac acggagaaac cccgtctgta ctaaaaatac aaaattagca   960
gggtgtggtg gtacatgcct gtaatcccag ctactgggga ggctgaggca ggagaatcac  1020
ttgaacccgg gaggcggagg ttgcagtgag ccgagatcac gccattgcac tccaatctag  1080
gcaataagag caaaactccg tctcaaacaa caaaaaacca agtataact gggcttttg    1140 aagaacatga acatgccca gtgtctgaag tagaataact accgaactgt ccgtaggact   1200 aaacttttc ttgaaaaagc tctaccaaaa aaagtcaccg gccactccct tgtcacagtt   1260
attagacagg aggagaaatg ataattctac tgcccttcat tctacaaatg tttgagtgct   1320
aactgtattc cagattctca aaaagctatt gccaggtatc tctggggcta ctgatttcct   1380
gatcataatg caatgcaac caacaggcac ttgggcatgg tgagggtggg caagctttca   1440
aaagcagcgt ggatctggca ttctttttcca cgaatgcacc tcaactactt ggcaccagtg   1500
gtaacacagc aaccagggtt ccgacctaga gaatcccgta accttctgac tggaacgggg  1560
tctgggctgt cgctacacat cctggtggaa ggcagctatc atccctacct tctgccttct   1620
gtctcttaaa tctgaaccac aaacagcaac gtccataccc tcagcattgt tagaatcccc  1680
tgcagcctcc agttctcata ctgtctgtat tctactcgcc agtttggaga ggtctggtgg   1740
```

-continued

```
agaaaaggag tctcttttca ggcttgacaa caaatagaac tcagggccgg gcgcggtggc   1800
tcacgcctgt catcccagca ctgtgggagg ccgaagcggg cggatcacct gaggtcggga   1860
gctcaagacc agcctggcca acatggagaa atcccatctt tactaaaaat acaaaattag   1920
ccgggcgtac tggcgaatgc ctgtaatgcc agcttctcgg gaggctgagg caggagaatc   1980
gcttgaacct gggaggcaga ggttgcggtg agccaagact gtgccactgt actccagcct   2040
tggtgacaga gggagactct gtcttaagaa aaaagaaaa aaaaaaaaa agggccgggc     2100
tcacgcctgt aatcccagca ctttgggagg ccaaatcacc tgaggccggg agtttgatac   2160
caacctgacc aacatagtga atcccgtct ctactaaaaa tacaaaatta gccaggcgtg    2220
gtggcgggcg cctgtaatcc cagctactcg ggaggctgaa gcaggagaat cacttgaacc   2280
cggaaggcgg aggttgccgt aagccaagat cgcgccattg cgctccagcc tgggcaacaa   2340
gagtgaaact ccatctcaaa aacaaaacaa aacaaaacaa aaccaacaac tcagaaggag   2400
gcatatgtgt tataaagtct ttactacaac tttgatttta ttagtggttg gttactgact   2460
ctgccaagag tacagaatga agggcagaga gtaaggactg gaaaactggc aggaaacaca   2520
ctgacagccg tcatccctgg aggaaactgc tcaataaaac ggctccatat ttacttctct   2580
ggtcacagtt catactccac gattttaaca aaggagtcga ggaagctaga tactgtaagt   2640
ggaacggtgt gtctctggag gtaagcaggc ttgctgattt cttgttttat aattcttttt   2700
taattacaat gtaactacta agagcttcag ttcccactgg agtggtgcac acatctcatt   2760
actactaaaa ccacaggaat gttccaggga aacagactat catcactgag cgaggtggaa   2820
tccagccaaa accccaggct aacatccaga tgcctgcata tcagctaaaa tccttttaaa   2880
ggacttggaa tctccagata ctagttttaa gtcttttctg ggaactggga gtttgtactg   2940
gaggccactt aactatttca aaaaatattc accaaaatag gtgtctctct gactgcaacg   3000
gtttgagtcc tcctcagccc tcatatccta ggcttcggac tgttgggaaa gtcttatctt   3060
cctgacgaaa gctcagcagc aacagaacct gttatttttt tgttgagaca gggtcttact   3120
ctgtcaccca ggctggagtg cagtagtgcg atcttggctc actgcagcct cagcctacca   3180
ggctcaggtg accctatctc agcttctcga gtaggtggga ctacaggcat gtgccaccat   3240
gctcggtgaa ctaaacaaac ttttttgtag tgatacggtc tcactatatt gcccaggctg   3300
gttttgaact cctgggctca agtgatcctc ccacctcagc gtctcaaagt actgggatta   3360
caggtgtgag cctctacact gggcctgcag aacctacaca gaatccgcac ctggtctgca   3420
gaacccacac ccgacccaca gaacccacac ccgacccaca gaacccacat ctggcagcag   3480
aacctcttag tatttttttt ttttctttga gatggagtct ggctctgtca cccaggctgg   3540
agtgcagtgg cgcgatctcg gctcactgca agctcttcct cccgggttca ccccattctc   3600
ctgcctcaac ctcccgagta gctgtgaata caggcgtccg ccaccacgcc cgactaattt   3660
ttttgtattt ttagtagaga cggggtttca ccgtgttagc caggatggtc tggatctcct   3720
gacctcgtga tctgcctgcc tcggcctccc aaagtgctgg gattacaggc ttgagccacc   3780
gcacccggcc tcttattttt tttttgaga tggagtctca cactgtcacc tgggctggag   3840
tgcagtggag cgatctcggc tcactgcaac ctccgcctcc tgggttcaag agattctcct   3900
gcctcagcct cccaagtagc tgggattaca ggtgcccacc accacgcctg gctagttttt   3960
tgtattttta gtaaagatgg ggtttcacca tgttggccag gctggtcttg aactcctgac   4020
atcaggtgat ccgcccacct tagcctccca aagtgctggg attacaggcg tgagccacca   4080
```

-continued

```
tacctggcca gcaaaacctc tttaacttgt gttccatggg ctcctttcct gtgggtcaaa    4140
atcctcctgg aaccctacaa tgcaggccct acagggtgg gtggtaagtc caacaaacag    4200
gatttcatct tctggagctc ctggatttca tcgtcccatg gccacagtg cagcgacaga    4260 acctcctcag ctttctgtat tgtgctcagg gcttcgggta ctgcaaacct gagccaaggg    4320
aggtaagagg agttagttca ctgattcgtg aggcaaatgt taattgaggg cctactcaca    4380
caccgtgaag aatgtaagat catttctgtc atcaaggatc c                       4421
```

<210> SEQ ID NO 10
<211> LENGTH: 7210
<212> TYPE: DNA
<213> ORGANISM: Homo sapiens
<220> FEATURE:
<221> NAME/KEY: misc_feature
<223> OTHER INFORMATION: JT6A - 7.0 kb Not 1-Not fragment; derived from
      human placental genomic DNA; also referred to as JT106

<400> SEQUENCE: 10

```
gatctagagc ggccgcaggg tggactgtgc tgaggaaccc tgggcccagc aggggtggca      60
gcccgcgcag tgccacgttt ggcctctggc cgctcgccag gcatcctcca ccccgtggtc     120
ccctctgacc tcgccagccc tccccgggga cacctccacg ccagcctggc tctgctcctg     180
gcttcttctt ctctctatgc ctcaggcagc cggcaacagg gcggctcaga acagcgccag     240
cctcctggtt tgggagaaga actggcaatt agggagtttg tggagcttct aattacacac     300
cagcccctct gccaggagct ggtgcccgcc agccggggc aggctgccgg gagtacccag      360
ctccagctgg agacagtcag tgcctgagga tttgggggaa gcaggtgggg aaaccttggc     420
acagggctga caccttcctc tgtgccagag cccaggagct ggggcagcgt gggtgaccat     480
gtgggtgggc acgcttccct gctggggtg caggggtcc acgtggcagc ggccacctgg      540
agccctaatg tgcagcggtt aagagcaagc ccctggaagt cagagaggcc tggcatggag     600
tcttgcttct tgcaaacgag ccgtgtggag agagagatag taaatcaaca aagggaaata     660
catggtctgt ccgaggatga gctgccgag agcaatggtg aaagtgaagt gggggagggg      720
gcggggctgg gaggaaaagc cttgtgagaa ggtgacacga gagcacggcc ttgaagggga     780
agaaggaggg cactatggag gtcccggcga agcgtggcct ggccgaggaa cggcatgtgc     840
agaggtcctg ccgaggagct caagacaagt aggggacggt ggggctggag tggagagagt     900
gagtgggagg aggagtagga gtcagagagg agctcaggac agatccttta ggctctaggg     960
acacgataaa cacagtgttt tttgtcttgt caagtgtgtc cttttattt ttttgaaaga    1020 gtctcgctct gtagcccagg ctggagtgca gcggtgcgac ctcggctcac tgcaacctct    1080
gcctcccggg tccaagcaat tctcctgcct cagcctcccg agtagctggg attacaggca    1140
cccgccacca cgcactgcta attttttgtat tttagtagag accgggtttt gccatgttgg    1200
tcaggctggt ctcgaactcc tgacctcagg tgatccgccc gcctcggcct cccagagtgg    1260
tgtgagccac tatgccctgc agcacttgtc aagtctttct cagcgttccc ctcctctcca    1320
ctgcagctcc cagtgccca gtctgggcct cgtcttcact tcctgggatc cctgacattg    1380
cctgctaggc tctccctgtc tctggtctgg ctgccttcac tgtaacctcc acccagcagg    1440
tacctcttca gcacctccca tgaacccagc agaataccaa gccctgggga tgcagcaacg    1500
aacaggtaga cgctgcactc cagcctgggc gacagagcaa gactccgcct gaagaaaaaa    1560
aaaaggacca ggccgggcgc ggtggctcac gcctgtaatc ccagcacttt gggaggccga    1620
ggtgggtgga tcatgaggtc aggagttcaa gaccagcctg gccaaaatgg tgaaaccccg    1680
```

-continued

```
tctctactga aaatacaaa  aattagctgg gtgcagtggc gggcgcctgt agtctcagct    1740
actcaggagg ctgaggcagg ataattgctt gaccccagga ggcagaggtt gcagtgaacc    1800
gagatcacgc cactgcactc cagcctgggc gacagagcaa gactctgcct caaaaaaaag    1860
aataaaaata aaaaaaagga ccagatacag aaaacagaag gagacgtact atgaaggaaa    1920
ttggagagct tttgggatac tgagtaactc agggtggcct ttcccagggg acatttagct    1980
gagagataga cggtatgaag acctgaccgt tcagaaacag gggaagaggc agcagcccgg    2040
gcaaaggcct ttggggcagg aaagggcttg gatcactgga gaagcagaaa gatggccagt    2100
gtgaccagag tgtgacaaag tcagagaaaa ccaggaagat ggagctggag acacaggcgg    2160
ggccagatca cgagggtcct cgcagaccag agcaagggtt tggattttat tccaagtatg    2220
aagggaagct gctgaagtgt gttttccttt acaatttgta gttgaaatat aatatgcaaa    2280
gtacacaagt cttaactata tgtaagctta atgaatgttt ccatgaacca ataccgctg     2340 tgcaaccatc accagctcaa gagacgaacc cttctccctc ctcctgactg ccagtaacat    2400
agtggttcag ctcaagaaac agaactcttc tgacttcccc taacatagcg ggttttcttt    2460
tttgttttgt tttttgttgt tttttaagag acaatgtctt tattatttt atttttttt      2520 attttttgaga cggagtcttg ctgtcgccca ggctggagtg cagtggtgcg atctcggctc    2580
actgcaggct ctgcccccg gggttcatgc cattctcctg cctcagcctc cctagcagct    2640
gggactacag gtgcccgcca cctcgcccgg ctatttttt gtattttag tggagacggg     2700 gtttcaccgt gttagccagg atggtctcga tctcctgacc tcgtgatccg cccacctcgg    2760
cctcccaaag tgctgggatt acaggcatga gccaccgcgc ccagccaaga gacacggtct    2820
tgctctgtcg cccaggctgg atggagtgcc gtggtgcgat cacagctcgc ggcagccttg    2880
acatcctggg ctcaagcaac cttcctgcct tggcctccca aatgttggga ttataggcat    2940
gagccactgt gcttggcatc tattcatctt taatgtcaag caggcaattg aatatttgat    3000
cagggataga attgtctatt tgggggtatg cagatgtgct tcatgtcatg gaactgggcc    3060
gggcgcggtg gctcatgcct ataatcccag cactttggga ggccgaggca ggcggatcat    3120
aaggtcagga gatcgagacc atccgggcca acacggtgaa accccgtctc tactaaaaat    3180
acaaaaatta ggcaggtgtg gtggtgcgtg cctgtagtcc cagctactca gggaggctga    3240
gacaggagaa ttgattgaac ctgggaggca gaggttgtag tgagccaaga tcgcgccact    3300
gcactccagc ctgggcgaca tgagcgagac tccgtctcaa aaataaacaa aaaaagtca     3360 tggaattgat ggaaattgcc taaggggaga tgtagaagaa aagggtctc aggatcaagc      3420 cagcagagaa ggcagaaaag gtaaggtgtg tgaggtggca gaaaaggga agagtgtgga     3480 cagtgagggt ttcaaggagg aggaactgtc tactgcctcc tgccaaggac ggaggtgtcc    3540
actgccagtt gacataaggt cacccatgaa cttggtgaca ggaatttcag tggagaagtg    3600
gccacagaca caagtctaga attgaaatgg gagccgaggc agcgtagaca aaagaggaaa    3660
ctgctccttc cagagcggct ctgagcgagc accgagaaat gggcagtggc tttagggat     3720 gtagcgtcaa ggaagtgtct tttaaagaag tcggggccg gcacggtgg ctcacgcctg      3780 tagtcccagc actttgggag gccgaggcag gcagatcact tgaggtcagg agttcgagac    3840
cagcctggct aacacgatga aaccccgtct ctactaaaaa tacaaaaaat tagctgggca    3900
cggtggctcg tgcctgtaat cccagcactt tgggaggcag aggtgggcag atcacttgag    3960
gtcaggagtt tgagaccagc ctagccaaca tggtgaaacc ccatctctac taaaactaca    4020
```

-continued

```
aaaattagcc gggagtggtg gcacgtgcct gtaatcccag ccagtcagga ggctgaggca    4080
ggagaatcac tggaatcctg gaggtggagg tggcagtgag ccgagatggt acctctgtac    4140
tccagcctgg gggacagagt gagactccgt ctcaaaaaaa aaagaaggtg gggaaggatc    4200
tttgagggcc ggacacgctg accctgcagg agaggacaca ttcttctaac aggggtcgga    4260
caaaagagaa ctcttctgta taatttatga ttttaagatt tttatttatt attattttt     4320 atagaggcaa gcattttcca ccacgtcacc caggctggtc tccaactcct gggctcaagt    4380
gtgctgggat tatagccatg agtcaccaca cctgcccag aaactttact aaggacttat     4440
ttaaatgatt tgcttatttg tgaataggta ttttgttcac gtggttcaca actcaaaagc    4500
aacaaaaagc acccagtgaa aagccttcct ctcattctga tttccagtca ctggattcta    4560
ctcttgggat gcagtgtttt tcatctcttt tttgtatcct tttggaaata gtattctgct    4620
ttaaaaagca aatacaggcc aggtatggtg gctcactcct gtaatcccag cactttggga    4680
gccgaggcag gtgatcacct aaggtcagga gttcaagacc agcctggcca atatggtgaa    4740
accctgtctg taccaaaaca caaaaacaaa aacaaaaaca aaattagcc gggcgtggtg     4800 gcgtgctcct gtaatcccag ctactcagga ggctgaggca ggagaatcgc ttgaacctgg    4860
gaggcagagg ttgcagtgag ccgagattgt gccactgtac tccagcctgg gccacagagc    4920
aaggttccat ctcaaacaaa acaaaacaaa acaaacaaaa aaacaaaaca aaagctaata    4980
caaacacata tacaatagac aaaactgtaa atattttatt attttttattt tttttagtag   5040 agacaggggtt tcaccatgtt ggccaggatg gtctcaaact cctgacctca ggtgatccac    5100
ccacctcagc ctcccgatag ttaggattac aggcatgagc caccacaccc ggcctaaaat    5160
tgtaaacgtt ttagaagaaa gtatagatga atcccttcgt gatctcgggg aagaagagat    5220
tttttaaaaa agataccaaa agaagcacaa attataaaag aaaagattga aatgttggt     5280 gttaaaatta aaaacttgtt ttaaaacaag cttgtgtaac ccatgaccca caggctgcat    5340
gtggcccaga aaagctttga ctgcagccca acacaaattc gtaaactttc ctaaaacatt    5400
atgagatttt ttttgagatt ttgttttgtt ttgttttttg ttttttagc tcattcggta     5460 tcattaatgt tagcatattt tacgtggggc ccaagacaat tcttcttcca atgtgtctca    5520
ggggagccaa aagattggac acccctgcca taaacatgaa aagacaatgg ccgggcacgg    5580
tggctcacgc ctgtaatccc agcactttgg gaggctgagg ggggcgggat cacctgaggt    5640
caggagtttg agacaagcgt gaccaatgtg gtgaaaccct gtctctacta aaaatacaaa    5700
aattagccgg gcatgctcgt gcacacctat agtcccaact actcagcagg gtgaggcagg    5760
agaacctctt gaacccggga gcggaggtt gcagtgagcc gacattgcac ccctgcactc     5820
cagcctgggt gacagagtga gtctccactg gaaaaaaaaa aaaagaaca gtgtgataca    5880 ttgacctaag gtttaagaac atgcaaactg atactatata tcacttaggg acaaaaactt    5940
acatggtaaa agtaaaaaga aatgtacgaa aataataaaa atcaaattca agatggtggt    6000
tatggtgacg ggaagaact gaggcggaaa tataaggttg tcactatatt gagaaatttt     6060
tctatctttt tttctttttt cttttttttga gacgggtct cgctctgtcg cccaggatgg    6120
agtgcagtgg tgtgatctca gctcactgca acctccgcct cccaggttta agtgattctc    6180
ctgcctcaga ctcccaagta gctgggacta caggtgcgcg ccaacacacc tgggtaattt    6240
tgtttgtatt tttagtagag atgggggttc accgtgttga ctaggctggt ctcgaactcc    6300
tgacctcagg tgatccccg gcctcggtct cccaaagtgc tgggataaca agcgtgagcc    6360
actgcgccca gctttgtttg cattttagg tgagatgggg tttcaccacg ttggccaggc    6420
```

```
tggtcttgaa ctcctgacct caggtgatgc acctgcctca gtctcccaaa gtgctggatt      6480
acaggcgtta gccctgcgc ccggcccctg aaggaaaatc taaaggaaga ggaaggtgtg       6540
caaatgtgtg cgccttaggc gtaatggatg gtggtgcagc agtgggttaa agttaacacg      6600
agacagtgat gcaatcacag aatccaaatt gagtgcaggt cgctttaaga aaggagtagc      6660
tgtaatctga agcctgctgg acgctggatt agaaggcagc aaaaaaagct ctgtgctggc      6720
tggagccccc tcagtgtgca ggcttagagg gactaggctg ggtgtggagc tgcagcgtat      6780
ccacaggtaa agcagctccc ctggctgctc tgatgccagg gacggcggga gaggctcccc      6840
tgggctgggg ggacagggga gaggcagggg cactccaggg agcagaaaag aggggtgcaa      6900
gggagaggaa atgcggagac agcagcccct gcaatttggg caaaagggtg agtggatgag      6960
agagggcaga gggagctggg gggacaaggc cgaaggccag gacccagtga tccccaaatc      7020
ccactgcacc gacggaagag gctggaaagg cttttgaatg aagtgagtgg gaaacagcgg      7080
aggggcggtc atggggagga aagggagct aagctgctgg gtcgggtctg agcagcaccc       7140
caagactgga gcccgaggca aggaggctca cgggagctgc ttccaccaag ggcagtcagg      7200
aaggcggccg                                                              7210
```

<210> SEQ ID NO 11
<211> LENGTH: 1988
<212> TYPE: DNA
<213> ORGANISM: Homo sapiens
<220> FEATURE:
<221> NAME/KEY: misc_feature
<223> OTHER INFORMATION: JT8A - 2 kb PCR product using primers,
      SEQ ID:13 and 14; also referred to as JT108
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (542)..(542)
<223> OTHER INFORMATION: n is a, c, g, or t
<220> FEATURE:
<221> NAME/KEY: misc_feature
<222> LOCATION: (550)..(552)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (959)..(959)
<223> OTHER INFORMATION: n is a, c, g, or t
<220> FEATURE:
<221> NAME/KEY: misc_feature
<222> LOCATION: (1303)..(1303)
<223> OTHER INFORMATION: n is a, c, g, or t
<220> FEATURE:
<221> NAME/KEY: misc_feature
<222> LOCATION: (1307)..(1307)
<223> OTHER INFORMATION: n is a, c, g, or t
<220> FEATURE:
<221> NAME/KEY: misc_feature
<222> LOCATION: (1346)..(1349)
<223> OTHER INFORMATION: n is a, c, g, or t
<220> FEATURE:
<221> NAME/KEY: misc_feature
<222> LOCATION: (1393)..(1393)
<223> OTHER INFORMATION: n is a, c, g, or t
<220> FEATURE:
<221> NAME/KEY: misc_feature
<222> LOCATION: (1475)..(1475)
<223> OTHER INFORMATION: n is a, c, g, or t
<220> FEATURE:

```
<221> NAME/KEY: misc_feature
<222> LOCATION: (1491)..(1491)
<223> OTHER INFORMATION: n is a, c, g, or t
<220> FEATURE:
<221> NAME/KEY: misc_feature
<222> LOCATION: (1741)..(1741)
<223> OTHER INFORMATION: n is a, c, g, or t
<220> FEATURE:
<221> NAME/KEY: misc_feature
<222> LOCATION: (1915)..(1915)
<223> OTHER INFORMATION: n is a, c, g, or t
<220> FEATURE:
<221> NAME/KEY: misc_feature
<222> LOCATION: (1926)..(1926)
<223> OTHER INFORMATION: n is a, c, g, or t

<400> SEQUENCE: 11
```

| | | | | | |
|---|---|---|---|---|---|
| acaagctggc | agcggctgtc | tccaacttcg | gctatgacct | gtaccgggtg | cgatccagca | 60 |
| ngagccccac | gaccaacgtg | ctcctgtctc | ctctcagtgt | ggccacggcc | ctctcggccc | 120 |
| tctcgctggg | tgagtgctca | gatgcaggaa | gccccaggca | gacctggaga | ggcccctgt | 180 |
| ggcctctgcg | taaacgtggc | tgagtttatt | gacatttcag | ttcagcgagg | ggtgaagtag | 240 |
| caccaggggc | ctggcctggg | ggtcccagct | gtgtaagcag | gagctcaggg | gctgcacaca | 300 |
| cacgattccc | cagctccccg | aaaggggctg | ggcaccactg | acatggcgct | tggcctcagg | 360 |
| gttcgcttat | tgacacagtg | acttcaaggc | acattcttgc | attccttaac | caagctggtg | 420 |
| ctagcctagg | ttcctgggat | gtaactgcaa | acaagcaggt | gtgggcttgc | cctcaccgag | 480 |
| gacacagctg | ggttcacagg | ggaactaata | ccagctcact | acagaatagt | ctttttttt | 540 |
| tnttttttttn | nnctttctga | gacggagtct | cgctttgtcn | ccaaggctgg | agtgcagtgg | 600 |
| tgtgatctca | gctcactgca | acctctgcct | ccctggttca | aggaattctc | ctgcctcagc | 660 |
| ctccagagta | gctgggatta | caggcacctg | ccatcatgcc | cagctaattt | ttgtattttt | 720 |
| agtagagacg | gggtttcacc | atgttgccta | ggctggtctc | aaactcccgg | gctcaagcga | 780 |
| tccacccgcc | ttggcctccc | aaagtgctgg | gattacaggc | gtgagccacc | gcgcctggcc | 840 |
| agaataatct | taagggctat | gatgggagaa | gtacagggac | tggtacctct | cactccctca | 900 |
| ctcccacctt | ccaggcctga | tgcctttaac | ctacttcagg | aaaatctcta | aggatgaana | 960 |
| ttccttggcc | acctagattg | tcttgaagat | cagcctactt | gggctctcag | cagacaaaaa | 1020 |
| agatgagtat | agtgtctgtg | ttctgggagg | gggcttgatt | tggggccctg | gtgtgcagtt | 1080 |
| atcaacgtcc | acatccttgt | ctctggcagg | agcggagcag | cgaacagaat | ccatcattca | 1140 |
| ccgggctctc | tactatgact | tgatcagcag | cccagacatc | catggtacct | ataaggagct | 1200 |
| ccttgacacg | gtcactgccc | cccagaagaa | cctcaagagt | gcctcccgga | tcgtctttga | 1260 |
| gaagagtgag | tcgcctttgc | agcccaagtt | gcctgaggca | tgngggntcc | atgctgcagg | 1320 |
| ctgggggggt | cttttttttt | tttttnnnna | gacggagtct | cgctctgttg | cccaggctgg | 1380 |
| agtgcagtgg | cgngatctcg | gctcactgca | acctccacct | cccgggttca | caccatcctc | 1440 |
| ctgcctcagc | ctcccgagta | gctgggactg | caggngccca | gctaatcttt | nttgtatttt | 1500 |
| tagcagagac | ggggtttcac | cgtgtttgcc | aggatagtct | cgatctcctg | acctggtgtt | 1560 |
| ctgcccgcct | cgacctccca | aagtgctggg | attacaggtg | tgagccaccg | cgctcggccc | 1620 |
| gtttctaaac | aatagatcat | gtgtgcccag | gcctggcctg | gcactggtgt | ggaggaaggg | 1680 |
| cccgtgagcc | caaagaggct | cagaaagagg | aagtgggctg | caggagacgg | tgggaggggc | 1740 |
| ngggagggca | gtgcgcgat | gtggggaaat | ctgctgcccc | cctggccagt | gcctgggat | 1800 |
| gccagcagaa | gtcctggcaa | gtcacaggaa | gatgctggct | gggaagtcag | ggcctgctga | 1860 |

-continued

| | |
|---|---|
| gcgctaaacc agaacccgag cctggcaggc tctcaaagac gggatgcttg tcgtngagtc | 1920 |
| tcatangcta acctctgctc cgcctcttct cagagctgcg cataaaatcc agctttgtgg | 1980 |
| cacctctg | 1988 |

<210> SEQ ID NO 12
<211> LENGTH: 3267
<212> TYPE: DNA
<213> ORGANISM: Homo sapiens
<220> FEATURE:
<221> NAME/KEY: misc_feature
<223> OTHER INFORMATION: JT019 - 3.3 kb PCR product using primers, SEQ ID NO: 15 and 16

<400> SEQUENCE: 12

| | |
|---|---|
| gattccagct ttgtggcacc tctggaaaag tcatatggga ccaggcccag agtcctgacg | 60 |
| ggcaaccctc gcttggacct gcaagagatc aacaactggg tgcaggcgca gatgaaaggg | 120 |
| aagctcgcca ggtccacaaa ggaaattccc gatgagatca gcattctcct tctcggtgtg | 180 |
| gcgcacttca agggtgagcg cgtctccaat tctttttcat ttattttact gtattttaac | 240 |
| taattaatta attcgatgga gtcttactct gtagccctaa ctggagtgca gtggtgcgat | 300 |
| ctcagctcaa tgcaacctcc gcctcccagg ttcaagcaat tcttgtgcct cagcctcccg | 360 |
| agtagctggg attacaggga tgtaccacca ctcccggcta attttttgta tttaatagac | 420 |
| atggggtttc accatgttgg ccaggctggt ctcgaactcc tgagctcagg tggtctgccc | 480 |
| gcctcagcct cccaaagtgc taggattaca agcttgagcc accacgccca gccctttta | 540 |
| ttttaaatt aagagacaag gtgttgccat gatgcccagg ctggtctcga actcctgggc | 600 |
| tcaagtaatc ctcccacctt ggcctcccaa agtgctggga ttacaggcat gagccaccgc | 660 |
| gcccggccct tttacattta tttatttatt ttttgagaca gagtcttgct ctgtcaccca | 720 |
| ggctggagtg cagtggcgcg atctcggctc actgcaagct ctgccttcca ggttcacacc | 780 |
| attctcctgc ctcgacctcc cgagtagctg ggactacagg cgcccgccac tgcgccctac | 840 |
| taattttttg tatttttagt agagacgggg tttcaccgtg gtctcgatct cctgacctcg | 900 |
| tgatccaccc gcctcagcct cccaaagtgc tgggattaca ggcgtgagcc actgcgcccg | 960 |
| gccctttac atttattttt aaattaagag acagggtgtc actatgatgc cgaggctggt | 1020 |
| ctcgaactcc tgagctgaag tgatcctccc acctcggcct cccaaaatgc tgggattacc | 1080 |
| atgtccaact ttccacttct gttttgacca aggatggatg cagacatca gaagggagctt | 1140 |
| ggaaagggag gtgtcaaaga ccttgcccag catggagtct gggtcacagc tggggagga | 1200 |
| tctgggaact gtgcttgcct gaagcttacc tgcttgtcat caaatccaag gcaaggcgtg | 1260 |
| aatgtctata gagtgagaga cttgtggaga cagaagagca gagagggagg aagaatgaac | 1320 |
| ctgggtctgt ttgggctttt ccagctttt gagtcagaca agatttattt atttatttaa | 1380 |
| gatggagtct cattctgttg cccaggctgg agtgcagtgg tgccatcttg gctcactaca | 1440 |
| gcctccccac ctcccaggtt caagtgcttc tcctgcctca gcctcccgag tagttgggat | 1500 |
| tacaggcgcc cgccaccaca cccagctaat ttttgtattt tcagtagaga tggggtttcg | 1560 |
| ccatgctggc caggctgttc tcgaaaactc ctgacctcag atgatccacc cgcctcggcc | 1620 |
| tcccacagtg ctgggattac aggcgtgagc cactgcgctg gccaaatcag acaaggttta | 1680 |
| aatcccagct ctgcctgtac tagctgagga actctgcaca catttcataa cctttctggg | 1740 |
| cctacgttct cacctttaac gtgaggataa tatatctact tcatagacac cttttatgt | 1800 |

-continued

```
tgtctccaag ttttctaaca gctctagttc tgtacccaag acatggcagg tggccaacga    1860
catccttcta ggctgtggtg atgtgtttgg agcttgttcc acgggtcttg tgtggggcca    1920
gccctgttca gataaggcct tgtgggtgg cctgggtag ggggaggggt tgggcaaact      1980
ctcccttaaa acgctttgta accatctgag gcaccagcaa gagcggcccc cgagcctgga    2040
caaaatccaa acggcttcct acttcaagca ctgatgtcta gtgagtgaag gaacagctct    2100
gggtccagga tattataggt cacattaaac taaaggggct tggccatcag ctggcttcca    2160
gagcgtcagc cagttacttc acctctttgg ctttggcctg ttttcagcta caagaggact    2220
taatccagag gacctcagag gtccttccca gctcagacct tctttgactg tctcccagag    2280
acactgctgt aggagtgcac accagtttac ttttctttct tttgtttttg agatggagtt    2340
tcgctctttt tgcctaggct ggagtgctgt ggtgtgatct cagctcactg caacctctgg    2400
ctcccaggtt caagtgattc tcctgtctct gcctcccgag tagctgggat tacagacacc    2460
caccactgca cccggctagt ttttgtattt tcagtagaga tggggttcg ccatgctggc     2520 caggctgttc tcgaaaactc ctgacctcag atgatccatc cgccttggcc tcccaaagtg    2580
ctgagattac agatgtgagg caccacaccc ggccattttt gtattttag tagagacggg     2640 gttttgccat gttggccacg ctggtctcaa actcctgacc tcaagtgatc tgcccacctt    2700
ggcctcctga agggctggga ctacaggcgt gagtcaccgt gcccggccat ttttgtattt    2760
ttaggacagc gtttttttcat gttggccagg ctggtctcaa actcctgacc tcaagtgatc   2820
cacccacccc ggcctcccaa tatgctggga ttccaggtgt gagttaccat gcccggctac    2880
cactttactt ttcctgcagg ctatcacaga acgtgtacaa tctagactct aatcaaccaa    2940
atcaacgtct tgccatcgga gtttgctggt gaagggcact tggggtcctg gaaataactg    3000
taggctccaa gccacacaca ctgagatagg cctattccct gaggcctcag agccctgac     3060 agctaagctc ccttgagtcg ggcaattttc aacaacgtgc tctggggaca cagcatggcg    3120
ccactgtctt tctggtctcc tggggctcag actatgtcat acacttcttt ccagggcagt    3180
gggtaacaaa gtttgactcc agaaagactt ccctcgagga tttctacttg gatgaagaga    3240
ggaccgtgag ggtccccatg atgaatc                                        3267
```

<210> SEQ ID NO 13  
<211> LENGTH: 20  
<212> TYPE: DNA  
<213> ORGANISM: Artificial Sequence  
<220> FEATURE:  
<223> OTHER INFORMATION: oligonucleotide  
<220> FEATURE:  
<221> NAME/KEY: misc_feature  
<223> OTHER INFORMATION: 603 - primer in a polymerase chain reaction

<400> SEQUENCE: 13

```
acaagctggc agcggctgtc                                                  20
```

<210> SEQ ID NO 14  
<211> LENGTH: 20  
<212> TYPE: DNA  
<213> ORGANISM: Artificial Sequence  
<220> FEATURE:  
<223> OTHER INFORMATION: Oligonucleotide  
<220> FEATURE:  
<221> NAME/KEY: misc_feature  
<223> OTHER INFORMATION: 604 - primer in a polymerase chain reaction

<400> SEQUENCE: 14

```
cagaggtgcc acaaagctgg                                                  20
```

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<223> OTHER INFORMATION: 605 - primer in a polymerase chain reaction

<400> SEQUENCE: 15
ccagctttgt ggcacctctg                                        20

<210> SEQ ID NO 16
<211> LENGTH: 20
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<223> OTHER INFORMATION: 606 - primer in a polymerase chain reaction

<400> SEQUENCE: 16
catcatgggg accctcacgg                                        20

<210> SEQ ID NO 17
<211> LENGTH: 20
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<223> OTHER INFORMATION: 2213- primer in a polymerase chain reaction

<400> SEQUENCE: 17
aggatgcagg ccctggtgct                                        20

<210> SEQ ID NO 18
<211> LENGTH: 20
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<223> OTHER INFORMATION: 2744 - primer in a polymerase chain reaction

<400> SEQUENCE: 18
cctcctccac cagcgcccct                                        20

<210> SEQ ID NO 19
<211> LENGTH: 24
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<223> OTHER INFORMATION: 2238 - primer in a polymerase chain reaction

<400> SEQUENCE: 19
atgatgtcgg accctaaggc tgtt                                   24

<210> SEQ ID NO 20
<211> LENGTH: 20

```
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<223> OTHER INFORMATION: 354 - primer in a polymerase chain reaction

<400> SEQUENCE: 20
tggggacagt gaggaccgcc                                                    20

<210> SEQ ID NO 21
<211> LENGTH: 24
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<223> OTHER INFORMATION: JT10-UP01 - primer in a polymerase chain
      reaction

<400> SEQUENCE: 21
ggtgtgcaaa tgtgtgcgcc ttag                                               24

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<223> OTHER INFORMATION: JT10-DP01 - primer in a polymerase chain
      reaction

<400> SEQUENCE: 22
gggagctgct ttacctgtgg atac                                               24

<210> SEQ ID NO 23
<211> LENGTH: 25
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<223> OTHER INFORMATION: 1590 - primer in a polymerase chain reaction

<400> SEQUENCE: 23
ggacgctgga ttagaaggca gcaaa                                              25

<210> SEQ ID NO 24
<211> LENGTH: 19
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<223> OTHER INFORMATION: 1591 - primer in a polymerase chain reaction

<400> SEQUENCE: 24
ccacacccag cctagtccc                                                     19

<210> SEQ ID NO 25
<211> LENGTH: 18
<212> TYPE: DNA
<213> ORGANISM: Artificial Sequence
```

```
<220> FEATURE:
<223> OTHER INFORMATION: Oligonucleotide
<220> FEATURE:
<221> NAME/KEY: misc_feature
<222> LOCATION: (9)..(10)
<223> OTHER INFORMATION: 5' splice site of EXON 1- 5' splice donor site

<400> SEQUENCE: 25
tatccacagg taaagtag                                                18

<210> SEQ ID NO 26
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (9)..(10)
<223> OTHER INFORMATION: 5' splice site of EXON 2 - 5' splice donor site

<400> SEQUENCE: 26
ccggaggagg tcagtagg                                                18

<210> SEQ ID NO 27
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (9)..(10)
<223> OTHER INFORMATION: 5' splice site of EXON 3 - 5' splice donor site

<400> SEQUENCE: 27
tctcgctggg tgagtgct                                                18

<210> SEQ ID NO 28
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (9)..(10)
<223> OTHER INFORMATION: 5' splice site of EXON 4 - 5' splice donor site

<400> SEQUENCE: 28
ttgagaagag tgagtcgc                                                18

<210> SEQ ID NO 29
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (9)..(10)
<223> OTHER INFORMATION: 5' splice site of EXON 5 - 5' splice donor site

<400> SEQUENCE: 29
acttcaaggg tgagcgcg                                                18

<210> SEQ ID NO 30
<211> LENGTH: 18
<212> TYPE: DNA
```

```
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (9)..(10)
<223> OTHER INFORMATION: 5' splice site of EXON 6 - 5' splice donor site

<400> SEQUENCE: 30
agctgcaagg tctgtggg                                                    18

<210> SEQ ID NO 31
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (9)..(10)
<223> OTHER INFORMATION: 5' splice site of EXON 7 - 5' splice donor site

<400> SEQUENCE: 31
aggagatgag tatgtctg                                                    18

<210> SEQ ID NO 32
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (9)..(10)
<223> OTHER INFORMATION: 5' splice site of EXON 8 - 5' splice donor site

<400> SEQUENCE: 32 tttatccta acttctgt                                                     18

<210> SEQ ID NO 33
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (9)..(9)
<223> OTHER INFORMATION: 3' splice site of INTRON 1 - 3' splice acceptor
      site

<400> SEQUENCE: 33 ggacgctgg                                                               9

<210> SEQ ID NO 34
<211> LENGTH: 18
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (9)..(10)
<223> OTHER INFORMATION: 3' splice site of INTRON 2 - 3' splice acceptor
      site

<400> SEQUENCE: 34
ttcttgcagg ccccagga                                                    18
```

<210> SEQ ID NO 35
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: 3' splice site of INTRON 3 - 3' splice acceptor
      site

<400> SEQUENCE: 35
tcctgccagg gctcccca                                                   18

<210> SEQ ID NO 36
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (9)..(10)
<223> OTHER INFORMATION: 3' splice site of INTRON 4 - 3' splice acceptor
      site

<400> SEQUENCE: 36
ctctggcagg agcggacg                                                   18

<210> SEQ ID NO 37
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (9)..(10)
<223> OTHER INFORMATION: 3' splice acceptor site

<400> SEQUENCE: 37
tcttctcaga gctgcgca                                                   18

<210> SEQ ID NO 38
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (9)..(10)
<223> OTHER INFORMATION: 3' splice acceptor site

<400> SEQUENCE: 38
tctttccagg gcagtggg                                                   18

<210> SEQ ID NO 39
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (9)..(10)
<223> OTHER INFORMATION: 3' splice acceptor site

<400> SEQUENCE: 39
ttgtctcaga ttgcccag                                                   18

<210> SEQ ID NO 40
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (9)..(10)
<223> OTHER INFORMATION: 3' splice acceptor site

<400> SEQUENCE: 40

| | |
|---|---|
| tctctacaga gctgcaat | 18 |

<210> SEQ ID NO 41
<211> LENGTH: 737
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (614)..(728)
<223> OTHER INFORMATION: Exon of PEDF GENE

<400> SEQUENCE: 41

| | |
|---|---|
| ttctttttt gagacggggt ctcgctctgc tcgcccagga tggagtgcag tggtgtgatc | 60 |
| tcagctcact gcaacctccg cctcccaggt ttaagtgatt ctcctgcctc agactcccaa | 120 |
| gtagctggga ctacaggtgc gcgccaacac acctgggtaa ttttgtttgt attttagta | 180 |
| gagatggggt ttcaccgtgt tgactaggct ggtctcgaac ctcctgacct caggtgatcc | 240 |
| cccggcctcg gtctcccaaa gtgctgggga taacaagcgt gagccactgc gcccagcttt | 300 |
| gtttgcattt ttaggtgaga tggggtttca ccacgttggc caggctggtc ttgaactcct | 360 |
| gacctcaggt gatgcacctg cctcagtctc ccaaagtgct ggattacagg cgttagcccc | 420 |
| tgcgcccggc ccctgaagga aaatctaaag gaagaggaag gtgtgcaaat gtgtgcgcct | 480 |
| taggcgtaat ggatggtggt gcagcagtgg gttaaagtta acacgagaca gtgatgcaat | 540 |
| cacaggaatc caaattgagt gcaggtcgct ttaagaaagg agtagctgta atctgaagcc | 600 |
| atctgaagcc tgctggacgc tggattagaa ggcagcaaaa aaagctctgt gctggctgga | 660 |
| gcccctcag tgcaggctta gagggactag gctgggtgtg gagctgcagc gtatccacag | 720 |
| gccccagggt aaagtag | 737 |

<210> SEQ ID NO 42
<211> LENGTH: 88
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (9)..(88)
<223> OTHER INFORMATION: Exon of PEDF GENE

<400> SEQUENCE: 42

| | |
|---|---|
| ttcttgcaga tgcaggccct ggtgctactc ctctgcattg gagccctcct cgggcacagc | 60 |
| agctgccaga accctgccag ccccccgg | 88 |

<210> SEQ ID NO 43
<211> LENGTH: 22480
<212> TYPE: DNA

-continued

```
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: P1-147 Full length genomic sequence for PEDF
      plus flanking sequences
<220> FEATURE:
<221> NAME/KEY: misc_feature
<222> LOCATION: (15139)..(15139)
<223> OTHER INFORMATION: n is a, c, g, or t
<220> FEATURE:
<221> NAME/KEY: misc_feature
<222> LOCATION: (15147)..(15149)
<223> OTHER INFORMATION: n is a, c, g, or t
<220> FEATURE:
<221> NAME/KEY: misc_feature
<222> LOCATION: (15177)..(15177)
<223> OTHER INFORMATION: n is a, c, g, or t
<220> FEATURE:
<221> NAME/KEY: misc_feature
<222> LOCATION: (16072)..(16072)
<223> OTHER INFORMATION: n is a, c, g, or t
<220> FEATURE:
<221> NAME/KEY: misc_feature
<222> LOCATION: (16088)..(16088)
<223> OTHER INFORMATION: n is a, c, g, or t
<220> FEATURE:
<221> NAME/KEY: misc_feature
<222> LOCATION: (20830)..(20830)
<223> OTHER INFORMATION: n is a, c, g, or t

<400> SEQUENCE: 43
gcggccgcag ggtggactgt gctgaggaac cctgggccca gcaggggtgg cagcccgcgc        60
agtgccacgt ttggcctctg ccgctcgcc aggcatcctc caccccgtgg tccctctga        120 cctcgccagc cctccccgg gacacctcca cgccagcctg gctctgctcc tggcttcttc        180
ttctctctat gcctcaggca gccggcaaca gggcggctca aacagcgcc agcctcctgg        240 tttgggagaa gaactggcaa ttagggagtt tgtggagctt ctaattacac accagccct        300 ctgccaggag ctggtgcccg ccagccgggg gcaggctgcc gggagtaccc agctccagct        360
ggagacagtc agtgcctgag gatttggggg aagcaggtgg ggaaaccttg cacagggct        420 gacaccttcc tctgtgccag agcccaggag ctggggcagc gtgggtgacc atgtgggtgg        480
gcacgcttcc ctgctggggg tgcagggggt ccacgtggca gcggccacct ggagccctaa        540
tgtgcagcgg ttaagagcaa gcccctggaa gtcagagagg cctggcatgg agtcttgctt        600
cttgcaaacg agccgtgtgg agagagagat agtaaatcaa caaagggaaa tacatggtct        660
gtccgaggat gagctgccgg agagcaatgg tgaaagtgaa gtggggagg gggcggggct        720 gggaggaaaa gccttgtgag aaggtgacac gagagcacgg ccttgaaggg gaagaaggag        780
ggcactatgg aggtcccggc gaagcgtggc ctggccgagg aacggcatgt gcagaggtcc        840
tgccgaggag ctcaagacaa gtaggggacg gtggggctgg agtggagaga gtgagtggga        900
ggaggagtag gagtcagaga ggagctcagg acagatcctt taggctctag ggacacgata        960
aacacagtgt ttttttgtctt gtcaagtgtg tccttttat tttttgaaa gagtctcgct        1020 ctgtagccca ggctggagtg cagcggtgcg acctcggctc actgcaacct ctgcctcccg        1080
ggtccaagca attctcctgc ctcagcctcc cgagtagctg ggattacagg cacccgccac        1140
cacgcactgc taattttgt atttagtag agaccgggtt ttgccatgtt ggtcaggctg        1200
gtctcgaact cctgacctca ggtgatccgc ccgcctcggc ctcccagagt ggtgtgagcc        1260
actatgccct gcagcacttg tcaagtcttt ctcagcgttc ccctcctctc cactgcagct        1320
cccagtgccc cagtctgggc ctcgtcttca cttcctggga tccctgacat tgcctgctag        1380
```

```
gctctccctg tctctggtct ggctgccttc actgtaacct ccacccagca ggtacctctt   1440
cagcacctcc catgaaccca gcagaatacc aagccctggg gatgcagcaa cgaacaggta   1500
gacgctgcac tccagcctgg gcgacagagc aagactccgc ctgaagaaaa aaaaaaggac   1560
caggccgggc gcggtggctc acgcctgtaa tcccagcact ttgggaggcc gaggtgggtg   1620
gatcatgagg tcaggagttc aagaccagcc tggccaaaat ggtgaaaccc cgtctctact   1680
gaaaaataca aaaattagct gggtgcagtg gcgggcgcct gtagtctcag ctactcagga   1740
ggctgaggca ggataattgc ttgacccag gaggcagagg ttgcagtgaa ccgagatcac   1800
gccactgcac tccagcctgg gcgacagagc aagactctgc ctcaaaaaaa agaataaaaa   1860
taaaaaaaag gaccagatac agaaaacaga aggagacgta ctatgaagga aattggagag   1920
cttttgggat actgagtaac tcagggtggc ctttcccagg ggacatttag ctgagagata   1980
gacggtatga agacctgacc gttcagaaac aggggaagag gcagcagccc gggcaaaggc   2040 cttggggca ggaaagggct tggatcactg gagaagcaga aagatggcca gtgtgaccag   2100
agtgtgacaa agtcagagaa aaccaggaag atggagctgg agacacaggc ggggccagat   2160
cacgagggtc ctcgcagacc agagcaaggg tttggatttt attccaagta tgaagggaag   2220
ctgctgaagt gtgttttcct ttacaatttg tagttgaaat ataatatgca agtacacaa   2280 gtcttaacta tatgtaagct taatgaatgt ttccatgaac caaataccgc tgtgcaacca   2340
tcaccagctc aagagacgaa cccttctccc tcctcctgac tgccagtaac atagtggttc   2400
agctcaagaa acagaactct tctgacttcc cctaacatag cgggttttct tttttgtttt   2460 gtttttgtt gtttttttaag agacaatgtc tttattattt ttattttttt ttattttttga  2520 gacggagtct tgctgtcgcc caggctggag tgcagtggtg cgatctcggc tcactgcagg   2580
ctctgccccc cggggttcat gccattctcc tgcctcagcc tccctagcag ctgggactac   2640
aggtgcccgc cacctcgccc ggctattttt ttgtattttt agtggagacg gggtttcacc   2700
gtgttagcca ggatggtctc gatctcctga cctcgtgatc cgcccacctc ggcctcccaa   2760
agtgctggga ttacaggcat gagccaccgc gcccagccaa gagacacggt cttgctctgt   2820
cgcccaggct ggatggagtg ccgtggtgcg atcacagctc gcggcagcct tgacatcctg   2880
ggctcaagca accttcctgc cttggcctcc caaatgttgg gattataggc atgagccact   2940
gtgcttggca tctattcatc tttaatgtca agcaggcaat tgaatatttg atcagggata   3000
gaattgtcta tttgggggta tgcagatgtg cttcatgtca tggaactggg ccgggcgcgg   3060
tggctcatgc ctataatccc agcactttgg gaggccgagg caggcggatc ataaggtcag   3120
gagatcgaga ccatccgggc caacacggtg aaaccccgtc tctactaaaa atacaaaaat   3180
taggcaggtg tggtggtgcg tgcctgtagt cccagctact cagggaggct gagacaggag   3240
aattgattga acctgggagg cagaggttgt agtgagccaa gatcgcgcca ctgcactcca   3300
gcctgggcga catgagcgag actccgtctc aaaaataaac aaaaaaagt catggaattg   3360 atggaaattg cctaagggga gatgtagaag aaagggtc tcaggatcaa gccagcagag   3420
aaggcagaaa aggtaaggtg tgtgaggtgg cagaaaaagg gaagagtgtg gacagtgagg   3480
gtttcaagga ggaggaactg tctactgcct cctgccaagg acggaggtgt ccactgccag   3540
ttgacataag gtcacccatg aacttggtga caggaatttc agtggagaag tggccacaga   3600
cacaagtcta gaattgaaat gggagccgag gcagcgtaga caaaagagga aactgctcct   3660
tccagagcgg ctctgagcga gcaccgagaa atgggcagtg gctttagggg atgtagcgtc   3720
```

-continued

```
aaggaagtgt cttttaaaga agtcgggggc cgggcacggt ggctcacgcc tgtagtccca    3780
gcactttggg aggccgaggc aggcagatca cttgaggtca ggagttcgag accagcctgg    3840
ctaacacgat gaaacccgt ctctactaaa aatacaaaaa attagctggg cacggtggct     3900
cgtgcctgta atcccagcac tttgggaggc agaggtgggc agatcacttg aggtcaggag    3960
tttgagacca gcctagccaa catggtgaaa ccccatctct actaaaacta caaaaattag    4020
ccgggagtgg tggcacgtgc ctgtaatccc agccagtcag gaggctgagg caggagaatc    4080
actggaatcc tggaggtgga ggtggcagtg agccgagatg gtacctctgt actccagcct    4140
gggggacaga gtgagactcc gtctcaaaaa aaaagaagg tggggaagga tctttgaggg     4200
ccggacacgc tgaccctgca ggagaggaca cattcttcta acaggggtcg gacaaaagag    4260
aactcttctg tataatttat gattttaaga tttttattta ttattatttt ttatagaggc    4320
aagcattttt caccacgtca cccaggctgg tctccaactc ctgggctcaa gtgtgctggg    4380
attatagcca tgagtcacca cacctggccc agaaacttta ctaaggactt atttaaatga    4440
tttgcttatt tgtgaatagg tattttgttc acgtggttca caactcaaaa gcaacaaaaa    4500
gcacccagtg aaaagccttc ctctcattct gatttccagt cactggattc tactcttggg    4560
atgcagtgtt tttcatctct tttttgtatc cttttggaaa tagtattctg ctttaaaaag    4620
caaatacagg ccaggtatgg tggctcactc ctgtaatccc agcactttgg gaggccgagg    4680
caggtgatca cctaaggtca ggagttcaag accagcctgg ccaatatggt gaaaccctgt    4740
ctgtaccaaa acacaaaaac aaaaacaaaa acaaaaatta gccgggcgtg gtggcgtgct    4800
cctgtaatcc cagctactca ggaggctgag gcaggagaat cgcttgaacc tgggaggcag    4860
aggttgcagt gagccgagat tgtgccactg tactccagcc tgggccacag agcaaggttc    4920
catctcaaac aaaacaaaac aaaacaaaca aaaaacaaa acaaaagcta atacaaacac    4980
atatacaata gacaaaactg taaatatttt attattttta tttttttag tagagacagg     5040 gttccaccat gttggccagg atggtctcaa actcctgacc tcaggtgatc cacccacctc    5100
agcctcccga tagttaggat tacaggcatg agccaccaca cccggcctaa aattgtaaac    5160
gttttagaag aaagtataga tgaatccctt cgtgatctcg gggaagaaga gatttttaa    5220 aaaagatacc aaaagaagca caaattataa agaaaagat tgaaaatgtt ggtgttaaaa     5280
ttaaaaactt gttttaaaac aagcttgtgt aacccatgac ccacaggctg catgtggccc    5340
agaaaagctt tgactgcagc ccaacacaaa ttcgtaaact ttcctaaaac attatgagat    5400
tttttttgag attttgtttt gttttgtttt ttgtttttt agctcattcg gtatcattaa     5460
tgttagcata tttacgtgg gcccaagac aattcttctt ccaatgtgtc tcaggggagc      5520
caaaagattg acaccctg ccataaacat gaaaagacaa tggccgggca cggtggctca      5580
cgcctgtaat cccagcactt tgggaggctg aggggggcgg gatcacctga ggtcaggagt    5640
ttgagacaag cgtgaccaat gtggtgaaac cctgtctcta ctaaaatac aaaaattagc     5700 cgggcatgct cgtgcacacc tatagtccca actactcagc agggtgaggc aggagaacct    5760
cttgaacccg ggaagcggag gttgcagtga gccgacattg caccctgca ctccagcctg     5820 ggtgacagag tgagtctcca ctggaaaaaa aaaaaaaga acagtgtgat acattgacct    5880
aaggtttaag aacatgcaaa ctgatactat atatcactta gggacaaaaa cttacatggt   5940
aaaagtaaaa agaaatgtac gaaaataata aaaatcaaat tcaagatggt ggttatggtg    6000
acgggaaaga actgaggcgg aaatataagg ttgtcactat attgagaaat ttttctatct    6060 tttttttcttt tttcttttt tgagacgggg tctcgctctg tcgcccagga tggagtgcag    6120
```

-continued

```
tggtgtgatc tcagctcact gcaacctccg cctcccaggt ttaagtgatt ctcctgcctc    6180
agactcccaa gtagctggga ctacaggtgc gcgccaacac acctgggtaa ttttgtttgt    6240
atttttagta gagatggggt ttcaccgtgt tgactaggct ggtctcgaac tcctgacctc    6300
aggtgatccc ccggcctcgg tctcccaaag tgctgggata caagcgtga gccactgcgc    6360 ccagctttgt ttgcattttt aggtgagatg gggtttcacc acgttggcca ggctggtctt    6420
gaactcctga cctcaggtga tgcacctgcc tcagtctccc aaagtgctgg attacaggcg    6480
ttagcccctg cgcccggccc ctgaaggaaa atctaaagga agaggaaggt gtgcaaatgt    6540
gtgcgcctta ggcgtaatgg atggtggtgc agcagtgggt taaagttaac acgagacagt    6600
gatgcaatca cagaatccaa attgagtgca ggtcgcttta agaaaggagt agctgtaatc    6660
tgaagcctgc tggacgctgg attagaaggc agcaaaaaaa gctctgtgct ggctggagcc    6720
ccctcagtgt gcaggcttag agggactagg ctgggtgtgg agctgcagcg tatccacagg    6780
taaagcagct ccctggctgc tctgatgcca gggacggcgg gagaggctcc cctgggctgg    6840
ggggacaggg gagaggcagg ggcactccag ggagcagaaa agagggtgc aagggagagg    6900 aaatgcggag acagcagccc ctgcaatttg ggcaaaaggg tgagtggatg agagagggca    6960
gagggagctg gggggacaag gccgaaggcc aggacccagt gatccccaaa tcccactgca    7020
ccgacggaag aggctggaaa ggcttttgaa tgaagtgagt gggaaacagc ggaggggcgg    7080
tcatggggag gaaaggggag ctaagctgct gggtcgggtc tgagcagcac cccaagactg    7140
gagcccgagg caaggaggct cacgggagct gcttccacca agggcagtca ggaaggcggc    7200
cgccctgcag cccagccctg gcccctgctc cctcggctcc ctgctacttt ttcaaaatca    7260
gctggtgctg actgttaagg caatttccca gcaccaccaa accgctggcc tcggcgccct    7320
ggctgagggc tgggatggag acagctgggg tccttctagc cagcccccac ccactctctt    7380
tggctacatg agtcaaggct gggcgaccaa tgaggttgtg gcctccggca acaatgacc    7440 actatttagg ccggcaggtg tatagggcgt gggggcccag ctgccagtgc tggagacaag    7500
ggctgtccga gatgaaccct ttctgctgcc tgccaagcca ctgggagggg taggtctcag    7560
caggattccc agaaaccccg cccctgtcca gcctaggccc ccacccggt gttagctaac    7620 ccaacgttag cccccaggtt ccgtgggtt ggggggcagg gagtcctatt cttgggctg    7680 ctgcttctgg ggtgtgggga agtgcaactc cacggcaccc tgggctgact cattcagctt    7740
ctaaagcttc aggaaacatt gtttgggct gggtcaccat gggtgggcca gagaggaccc    7800
ctcaatcccc tccggagagc caggggaggg ggaggtgccc ttccccatgc tatctccgag    7860
gcccactgcc atgtggctga aggctgtgcg gttctgggaa gaggggagg tggcggtgga    7920 ggctgtttgt ctcctaactg ggcttaatct gaaacacatg tattggcttg agttgatccg    7980
cctcacgtgg aggcaagatc acaaaagctt ctgtgtttct tgatgtgggc aattgtcaga    8040
aaataaggcc tgaccttggc ccagcaggga gggtatctac ctctccctga gccctccccc    8100
gcctgctagg acgagagcgg ggcttggata ctgcccttg acaggatgg catcattgtc    8160 tgtggctgca gccagccagc ggtcgcctgc tcagcccatg agcaaccact gtggacaggg    8220
tattgcgtgt gtgctgaggg gcgtccatgc agaccccac gcttgccctc tcactgccct    8280
tgtagggttt tcaatcatct ctcctcttcc cttatccaga tggcttgaag tggaggattc    8340
agacttgccg ttaatactct gggtcccgt gtctagctcg gggccacctt tggacccatg    8400
tcccttccct gccaggctcc ctcacctcac ctcagcctac ccacattgtg acaatcatct    8460
```

-continued

```
accacctgat ctgggqtttg ggcttagatt ctgtaggcac caagactaaa gtcgctcctt   8520
caagtccatt tgaattgtga ctttagtttc cttaaatact atgccaggat aatggccagg   8580
gatggtggct cacgcctgta ctcctggcac tttgggatgc tggtggatca cctgagatca   8640
ggattccagg ccagcctggc caacacggtg aaaccccatc tctactaaaa cataaaaatt   8700
aaccaggtgt ggtggcgggc acctgtaatc ccagctactc aggagactga ggcaggagaa   8760
ttgcttgaac ccgggaggtg gaagttgcac tgagctgaga tcgcgccact gcactttagc   8820
ctgggcgaca agagtgaaac tctgtctcaa aaacaaaaaa aactatgccg ggatgagcct   8880
gtctcctccc ttaatttctt acttgggcca gaggaactag aactaacaac ttctcttcta   8940
gccttgcctc ctgtgtacct cactgaattt ttggtctcta ataaaccagt ctgcagaggc   9000
tcaggggagg caggctcctg gcagctgggt ggggctggcc ccagccgggt ggagaccagc   9060
tgtaggcctg gatggtggtg aggcctctgt cttgcactgc agaaagcttt tcctgttgtc   9120
tacacgaaag ttttctccct gcatgtcagg gcagccacgt gcaagagcag ctggctggga   9180
acgcagaggt ctgcggctcg aggcggggtt tagaaagaaa accaggctgc ttcctgctgc   9240
ccgtcctgcc ttaagctgag taaactcaaa ggcaatcttc tttcatgcct cacgatattg   9300
tccagtggat tatctgattt aatttgaagg acgagagcca acaatcacac aacgtcctcc   9360
caaattttct gatccacttt gttctgggaa gtcaaaaagt gcgtgtgctg tgtgggtgga   9420
tgtttgtgta tataaatgga taatgaagga tgatgtgttg ggggccaggg caggggagac   9480
aacgctgttc agattctaca ttttttttttc ctttttttttt tttttttgag atggagtctt   9540
gctctgttgc ccagcctgga gtgcagtggc gcgatctcag ctcactgcaa cctccacttc   9600
ctggattcaa gtgattctcc tgccttagcc tcccaagtag ctgggattac aggcatgcgc   9660
caccacaccc ggctaatttt tgtatttttta gtagagatgg ggtttctcca tgttggccag   9720
gatggtctca aactcctgac ctcaggtgat ctacccgcct cggcctctca aagtgctggg   9780
attacaggtt tgagccactg cgcctggcct ttttttttttt ttttgagatg gagttttcac   9840
tcttgttgcc caggctggag tgcagtggtg cgatcttggc tcactgcaac ctccacctcc   9900
caagttcaag tgattctcca gccttagccc tccaagtagc tgggactaca ggtgtgtgcc   9960
accatgcctg gctatttttat tttattttat tttattttatt tattttttgag actaagtctt  10020 gctctgttgc ccagcctgga gtgcagtggc ataatcggct cactgcaacc tctgcctccc  10080
aggttcaagt gattctcctg cctcagcctc ctgagtaact gggattacag gggcctgcca  10140
ccacgcctgg ctacttttttg tatttttagt atagatgggg tttcaccatg ttggccaggc  10200
tggtctcgaa ctcctgacct caggctatcg gcctgcctca gcctcccaaa gtgctgggat  10260
tacaggcatg agccactgtg ctcggtagtt gttttatttt aatagtaggt tattttattt  10320
ccattttaca agagaaaaaa tggtgattta aagagctact aagacacagc actgagacca  10380
tgtgtgatgg catgcgcctg cagtcccagc tactcacgag gctgaggcag gaggatcaca  10440
tgaggtcagg agttccaggc tgtggagtgc tatggttgtg tagtgaatag ccactacact  10500
ccagcctggg cagcacagca agatcttgtc tcccaaaaaa aaaaaaaaaa aaaatttca  10560 aatgtgaacc caggatctct gaccctaggc cctgcactcc taaccatggg aggaagagct  10620
cttgaaaggg aactgtggga gagggaatg agctgccttg tgaggccaca gaagtccaaa  10680
gacagcttga gaatttggag ggacagcacg tgccggactg ggtgcctcta gcttggtat  10740 ccggtgattc catggaggag acctgggttc tgccccattc tcctggggag ggttgcccaa  10800
agtcttatca ccggagtggg tcagctgcct ccaggacaaa gctttagcat acacttgtgc  10860
```

-continued

```
tgggccatac tccacgtgga gaagccctgc tggggctggg gccccactgc tctggatctt    10920
taaaagctat tggttcaggg gccaggtgta atggctcaca cctataaccc tagcactttg    10980
ggaggctgaa gcaggtggat agcctgaggt caggagtttg agacaagcct gatgaacgtg    11040
gtgaaacccc atcgctatta aaatacaaaa aattagccgg gcatggtggc aggtgcctgt    11100
aattccagct acttgggagg ctgaggcggg agaatcgctt gaacccagga ggcggaggtt    11160
gcagtgagcc aagatcgctc cactgtactc cagcctgggc gacagagcca gactctgttt    11220
caaaaaataa aatataaata aataaataaa taaataaata aataaataaa agctttaggc    11280
ttaaaggagg gtcccctgac gcagacagtg gaacaaaagc acaagcttat ggtatgactg    11340
tgggccctga ggcagggga gggcggag aaccttgctg gagggatgg gccatcaagc       11400
tgagggtcca cttctgggg cctggagggg tgagggtgg tcgctgcagg gggtggggga    11460
aagtgactag ccctgcccaa cccctgggtc ctggctgggg tggccaggaa ggggtagcgg    11520
ggcagtgcag tgtcggggga gagcggcttg ctgcctcgtt cttttcttgc aggccccagg    11580
atgcaggccc tggtgctact cctctgcatt ggagccctcc tcgggcacag cagctgccag    11640
aaccctgcca gccccccgga ggaggtcagt aggcaggcgg ggagggcgtg gtcagcattc    11700
cccgcccctc cttggcaggc agcacgggaa acaggacagg gaacccggac ccaggttcca    11760
ggccaggctt gggcctttat ttctctaggg ctggagtttc tccagcagca aaacagagag    11820
aaaatgtctt gccttgcctt tcaggggatg gagtagggac atgaataaga tcccaaaaga    11880
gtaaaaatct gaagcacttt taacaagtcc agggcaattc tcctgcctca gcttcccaag    11940
cagctgggat tacaggcatg caccaccaag cccggctcat tttgtatttt tagtagagac    12000
ggggtttctc catgttggtc aggctggtct cgaactcccg acctcaagtg attctcctgc    12060
ctcggcctcc caaagtgccg ggatgacagg tgtgagccac cgcacctggc caggatcttt    12120
tctcattacc ttgtcttcct agtgggggct ccactgagca ggtcatgttc ccggacattt    12180
gttcggatac tgaccaggct gtggcaggga gtgagggtat ggagtgacct ctctcctgcc    12240
cagaaagggc gcagctgggt tcccaaggca gatacaggca catggaggga agcctgggcc    12300
atatgagtgt tatggggtga gtgttggcgg aggcccaccc ttgagggaca agagcagctg    12360
ggcatcttgg cgagagccct ggactttcgt gaggtcagag tatgaattct gcgtctccct    12420
cttcctagct ttgtgacccc agacaaccct tacctcagtc tttgcttcct tgcctatgaa    12480
atgggataaa aacacccatt ctacagggcc atgtggccac tcatttattt ctcatctacc    12540
aaacacctac tcgacagggg ctggcaatgg gcggaaataa aaactcagtt ctgccgggtg    12600
cggtggctca cacctgtaat cccagcagtg tgggaggcgg agcaggacga tcccttgaat    12660
ccaggagttt gagaccagca taggcaacat agtgagaccc ctgtctctac acaaaagcaa    12720
aaattaccag gcgtggtggc aagtgcttgt ggtactacct acttgggaag ctgaggtggg    12780
aggatcactt gagcccagga gattaagact gcagtgaggg gccggcgcg gtggctcacg    12840
cctgtaatcc cagcactttg ggaggtggag gtgggtggat cacgaggtca ggagatcgag    12900
accatcctgg ctaacacggt gaaaccccgt ctctactaaa aatacaaaaa attagctggg    12960
tgtggtgggg ggcgcctgta gtcccagcta ctcgggaggc tgaggcagga gaatggcgtg    13020
aacccgggag gtggaggttg cagtgagctg agctcgcacc actgcactcc agcctgggcg    13080
acagagtgag actccgtctc aaaaaaaaaa aaaaaaaaa gaaagaaaga aaaactgagt    13140
tcttttttttt aactttcttt tttttagagac agagtctcac tccatcaccc atgctggagt    13200
```

```
acagtggtgc gatcttggct cactgcaatc ttggcctcct gagttcaacc aattctcatg   13260
cctcagcctc ccaaatagct gggaccacag gcacgtgcca ccacgcccag ctaatttttt   13320
gggtattttt agtagagatg gggcctcacc atgttgctca ggttggtctg aaactcctga   13380
gctcaagtga tccatcttcc tcggcctgcc aaagtgctgg gattataggc ataagccact   13440
gcacctagct cccaattttt atatttatat ttatttttat ttacttattt attttttgag   13500
acagggtctc actctgtcac ccaggctgga gtacagtggc actatctcag ctcactgcaa   13560
cctctgcctc ctgggttcaa gcgaatctcg tgcctcagcc tcctgagtag ctgggattac   13620
aggcatgcac caccatgccc cgttaatttt tttgtatttt tagtagagac gggtttcacc   13680
gtgttgccca ggatggtctc gaactcctga cctcaagtga ttcacccacc tcagcctccc   13740
aaagtgctgg gattataggt gtgagccact cggctgatgg tttttaaaaa gtgggtcatg   13800
gggctgggcg cggtggctca tgcctgtaat cccagcactt tggtagaccg aggcgggtgg   13860
atcacaaggt caggagatcg agaccatcct gcctaacacg gtgaaacccc gtctctacta   13920
aaaatacaaa aaattaccca ggcatggtgg tgggcgcctg tagtcccagc tactcgggag   13980
gctgaggcag gagaatggcg tgaacctggg aggcggagct gcagtgagc cgagatcacg   14040 ccaccgtact ccagcctgag cgacagagcg agactccgtc tcaaaaaaaa aaaaaaaag   14100 tgggtcatag gtttcggctt ataggtcaca agtgtttaaa cctggccatg aggccaggcg   14160
cagtggcgca tgcctgtaat cccagccatt tgggaggcta aggcaggaaa atcgcttgaa   14220
ccggggaggt ggaggttgca gtgagctgag atcgcgccac tgaactctag cctgggtgac   14280
acagtaagac tctgtctcaa ataaaaaaaa aaacagctga tctctcttct gcgctgtctc   14340
tccacagaga gctcatgcgt gatcaggag taaaactcat tcccgtttta ggccaaacac   14400
agaaaaatta ggaaggacag ccccaagggg ccagaaccac caccctacac aaagccgtga   14460
ggagacagtc cctgtgcatc tctgcgagtc cctgaactca aacccaagac ttcctgtctc   14520
ctgccagggc tccccagacc ccgacagcac aggggcgctg gtggaggagg aggatccttt   14580
cttcaaagtc cccgtgaaca agctggcagc ggctgtctcc aacttcggct atgacctgta   14640
ccgggtgcga tccagcatga gccccacgac caacgtgctc ctgtctcctc tcagtgtggc   14700
cacggccctc tcggccctct cgctgggtga gtgctcagat gcaggaagcc ccaggcagac   14760
ctggagaggc cccctgtggc ctctgcgtaa acgtggctga gtttattgac atttcagttc   14820
agcgaggggt gaagtagcac caggggcctg gcctgggggt cccagctgtg taagcaggag   14880 ctcagggggct gcacacacac gattccccag ctccccgaaa ggggctgggc accactgaca   14940
tggcgcttgg cctcagggtt cgcttattga cacagtgact tcaaggcaca ttcttgcatt   15000
ccttaaccaa gctggtgcta gcctaggttc ctgggatgta actgcaaaca agcaggtgtg   15060
ggcttgccct caccgaggac acagctgggt tcacagggga actaatacca gctcactaca   15120
gaatagtctt ttttttttnt tttttttnnnc tttctgagac ggagtctcgc tttgtcncca   15180
aggctggagt gcagtggtgt gatctcagct cactgcaacc tctgcctccc tggttcaagg   15240
aattctcctg cctcagcctc cagagtagct gggattacag gcacctgcca tcatgcccag   15300 ctaattttg tatttttagt agagacgggg tttcaccatg ttgcctaggc tggtctcaaa   15360
ctcccgggct caagcgatcc acccgccttg gcctcccaaa gtgctgggat tacaggcgtg   15420
agccaccgcg cctggccaga ataatcttaa gggctatgat gggagaagta cagggactgg   15480
tacctctcac tccctcactc ccaccttcca ggcctgatgc cttttaaccta cttcaggaaa   15540 atctctaagg atgaaaattc cttggccacc tagattgtct tgaagatcag cctacttggg   15600
```

```
ctctcagcag acaaaaaaga tgagtatagt gtctgtgttc tgggaggggg cttgatttgg      15660
ggccctggtg tgcagttatc aacgtccaca tccttgtctc tggcaggagc ggagcagcga      15720
acagaatcca tcattcaccg ggctctctac tatgacttga tcagcagccc agacatccat      15780
ggtacctata aggagctcct tgacacggtc actgcccccc agaagaacct caagagtgcc      15840
tcccggatcg tctttgagaa gagtgagtcg cctttgcagc ccaagttgcc tgaggcatgt      15900
gggctccatg ctgcaggctg gggggtctt ttttttttt ggggaaagac ggagtctcgc       15960
tctgttgccc aggttggagt gaagtggcgt gatctcggtt cactgaaacc cccacctccc      16020
gggttcacac catcctcctg cctcagcctc ccgagtagct gggactgcag gngcccagct      16080
aatctttntt gtattttag cagagacggg gtttcaccgt gtttgccagg atagtctcga       16140
tctcctgacc tggtgttctg cccgcctcga cctcccaaag tgctgggatt acaggtgtga      16200
gccaccgcgc tcggcccgtt tctaaacaat agatcatgtg tgcccaggcc tggcctggca      16260
ctggtgtgga ggaagggccc gtgagcccaa agaggctcag aaagaggaag tgggctgcag      16320
gagacggtgg gaggggcagg gagggcagtg gcgcgatgtg gggaaatctg ctgccccct       16380 ggccagtgcc tggggatgcc agcagaagtc ctggcaagtc acaggaagat gctggctggg      16440
aagtcagggc ctgctgagcg ctaaaccaga acccgagcct ggcaggctct caaagacggg      16500
atgcttgtcg tcgagtctca tacgctaacc tctgctccgc ctcttctcag agctgcgcat      16560
aaaatccagc tttgtggcac ctctggaaaa gtcatatggg accaggccca gagtcctgac      16620
gggcaaccct cgcttggacc tgcaagagat caacaactgg gtgcaggcgc agatgaaagg      16680
gaagctcgcc aggtccacaa aggaaattcc cgatgagatc agcattctcc ttctcggtgt      16740
ggcgcacttc aagggtgagc gcgtctccaa ttctttttca tttatttac tgtattttaa       16800 ctaattaatt aattcgatgg agtcttactc tgtagcccta actggagtgc agtggtgcga      16860
tctcagctca atgcaacctc cgcctcccag gttcaagcaa ttcttgtgcc tcagcctccc      16920
gagtagctgg gattacaggg atgtaccacc actcccggct aattttttgt atttaataga      16980
catgggtttt caccatgttg gccaggctgg tctcgaactc ctgagctcag gtggtctgcc      17040
cgcctcagcc tcccaaagtg ctaggattac aagcttgagc caccacgccc agccctttt       17100 atttttaaat taagacaa ggtgttgcca tgatgcccag gctggtctcg aactcctggg       17160
ctcaagtaat cctcccacct tggcctccca agtgctggg attacaggca tgagccaccg       17220
cgcccggccc ttttacattt atttatttat tttttgagac agagtcttgc tctgtcaccc      17280
aggctggagt gcagtggcgc gatctcggct cactgcaagc tctgccttcc aggttcacac      17340
cattctcctg cctcgacctc ccgagtagct gggactacag gcgcccgcca ctgcgccctc      17400 taatttttg tatttttagt agagacgggg tttcaccgtg gtctcgatct cctgacctcg       17460
tgatccaccc gcctcagcct cccaaagtgc tgggattaca ggcgtgagcc actgcgcccg      17520
gcccttttac atttattttt aaattaagag acagggtgtc actatgatgc cgaggctggt      17580
ctcgaactcc tgagctgaag tgatcctccc acctcggcct cccaaaatgc tgggattacc      17640
atgtccaact ttcacttct tgtttgacca aggatggatg gcagacatca aagggcctt       17700 ggaaagggag gtgtcaaaga ccttgcccag catggagtct gggtcacagc tggggagga       17760 tctgggaact gtgcttgcct gaagcttacc tgcttgtcat caaatccaag gcaaggcgtg      17820
aatgtctata gagtgagaga cttgtggaga cagaagagca gagagggagg aagaatgaac      17880
actgggtctg tttgggcctt tcccagcttt tgagtcagac aagatttatt tatttattta      17940
```

-continued

```
agatggagtc tcattctgtt gcccaggctg gagtgcagtg gtgccatctt ggctcactac    18000
agcctcccca cctcccaggt tcaagtgctt ctcctgcctc agcctcccga gtagttggga    18060
ttacaggcgc ccgccaccac acccagctaa ttttttgtatt ttcagtagag atggggtttc    18120
gccatgctgg ccaggctgtt ctcgaaaact cctgacctca gatgatccac ccgcctcggc    18180
ctcccacagt gctgggatta caggcgtgag ccactgcgct ggccaaatca gacaaggttt    18240
aaatcccagc tctgcctgta ctagctgagg aactctgcac acatttcata accttctgg     18300 gcctacgttc tcacctttaa cgtgaggata atatatctac ttcatagaca ccttttatg      18360 ttgtctccaa gttttctaac agctctagtt ctgtacccaa gacatggcag gtggccaacg    18420
acatccttct aggctgtggt gatgtgtttg gagcttgttc cacgggtctt gtgtggggcc    18480
agccctgttc agataaggcc ttgtggggtg gcctgggta ggggagggg ttgggcaaac      18540 tctcccttaa aacgctttgt aaccatctga ggcaccagca agagcggccc ccgagcctgg    18600
acaaatccca aacggcttcc tacttcaagc actgatgtct agtgagtgaa ggaacagctc    18660
tgggtccagg atattatagg tcacattaaa ctaagggc ttggccatca gctggcttcc      18720
agagcgtcag ccagttactt caactctttg gctttggcct gttttcagct acaagaggac    18780
ttaatccaga ggacctcaga ggtccttccc agctcagacc ttctttgact gtctcccaga    18840
gacactgctg taggagtgca caccagttta cttttctttc ttttgttttt gagatggagt    18900
ttcgctcttt ttgcctaggc tggagtgctg tggtgtgatc tcagctcact gcaacctctg    18960
gctcccaggt tcaagtgatt ctcctgtctc tgcctcccga gtagctggga ttacagacac    19020
ccaccactgc acccggctag ttttttgtatt ttcagtagag atggggtttc gccatgctgg    19080
ccaggctgtt ctcgaaaact cctgacctca gatgatccat ccgccttggc ctcccaaagt    19140
gctgagatta cagatgtgag gcaccacacc cggccatttt tgtattttta gtagagacgg    19200
ggttttgcca tgttggccac gctggtctca aactcctgac ctcaagtgat ctgcccacct    19260
tggcctcctg aagggctggg actacaggcg tgagtcaccg tgcccggcca tttttgtatt    19320
tttaggacag cgtttttca tgttggccag gctggtctca aactcctgac ctcaagtgat    19380
ccacccaccc cggcctccca atatgctggg attccaggtg tgagttacca tgcccggcta    19440
ccactttact tttcctgcag gctatcacag aacgtgtaca atctagactc taatcaacca    19500
aatcaacgtc ttgccatcgg agtttgctgg tgaagggcac ttggggtcct ggaaataact    19560
gtaggctcca agccacacac actgagatag gcctattccc tgaggcctca gagcccctga    19620
cagctaagct cccttgagtc gggcaatttt caacaacgtg ctctggggac acagcatggc    19680
gccactgtct ttctggtctc ctggggctca gactatgtca tacacttctt tccagggcag    19740
tgggtaacaa agtttgactc cagaaagact tccctcgagg atttctactt ggatgaagag    19800
aggaccgtga gggtcccat gatgtcggac cctaaggctg ttttacgcta tggcttggat     19860
tcagatctca gctgcaaggt ctgtggggat aggggcaggg tggggggtgg atggagggag    19920
aggatagaga agcaaaacag ggtagtggga ataaaatgac ctttgagatc cgacagctgt    19980
ctacatgtcg cctgctgtgt gactttgagc aggttaataa catgtctgag ctttcctcct    20040
cttaagatgg ggcagggat cgttaccaac acttaccctc ccagggtttg ttgtaaggac     20100
gaataaggta ataggaaatg ggccctcagc actgggcacc cacatgtttg ttctcttgag    20160
actcctattt ctagaattta aagccaaact ttgaaaaata atgacaaact ccaaatcgtt    20220
ggcatctttt ttttttttg agacagtctc gctctgtcgg ccaggctgga gtccagtggc    20280
acgatctcgg ctcaccacaa cctccgcccc cgctgggtta aagcgattct cttgcctcag    20340
```

```
cctcctgagt agctgggatt acaggcgtgt gcctccatgc ctggctaatt ttatacagac    20400 gggtttctc catgttggtc aggctggtct caaactccca aactcaggtg atccgcctgc     20460
ctcggtctcc caaaacacag gggattccag gcatgagcca ccacgcttgg ccaatcgttg    20520
gcattctaag gctttcagtg tacctgactt cttttagttc taagtctgta actgttaacc   20580
tttcttgggc cacggctatc acacggatct ctctgggaat ctgacgacag tgcctcaaac   20640
ccgagggagc accgccaggt gtgcacacac gtttctgtca acgatttcgg aggactcttg   20700
ggatccctga acaccatctg ttccatggga ccttaggtta agagcctctg ttcaaaggag   20760
gcttttgctc ttggtgggtg gatggggtga agtctccaag ccctcttrcg gsccctctcgg  20820 tattcctatn ccccggttct gccctgtctt agtccagtgc tctctattta acaaatgagc    20880
agtaaatgta caccgatgga ctttgggaga caataaagac ctgatattca attctagctc    20940
cttaaaccac aggagaacat tctttcagca gacaacttca gttggtatta ggccaaggta    21000
agaaaggcca acagcatcct tttctgaaga aacctcagga gatggctctc tgccagaaag    21060
ctataacctg aaggggaat tgtaaaatag atgagggct ggatgaagga cgagaccagg      21120
gccccgtcac gggagaggga aggcagctcc tggctgtgtc tgtcccccgg cttttgggct    21180
ctgaaggact aaccacatgc tttctcactt gtctcagatt gcccagctgc ccttgaccgg    21240
aagcatgagt atcatcttct tcctgcccct gaaagtgacc cagaatttga ccttgataga    21300
ggagagcctc acctccgagt tcattcatga catagaccga gaactgaaga ccgtgcaggc    21360
ggtcctcact gtccccaagc tgaagctgag ttacgaaggc gaagtcacca agtccctgca    21420
ggagatgagt atgtctgaag acccttttcgc tcttggtggg tggatggggt ggggcagggt  21480
ctttgggcct tccactgtgc taagcagaac gcaagggctc cacaggcttg tagggggggcc  21540 gtggatgagt ccttaatcct catcgtgcca gaagggaagg ctgaactgcc ttctctcatc    21600
agactcattc ctcagcctca cgagcagacc tccctgacag gcgctcacaa cactgcctct    21660
caagacgagt ctgtctgacc tgttttctca tcttgaccta acttgctaaa tgctcctggg    21720
caagtcactc caccctcggt cagctcgac ctcttcaggc ctcagagaaa gtcaacagtg     21780
ctgcgccatc ccagcttgct tgcaaaggga tcccttggtt ggggtgttgg ggaaggcagg    21840
gttttaacgg aaatctctct ccatctctac agagctgcaa tccttgtttg attcaccaga    21900
ctttagcaag atcacaggca aacccatcaa gctgactcaa ggtggaacac cgggctggct    21960
ttgagtggaa cgaggatggg gcgggaacca ccccagccc agggctgcag cctgcccacc     22020
tcaccttccc gctggactat caccttaacc agcctttcat cttcgtactg agggacacag    22080
acacaggggc ccttctcttc attggcaaga ttctggaccc cagggggcccc taatatccca   22140 gtttaatatt ccaatacccct agaagaaaac ccgagggaca gcagattcca caggacacga   22200 aggctgccc tgtaaggttt caatgcatac aataaaagag ctttatccct aacttctgtt     22260
acttcgttcc tcctcctatt ttgagctatg cgaaatatca tatgaagaga aacagctctt    22320
gaggaatttg gtggtcctct acttctagcc tggttttatc taaacactgc aggaagtcac    22380
cgttcataag aactcttagt tacctgtgtt ggataaggca cggacagctt ctctgctctg    22440
ggggtatttc tgtactagga tcagtgatcc tcccgggagg                          22480
```

<210> SEQ ID NO 44
<211> LENGTH: 11
<212> TYPE: DNA
<213> ORGANISM: Artificial Sequence
<220> FEATURE:
<223> OTHER INFORMATION: Synthetic construct

```
<400> SEQUENCE: 44
gtaaagttaa c                                                      11

<210> SEQ ID NO 45
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: n is a, c, g, or t

<400> SEQUENCE: 45
gtaatnatta ac                                                     12

<210> SEQ ID NO 46
<211> LENGTH: 17
<212> TYPE: DNA
<213> ORGANISM: Artificial Sequence
<220> FEATURE:
<223> OTHER INFORMATION: Synthetic construct

<400> SEQUENCE: 46
tcaggtgatg cacctgc                                                17

<210> SEQ ID NO 47
<211> LENGTH: 16
<212> TYPE: DNA
<213> ORGANISM: Artificial Sequence
<220> FEATURE:
<223> OTHER INFORMATION: Synthetic construct

<400> SEQUENCE: 47
tcaggtcatg acctga                                                 16

<210> SEQ ID NO 48
<211> LENGTH: 13
<212> TYPE: DNA
<213> ORGANISM: Artificial Sequence
<220> FEATURE:
<223> OTHER INFORMATION: Synthetic construct

<400> SEQUENCE: 48
aggtgatgca cct                                                    13

<210> SEQ ID NO 49
<211> LENGTH: 12
<212> TYPE: DNA
<213> ORGANISM: Artificial Sequence
<220> FEATURE:
<223> OTHER INFORMATION: Synthetic construct

<400> SEQUENCE: 49
aggtcatgac ct                                                     12

<210> SEQ ID NO 50
<211> LENGTH: 12
<212> TYPE: DNA
<213> ORGANISM: Artificial Sequence
<220> FEATURE:
<223> OTHER INFORMATION: Synthetic construct

<400> SEQUENCE: 50
gttggtatat ag                                                     12
```